United States Patent [19]

Sprecker et al.

[11] Patent Number: 4,668,817
[45] Date of Patent: May 26, 1987

[54] ALKYL SUBSTITUTED PARA-CARBOALKOXY CYCLOHEXANONES

[75] Inventors: Mark A. Sprecker, Sea Bright; Wilhelmus J. Wiegers, Red Bank; Robert P. Belko, Woodbridge; Richard M. Boden, Ocean, all of N.J.

[73] Assignee: International Flavors & Fragrances Inc., New York, N.Y.

[21] Appl. No.: 842,836

[22] Filed: Mar. 21, 1986

Related U.S. Application Data

[62] Division of Ser. No. 726,603, Apr. 23, 1985, which is a division of Ser. No. 563,801, Dec. 21, 1983, Pat. No. 4,537,704.

[51] Int. Cl.⁴ .......................................... C07C 69/757
[52] U.S. Cl. ................................................. 560/126
[58] Field of Search ........................ 560/126; 562/508

[56] References Cited

U.S. PATENT DOCUMENTS

| | | | |
|---|---|---|---|
| 3,954,834 | 5/1976 | Cohen | 562/504 X |
| 4,310,701 | 1/1982 | Wilson et al. | 568/347 |
| 4,537,704 | 8/1985 | Sprecker et al. | 252/522 R |

FOREIGN PATENT DOCUMENTS 0907431 10/1962 United Kingdom .

Primary Examiner—Natalie Trousof
Assistant Examiner—Patricia M. Scott
Attorney, Agent, or Firm—Arthur L. Liberman

[57] ABSTRACT

Described are para-carboalkoxy cyclohexanones defined according to the structure:

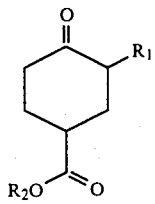

wherein $R_1$ represents hydrogen or $C_1$–$C_7$ alkyl and $R_2$ represents methyl or ethyl and uses thereof in augmenting or enhancing the aroma of consumable materials including foodstuffs, chewing gums, toothpastes, medicinal products, chewing tobaccos, perfume compositions, colognes and perfumed articles (e.g., solid or liquid anionic, cationic, nonionic or zwitterionic detergents, cosmetic compositions, fabric softener compositions, fabric softener articles, hair preparations and perfumed polymers. The compounds defined according to the structure:

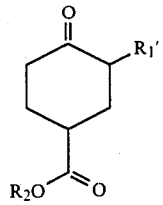

wherein $R_1'$ represents $C_4$–$C_7$ alkyl and $R_2$ represents methyl or ethyl are novel compounds.

5 Claims, 38 Drawing Figures

GLC PROFILE FOR EXAMPLE I.

IR SPECTRUM FOR FRACTION 4 FOR EXAMPLE I.

NMR SPECTRUM FOR FRACTION 4 OF EXAMPLE I.

NMR SPECTRUM FOR FRACTION 7 OF EXAMPLE II.

GLC PROFILE FOR EXAMPLE III.

GLC PROFILE FOR EXAMPLE III.

GLC PROFILE FOR EXAMPLE IV.

GLC PROFILE FOR EXAMPLE IV.

NMR SPECTRUM FOR EXAMPLE IV.

IR SPECTRUM FOR EXAMPLE IV.

GLC PROFILE FOR EXAMPLE V.

GLC PROFILE FOR EXAMPLE V.

NMR SPECTRUM FOR EXAMPLE V.

IR SPECTRUM FOR EXAMPLE V.

NMR SPECTRUM FOR EXAMPLE VI.

IR SPECTRUM FOR EXAMPLE VI.

GLC PROFILE FOR EXAMPLE VII.

GLC PROFILE FOR EXAMPLE VII.

NMR SPECTRUM FOR EXAMPLE VII.

IR SPECTRUM FOR EXAMPLE VII.

GLC PROFILE FOR EXAMPLE VIII.

GLC PROFILE FOR EXAMPLE VIII.

NMR SPECTRUM FOR EXAMPLE VIII.

IR SPECTRUM FOR EXAMPLE VIII.

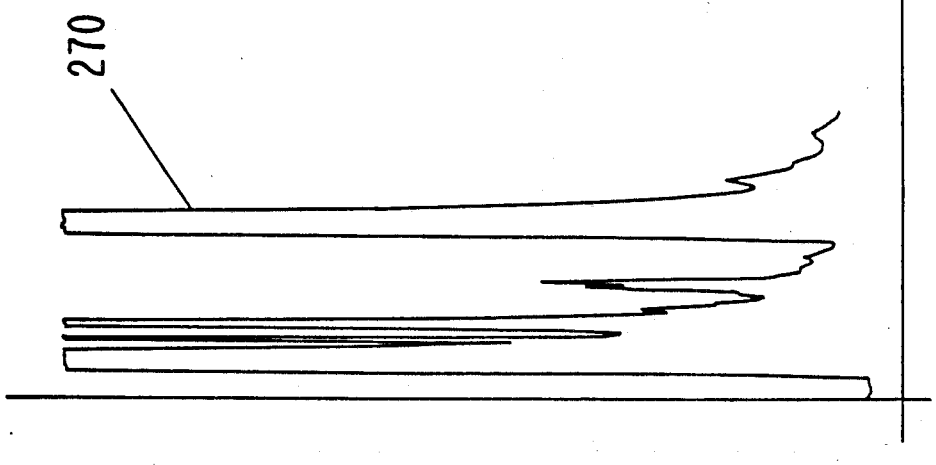
FIG. 26 GLC PROFILE FOR EXAMPLE IX.
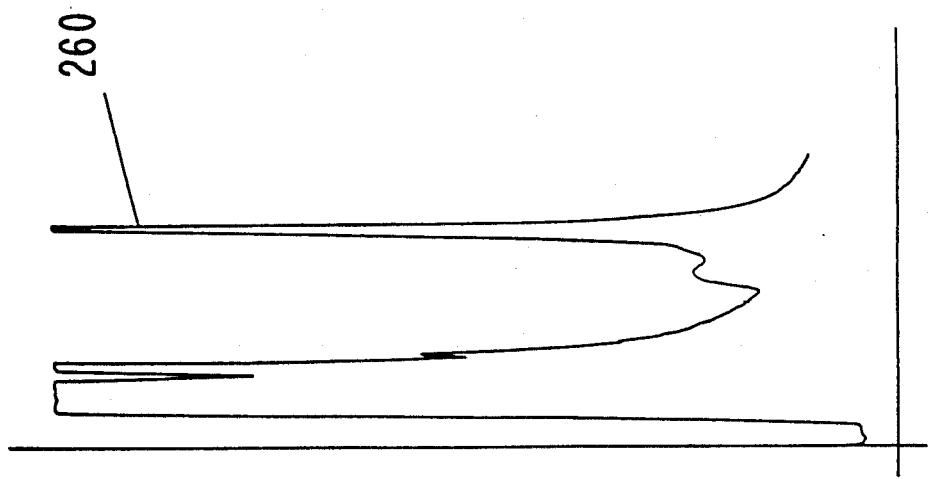
FIG. 27 GLC PROFILE FOR EXAMPLE IX.

NMR SPECTRUM FOR EXAMPLE IX.

IR SPECTRUM FOR EXAMPLE IX.

NMR SPECTRUM FOR EXAMPLE X.

IR SPECTRUM FOR EXAMPLE X.

NMR SPECTRUM FOR EXAMPLE XI(A).

IR SPECTRUM FOR EXAMPLE XI(A).

GLC PROFILE FOR EXAMPLE XI.

NMR SPECTRUM FOR EXAMPLE XI(B)

IR SPECTRUM FOR EXAMPLE XI(B).

ALKYL SUBSTITUTED PARA-CARBOALKOXY CYCLOHEXANONES

This is a divisional of application Ser. No. 726,603, filed Apr. 23, 1985 which, in turn, is a stream-line divisional application of U.S. Letters Patent Ser. No. 563,801 filed Dec. 21, 1983, now U.S. Pat. No. 4,537,704 issued Aug. 27, 1985.

BACKGROUND OF THE INVENTION

This invention relates to para-carboalkoxy cyclohexanones defined according to the structure:

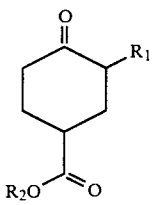

wherein $R_1$ represents hydrogen or $C_1-C_7$ alkyl and $R_2$ represents methyl or ethyl and uses thereof in augmenting or enhancing the aroma or taste of consumable materials.

There has been considerable work performed relating to substances which can be used to impart (modify, augment or enhance) flavors to (or in) foodstuffs. These substances are used to diminish the use of natural materials, some of which may be in short supply and to provide more uniform properties in the finished product.

Nutty, raspberry, kernel-like, tart, unripened lime, bitter, lemony, green, caramel-like, maple sugar-like, maple/hazel-nut, and intense cocoa and coffee, fresh almond aroma and taste with blueberry-like and coffee nuances are particularly desirable for uses in many foodstuff flavors, particularly in raspberry ice cream flavors, cooked raspberry pies, blueberry pies and the like.

Fruity, woody, strawberry-like, raspberry-like, green, fresh floral, jasmine-like, lemony, burnt maple, maple/nutty, meaty, cocoa, coffee and valerian-like aromas with woody, ionone-like, sweep raspberry-like, licorice-like, jasmine-like, citrusy, lemon, and toasted almond undertones are particularly desirable in augmenting or enhancing the aroma of perfume compositions, colognes and perfumed articles (e.g., solid or liquid anionic, cationic, nonionic or zwitterionc detergents, fabric softener compositions, fabric softener articles, hair preparations, cosmetic powders and perfumed polymers.

Perfume uses of carboalkoxy cyclohexanones and carboalkoxy cyclopentenones are well known in the prior art. Thus, U.S. Pat. No. 4,310,701 issued on Jan. 12, 1982 discloses compounds defined according to the generic structure:

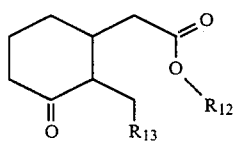

wherein $R_{13}$ represents $C_1-C_4$ alkyl and $R_{12}$ represents $C_1-C_3$ alkyl. United Kingdom Patent Specification No. 907,431 published on Oct. 3, 1962 discloses compounds defined according to the generic structure:

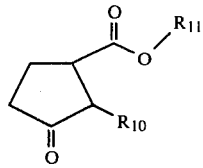

as being useful in perfumery (wherein $R_{11}$ represents lower alkyl and $R_{10}$ represents lower alkyl).

Para-carboalkoxy cyclohexanones substituted at a position alpha to the keto moiety are also well known in the prior art. Thus, the compound defined according to the structure:

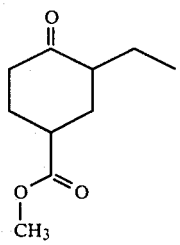

has been indicated to have been synthesized by Huffman & Sawdaye at Synth. Comm. 11(12) 979-81 (1981).

Furthermore, Sengupta, J. Org. Chem. 18, 249-55(1953) abstracted at Chem. Abstracts, Vol. 48, 1976 discloses the compound defined according to the structure:

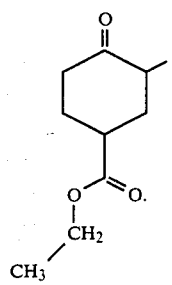

Neither Huffman & Sawdaye nor Sengupta disclosed their organoleptic uses of these compounds.

Nothing in the prior art discloses the use of the para-carboalkoxy cyclohexanones defined according to the structure:

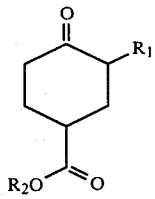

wherein $R_1$ represents hydrogen or $C_1-C_7$ alkyl and $R_2$ represents methyl or ethyl in augmenting or enhancing the aroma or taste of consumable materials such as foofstuffs, perfume compositions, colognes and perfumed articles. Nothing in the prior art discloses the unobvious, unexpected and advantageous properties of the genus of compounds defined according to the structure:

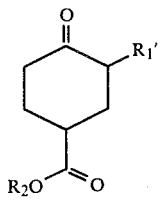

wherein $R_1'$ represents $C_4$–$C_7$ alkyl and $R_2$ represents methyl and ethyl.

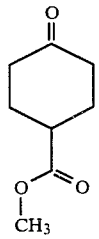

(conditions: Carbowax column programmed at 225° C. isothermal).

Figure 2:
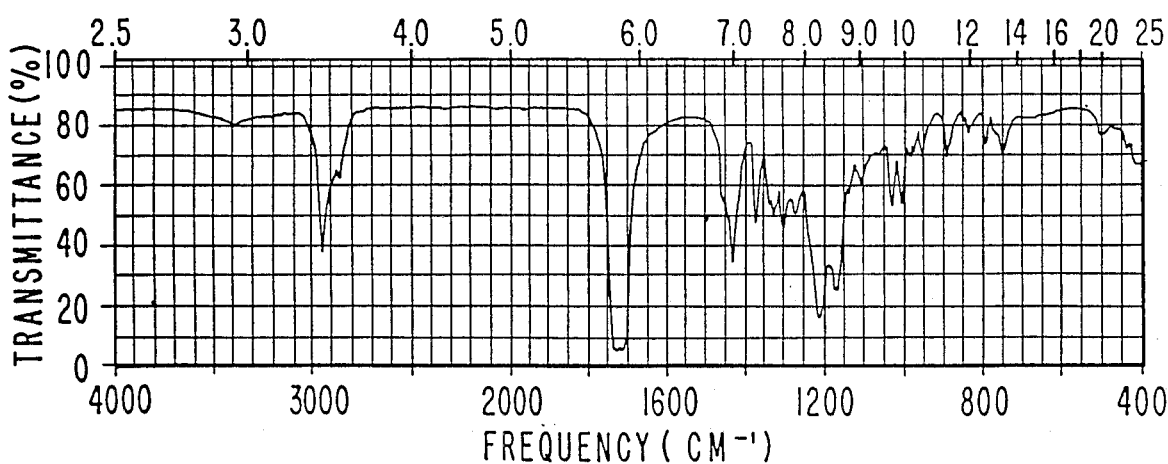

FIG. 2 is the infra-red spectrum for Fraction 4 of the distillation product of the reaction product of Example I containing the compound having the structure:

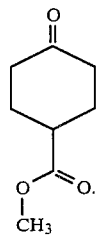

Figure 3:
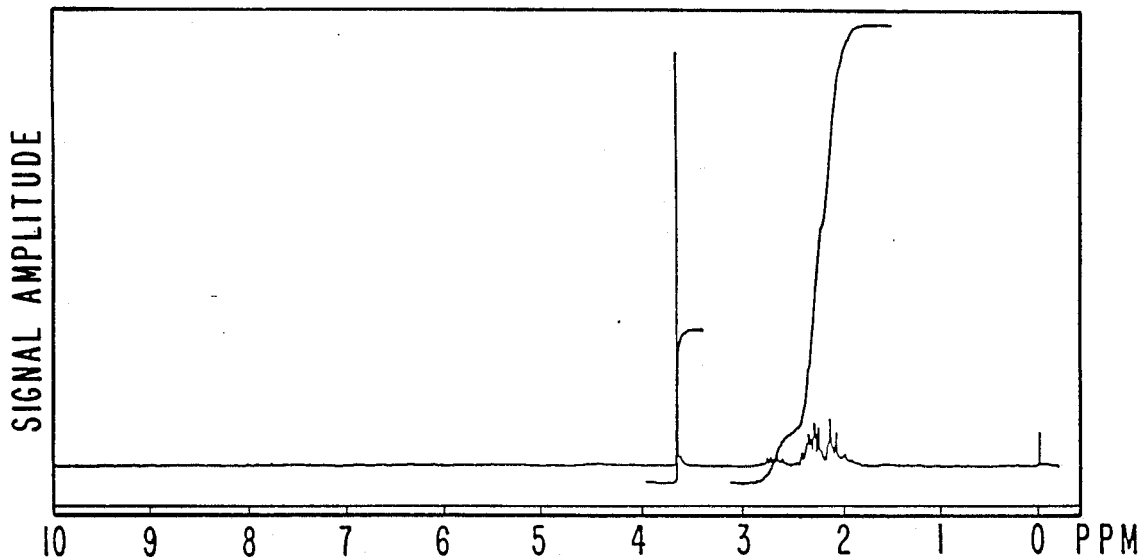

FIG. 3 is the NMR spectrum for Fraction 4 of the distillation product of the reaction product of Example I containing the compound having the structure:

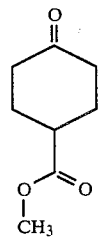

(conditions: Field strength: 100 MHz; Solvent: $CFCl_3$).

Figure 4:
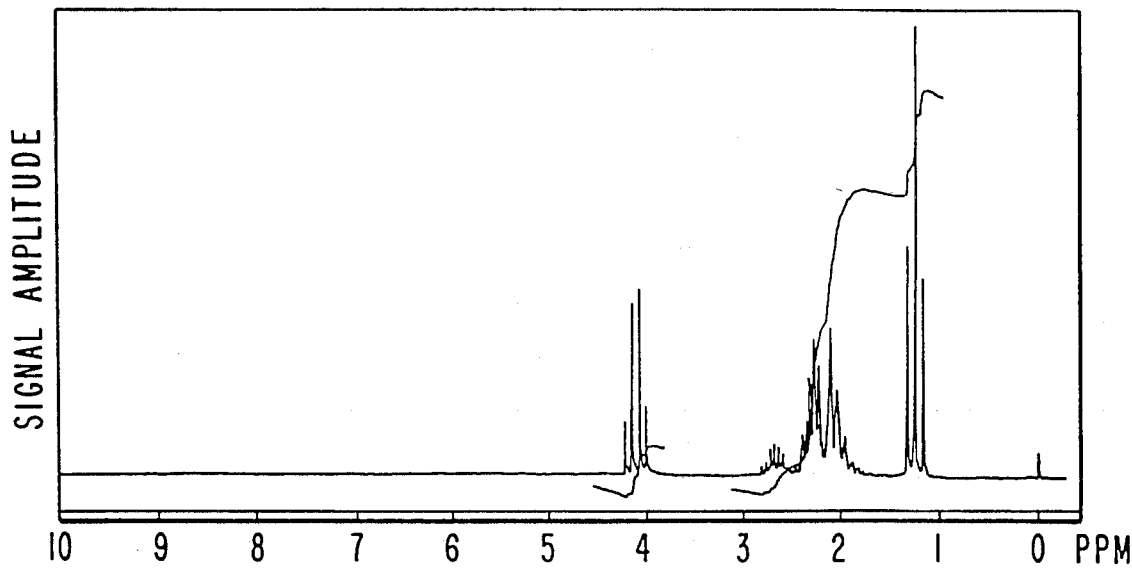

FIG. 4 is the NMR spectrum for Fraction 7 of the distillation product of the reaction product of Example II containing the compound having the structure:

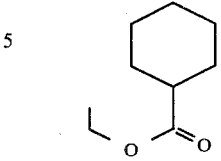

(conditions: Field strength: 100 MHz; Solvent: $CFCl_3$).

Figure 5:
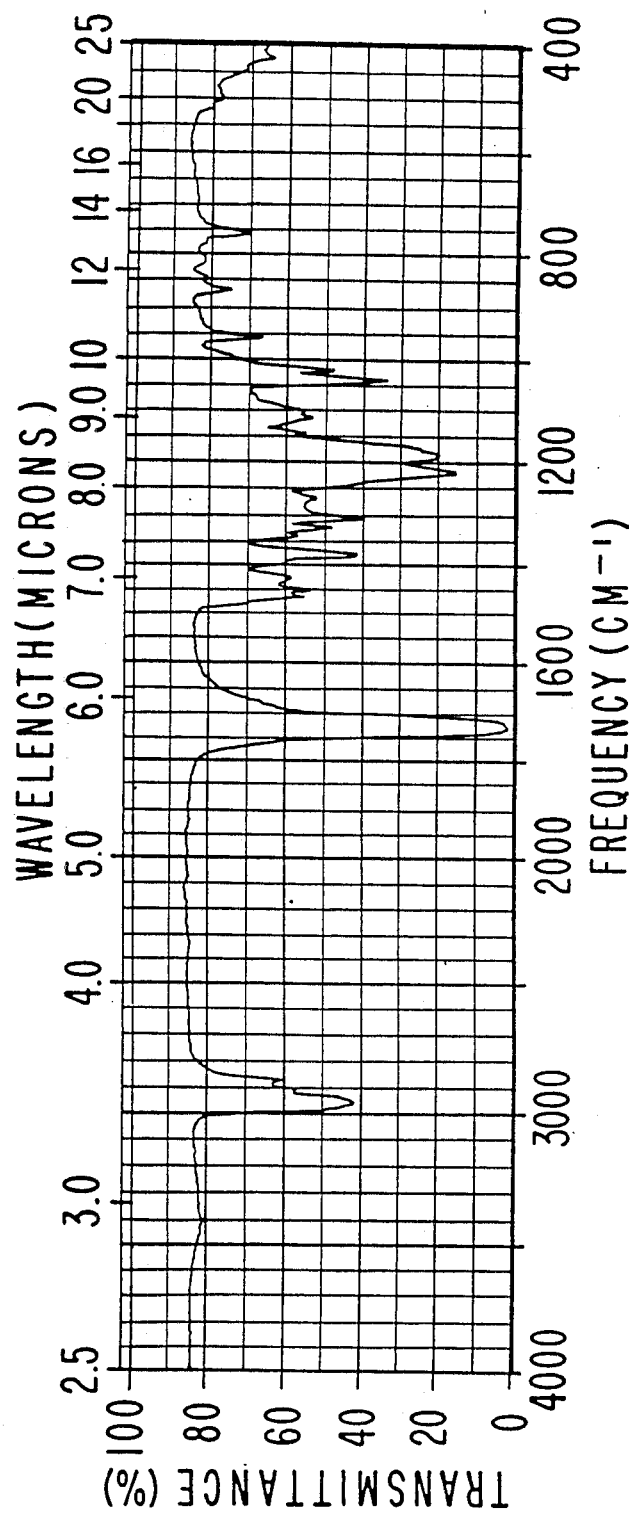

FIG. 5 is the infra-red spectrum for Fraction 7 of the distillation product of the reaction product of Example II containing the compound having the structure:

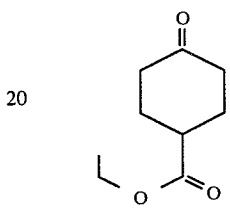

Figure 6:
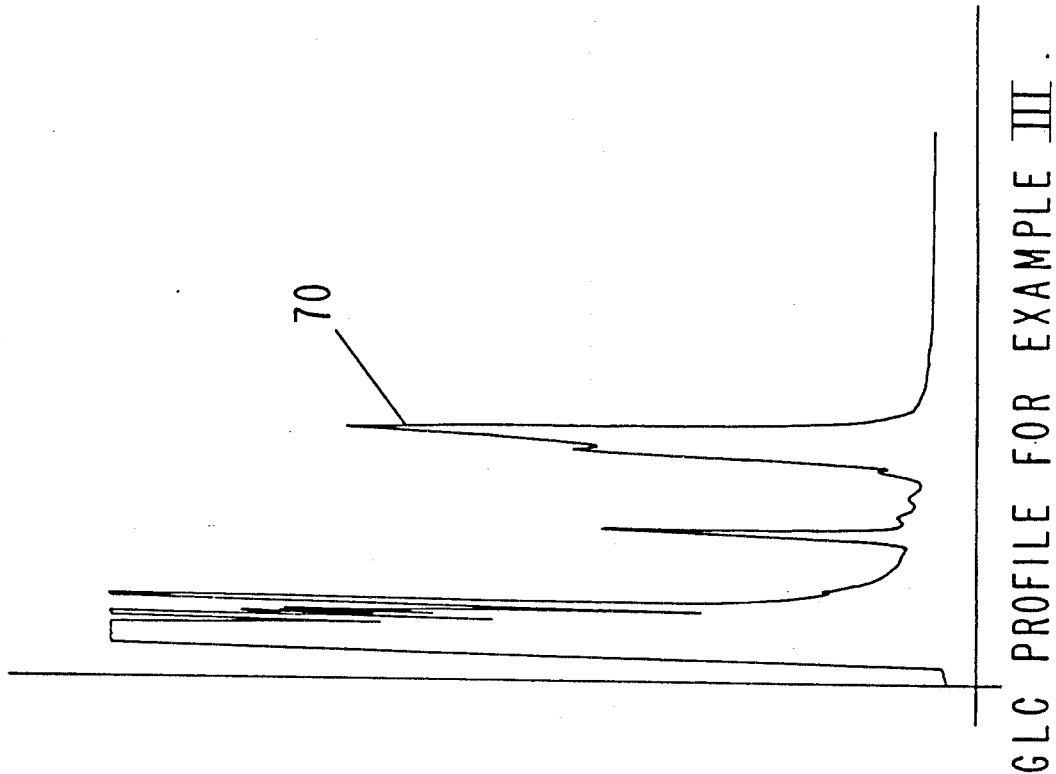

FIG. 6 is the GLC profile for the reaction product of Example III containing the compound having the structure:

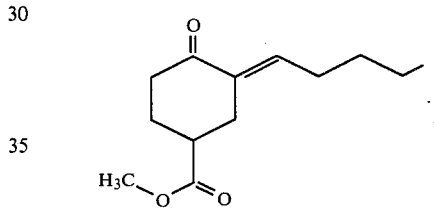

Figure 7:
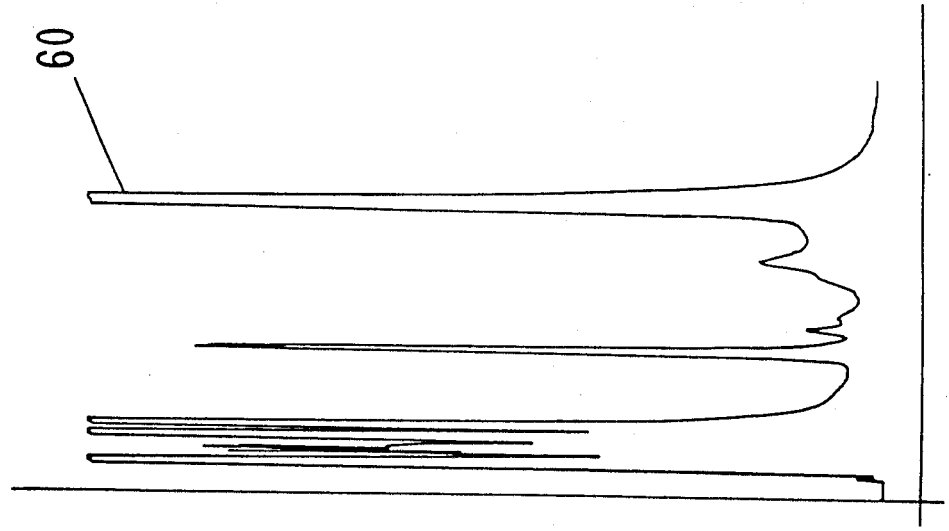

FIG. 7 is the GLC profile for the reaction product of Example III containing the compound having the structure:

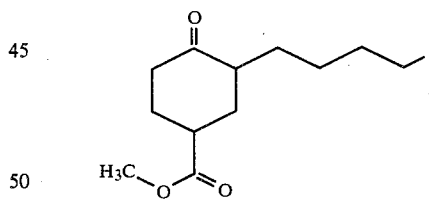

Figure 8:
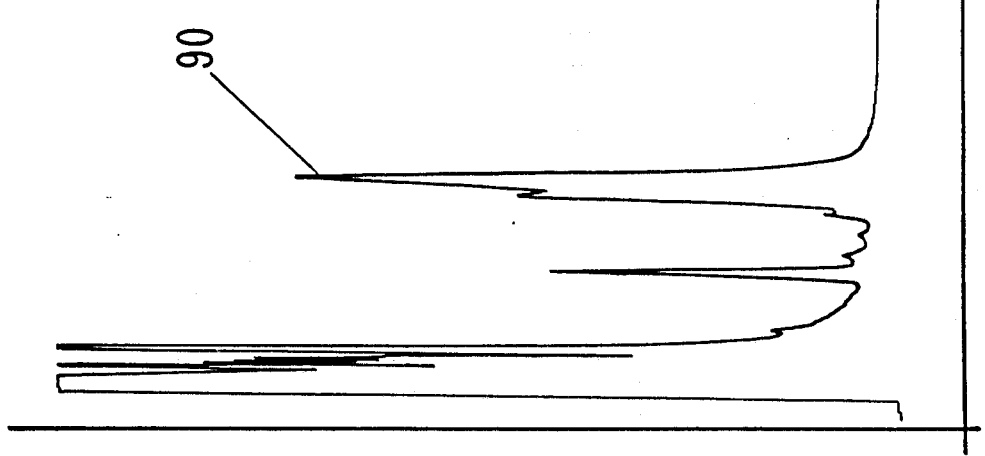

FIG. 8 is the GLC profile for the reaction product of Example IV containing the compound having the structure:

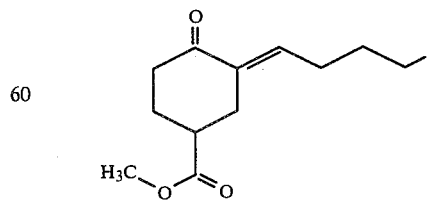

Figure 9:
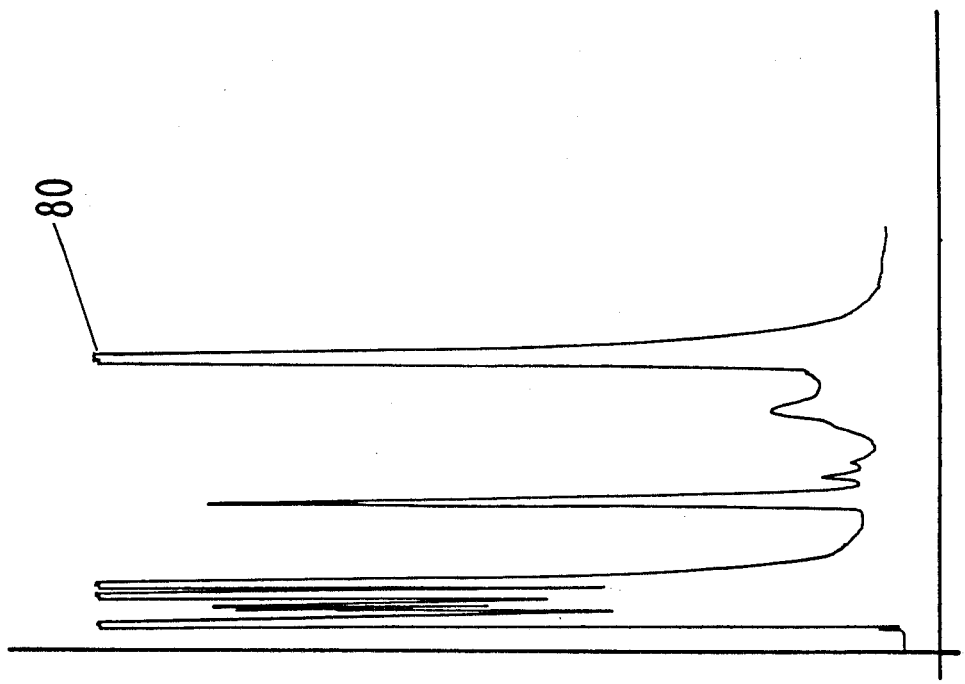

FIG. 9 is the GLC profile for the reaction product of Example IV containing the structure:

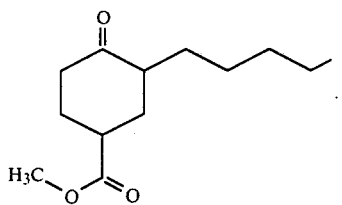

Figure 10:
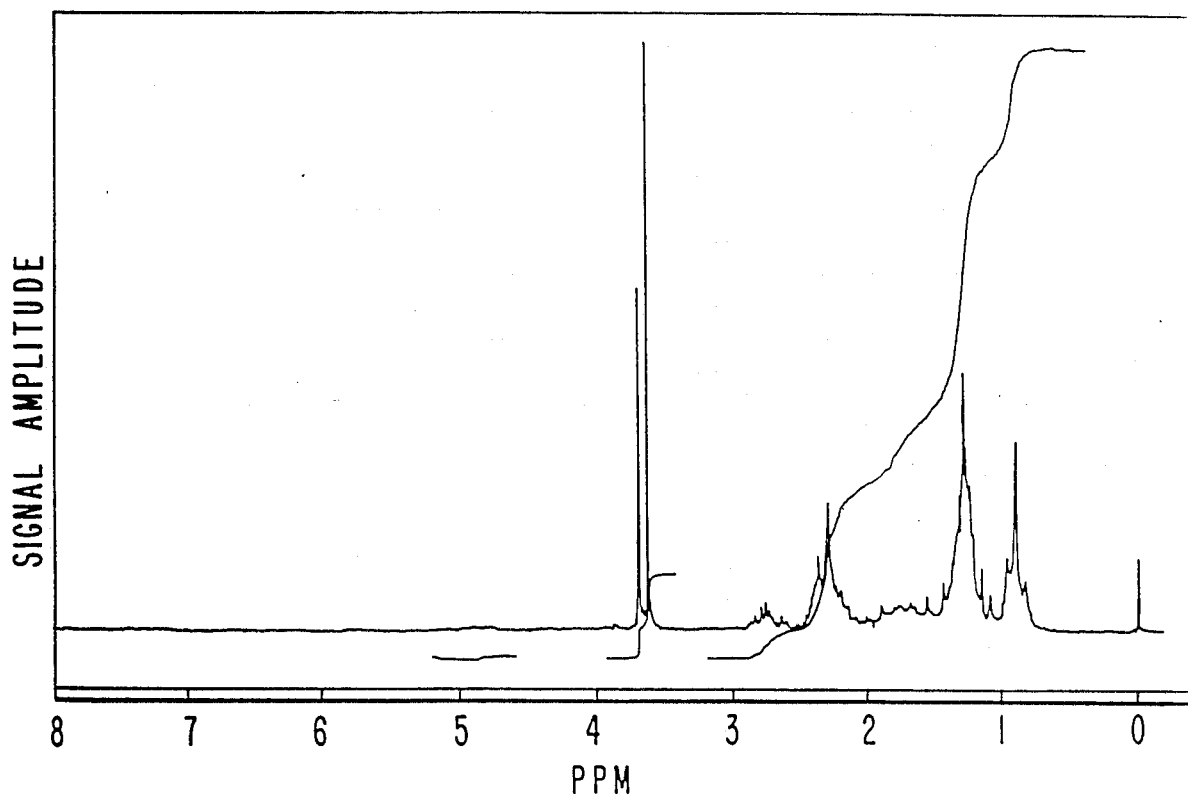

FIG. 10 is the NMR spectrum for the reaction product of Example IV containing the compound having the structure:

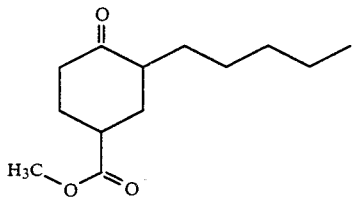

(conditions: Field strength: 100 MHz; Solvent: CFCl₃).

Figure 11:
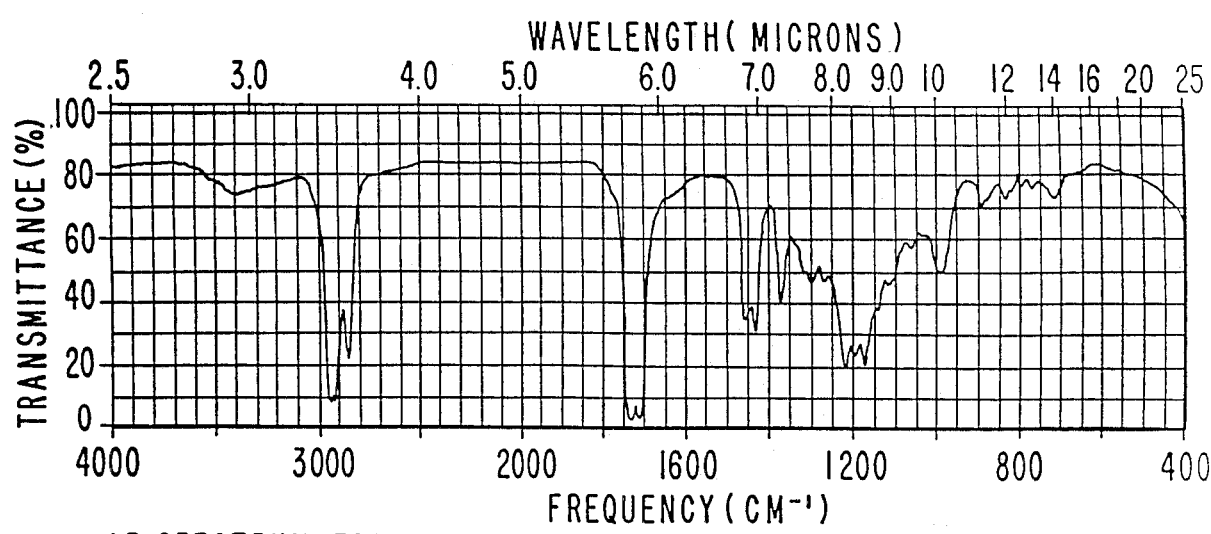

FIG. 11 is the NMR spectrum for the reaction product of Example IV containing the compound having the structure:

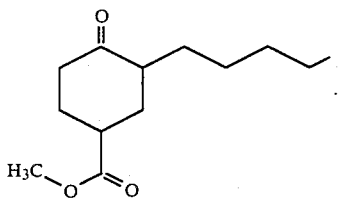

Figure 12:
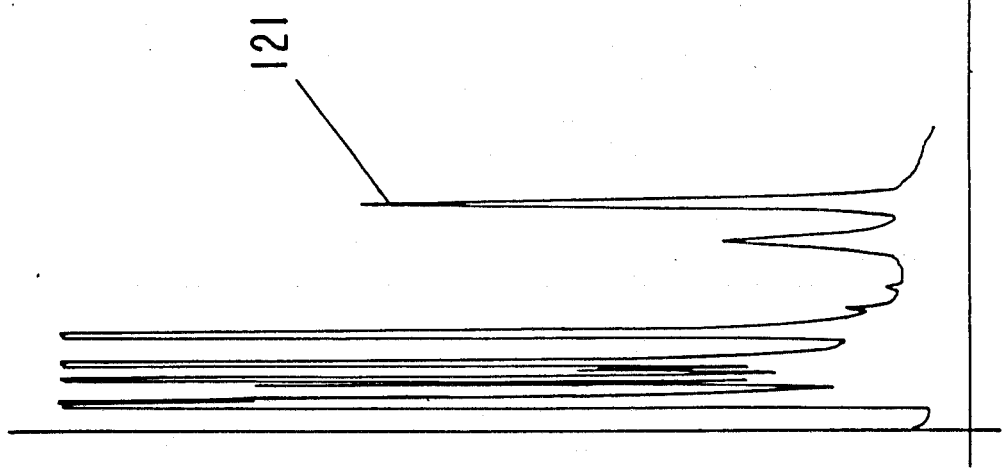

FIG. 12 is the GLC profile for the reaction product of Example V containing the compound having the structure:

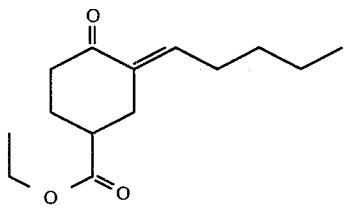

(conditions: SE-30 column programmed at 180° C. isothermal).

Figure 13:
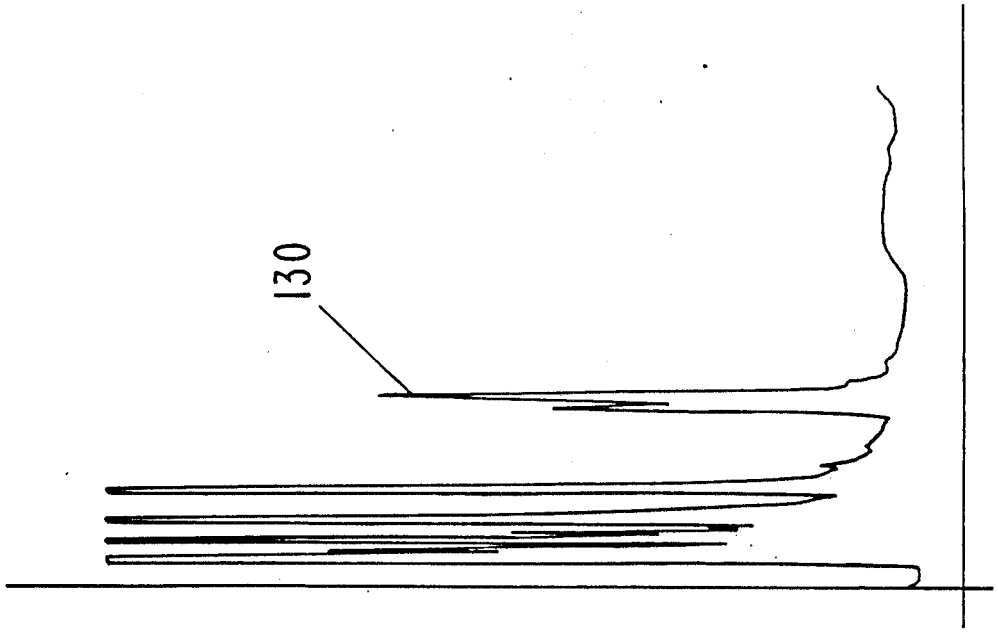

FIG. 13 is the GLC profile for the reaction product of Example V containing the compound having the structure:

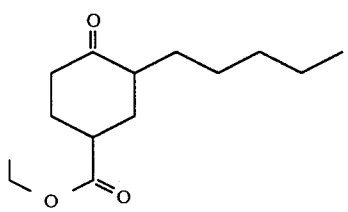

(Conditions: SE-30 column programmed at 220° C. isothermal).

Figure 14:
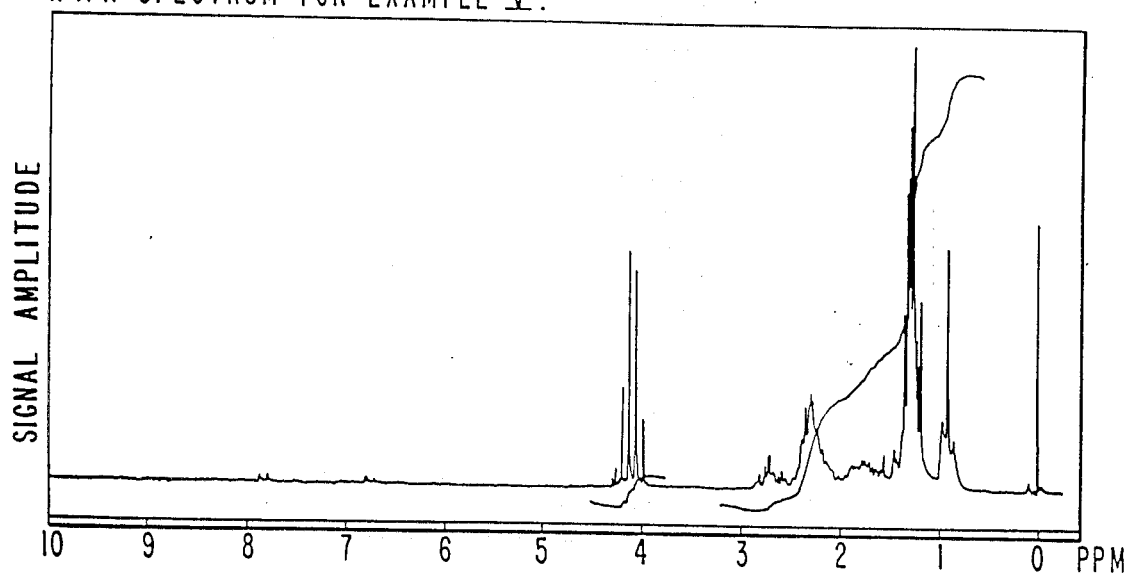

FIG. 14 is the NMR spectrum for the compound having the structure:

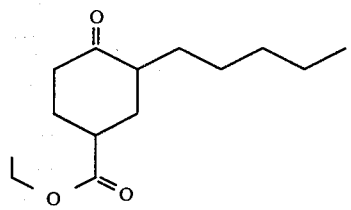

produced according to Example V. (Conditions: Field strength: 100 MHz; Solvent: CFCl₃).

Figure 15:
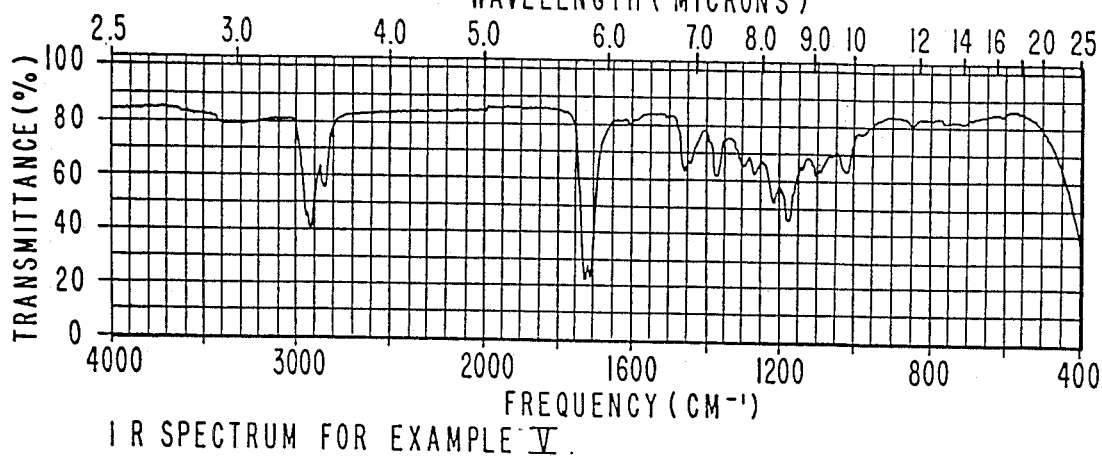

FIG. 15 is the infra-red spectrum for the compound having the structure:

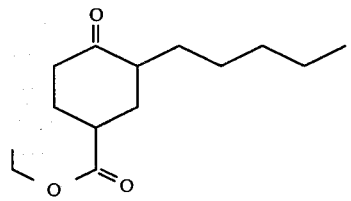

produced according to Example V.

Figure 16:
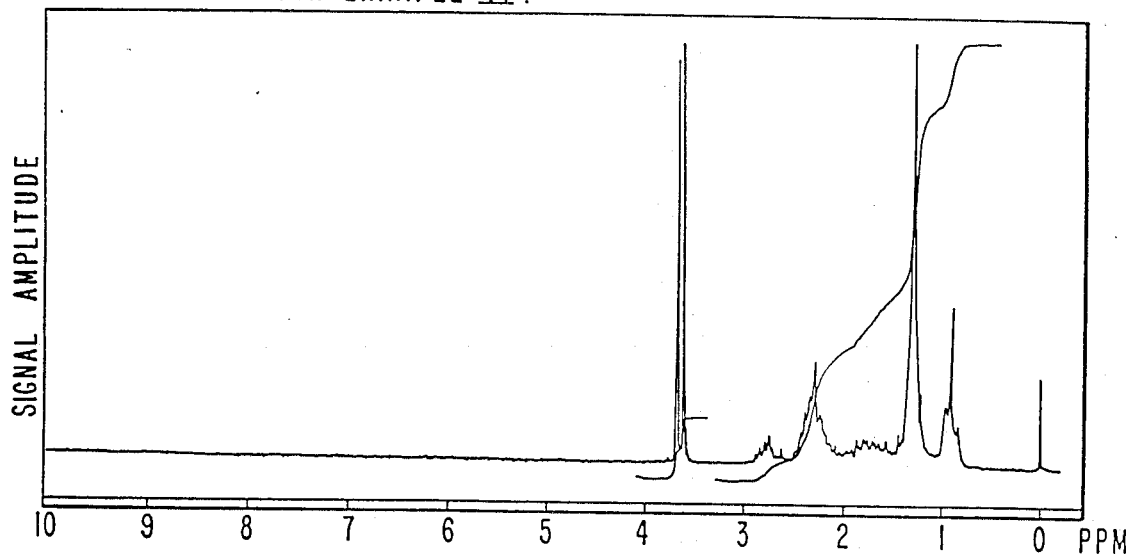

FIG. 16 is the NMR spectrum for the compound having the structure:

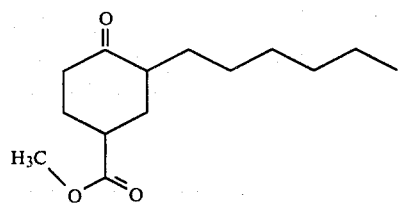

produced according to Example VI. (Conditions: Field strength: 100 MHz; Solvent: CFCl₃).

Figure 17:
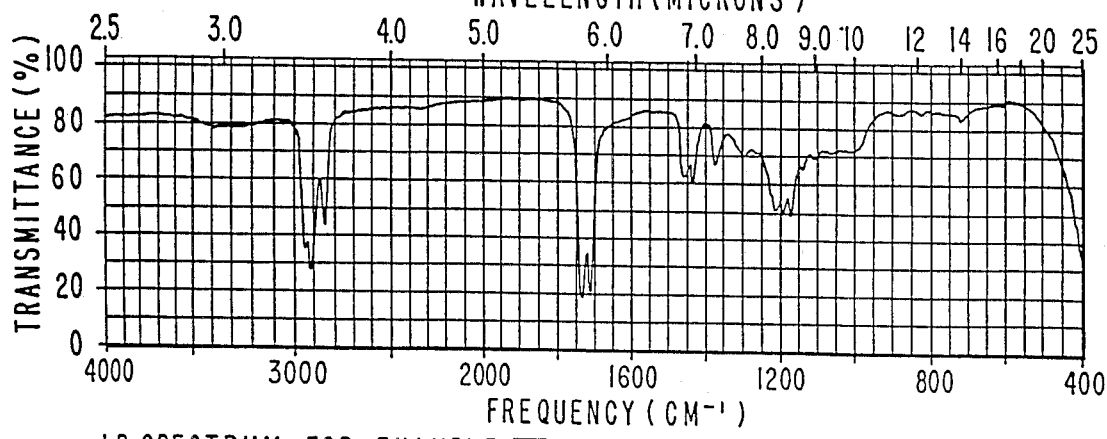

FIG. 17 is the infra-red spectrum for the compound having the structure:

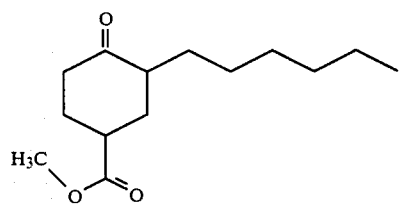

produced according to Example VI. (Conditions: Field strength: 100 MHz; Solvent: CFCl₃).

Figure 18:
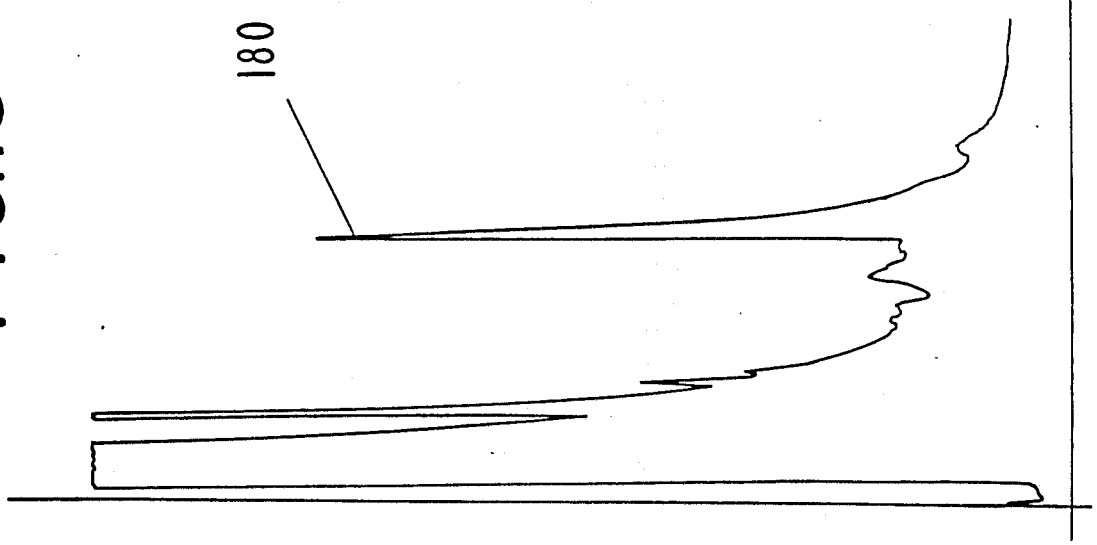

FIG. 18 is the GLC profile for the reaction product of Example VII containing the compound having the structure:

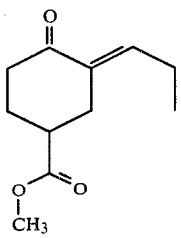

(conditions: 10% SE-30 column programmed at 180° C. isothermal).

Figure 19:
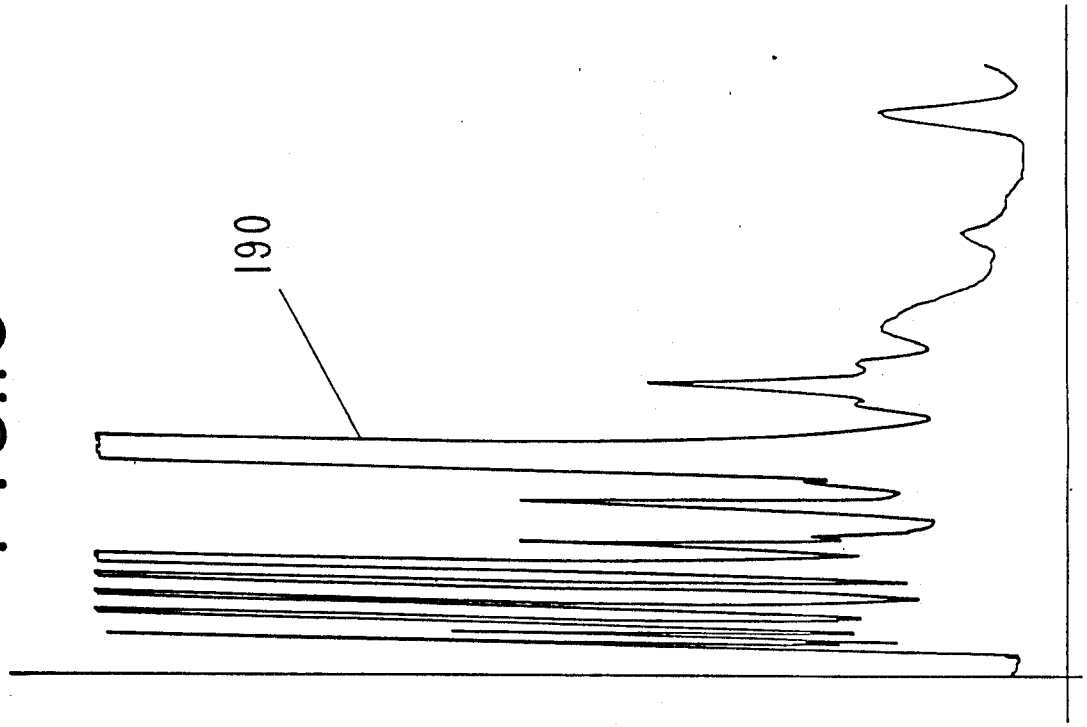

FIG. 19 is the GLC profile for the reaction product of Example VII containing the compound having the structure:

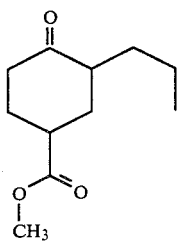

(conditions: 10% SE-30 column programmed at 220° C. isothermal).

Figure 20:
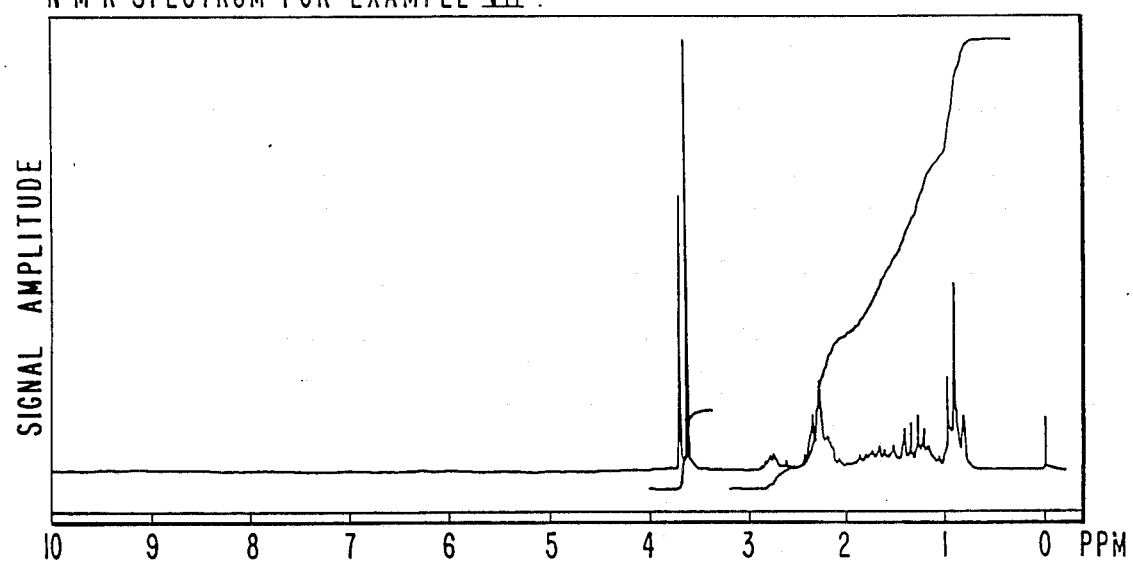

FIG. 20 is the NMR spectrum for the reaction product of Example VII containing the compound having the structure:

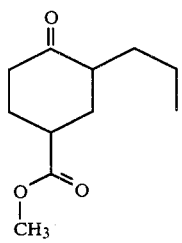

(conditions: Field strength: 100 MHz; Solvent: CFCl₃).

Figure 21:
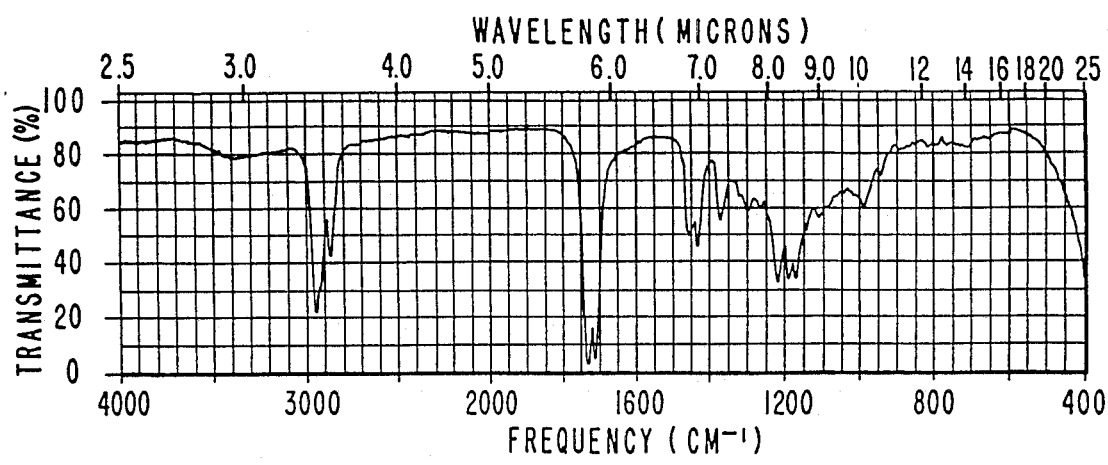

FIG. 21 is the infra-red spectrum for the compound having the structure:

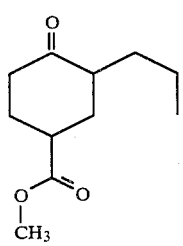

produced according to Example VII.

Figure 22:
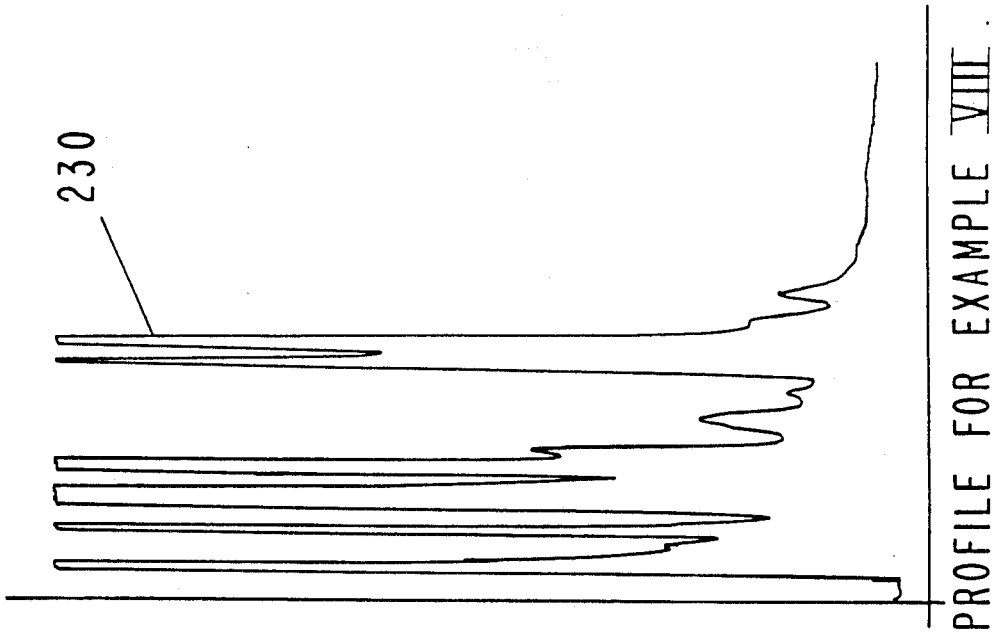

FIG. 22 is the GLC profile for the reaction product of Example VIII containing the compound having the structure:

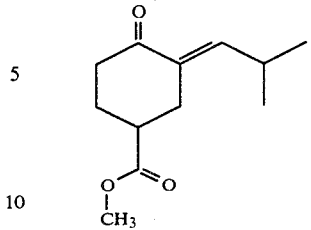

(conditions: 10% SE-30 column programmed at 180° C. isothermal).

Figure 23:
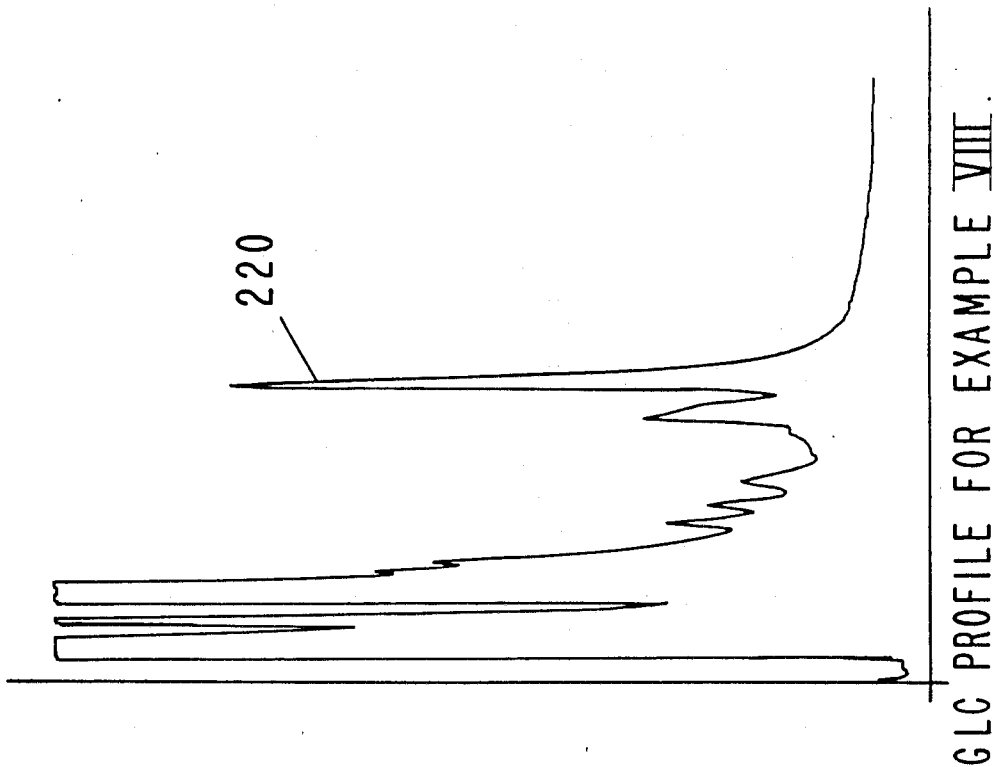

FIG. 23 is the GLC profile for the reaction product of Example VIII containing the compound having the structure:

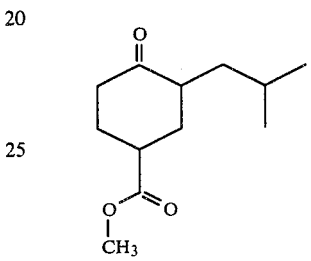

(conditions: 10% SE-30 column programmed at 220° C. isothermal).

Figure 24:
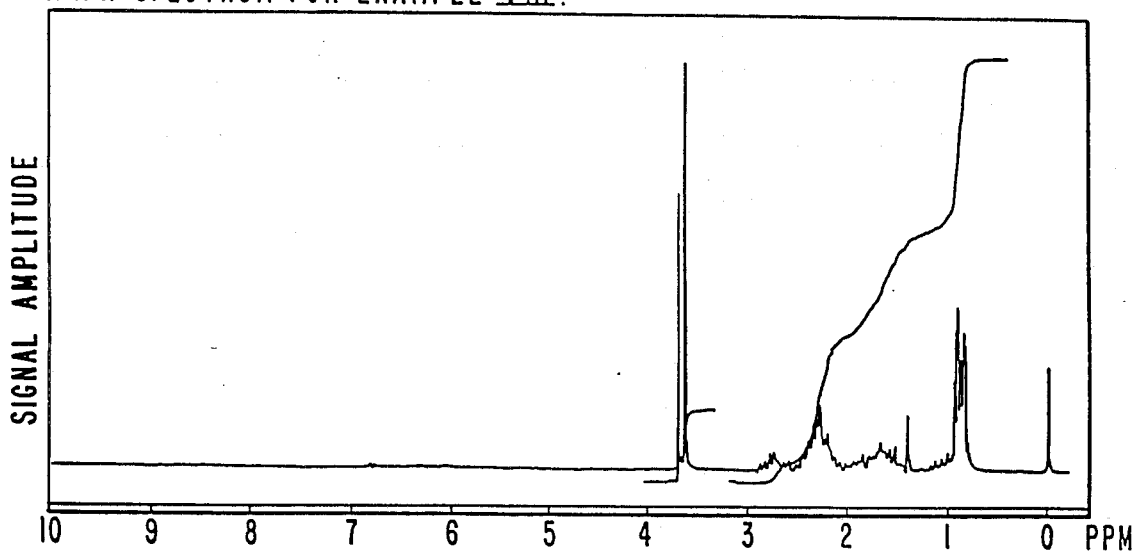

FIG. 24 is the NMR spectrum for the reaction product of Example VIII containing the compound having the structure:

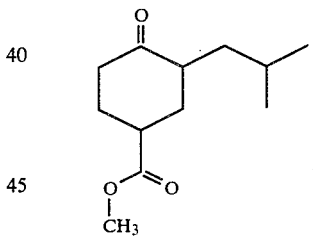

(conditions: Field strength: 100 MHz; Solvent: CFCl₃).

Figure 25:
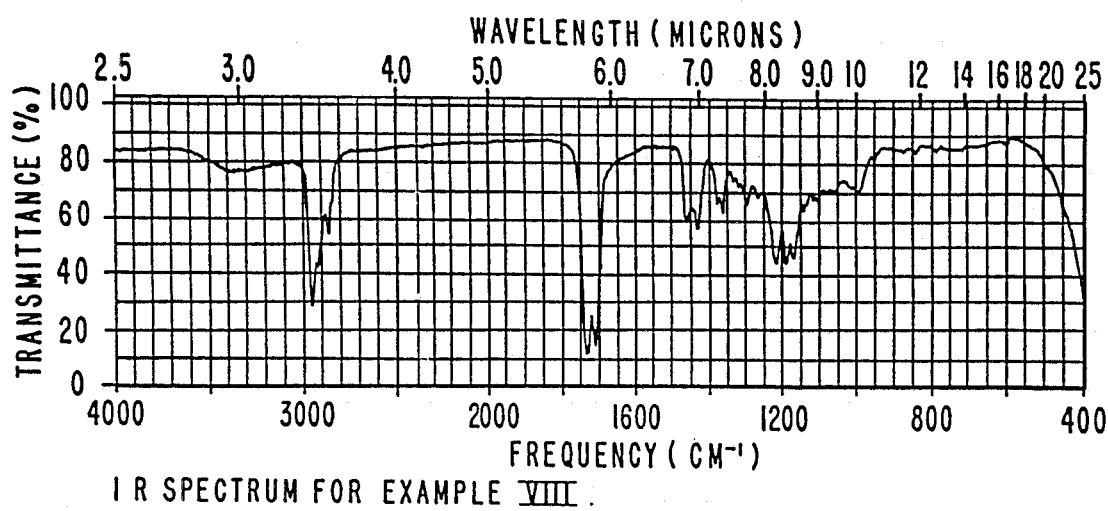

FIG. 25 is the infra-red spectrum for the reaction product of Example VIII containing the compound having the structure:

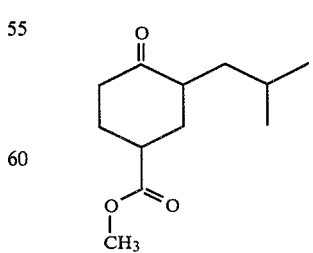

FIG. 26 is the GLC profile for the reaction product of Example IX containing the structure:

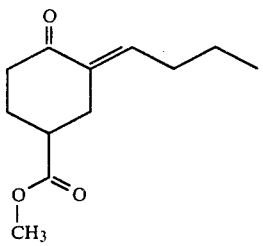

(crude) (conditions: 10% SE-30 column programmed at 180° C. isothermal).

FIG. 27 is the GLC profile for the reaction product of Example IX containing the compound having the structure:

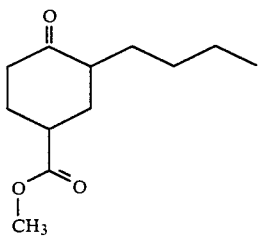

(conditions: 10% SE-30 column programmed at 220° C. isothermal).

Figure 28:
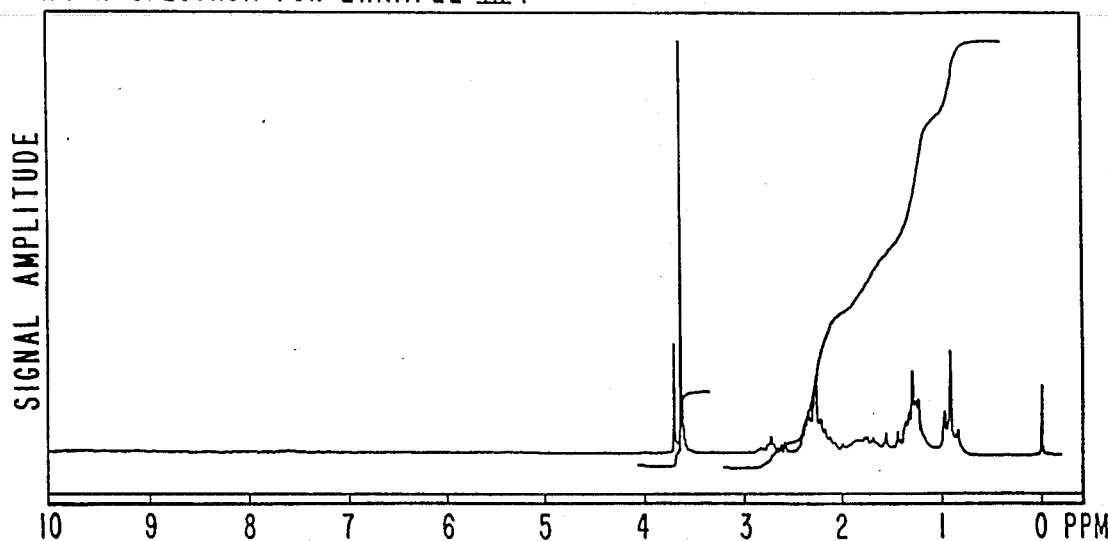
Figure 29:
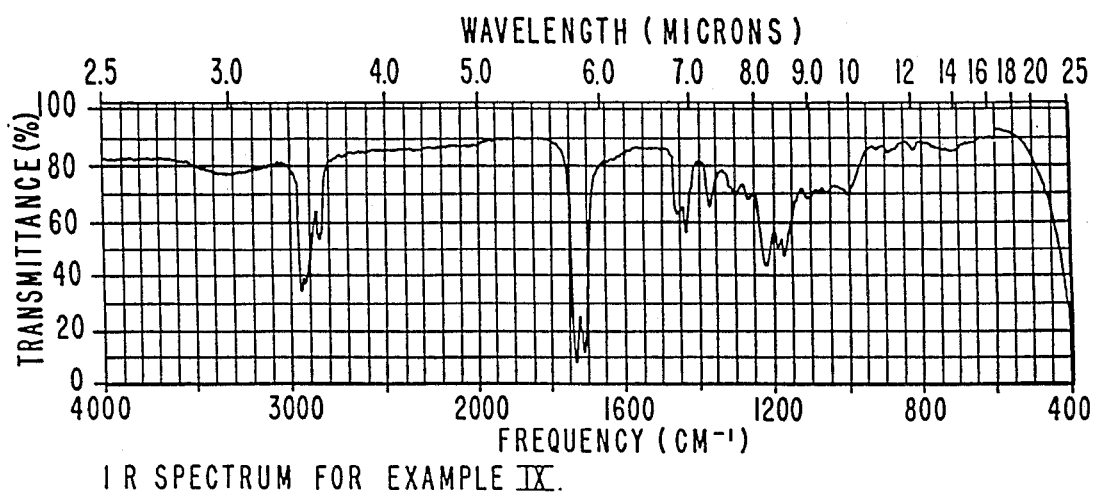

FIG. 28 is the NMR spectrum for the compound having the structure:

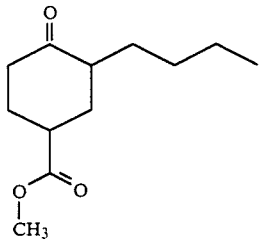

produced according to Example IX. (Conditions: Field strength: 100 MHz; Solvent: CFCl$_3$). FIG. 29 is the infra-red spectrum for the reaction product of Example IX containing the compound having the structure:

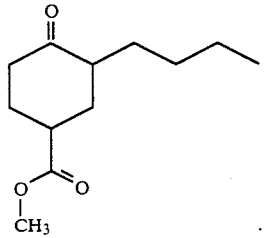

Figure 30:
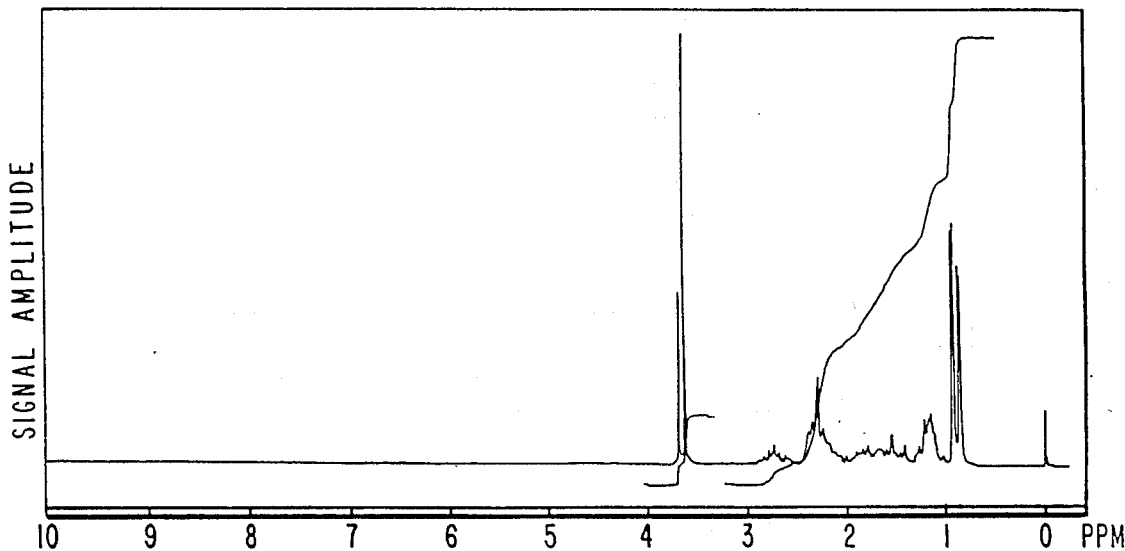

FIG. 30 is the NMR spectrum for the reaction product of Example X containing the compound having the structure:

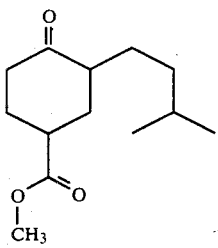

(conditions: Field strength: 100 MHz; Solvent: CFCl$_3$).

Figure 31:
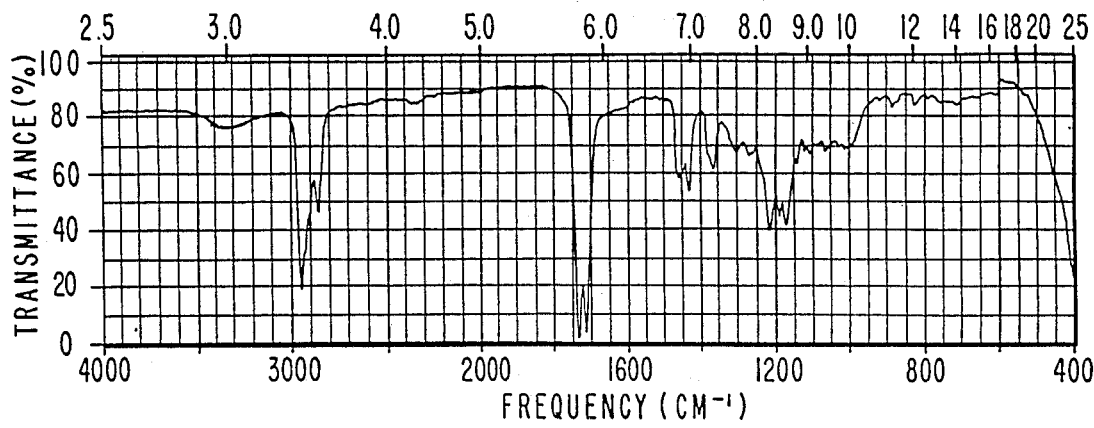

FIG. 31 is the infra-red spectrum for the compound having the structure:

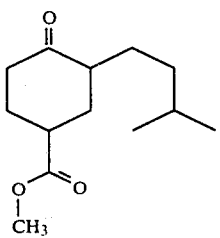

produced according to Example X.

Figure 32:
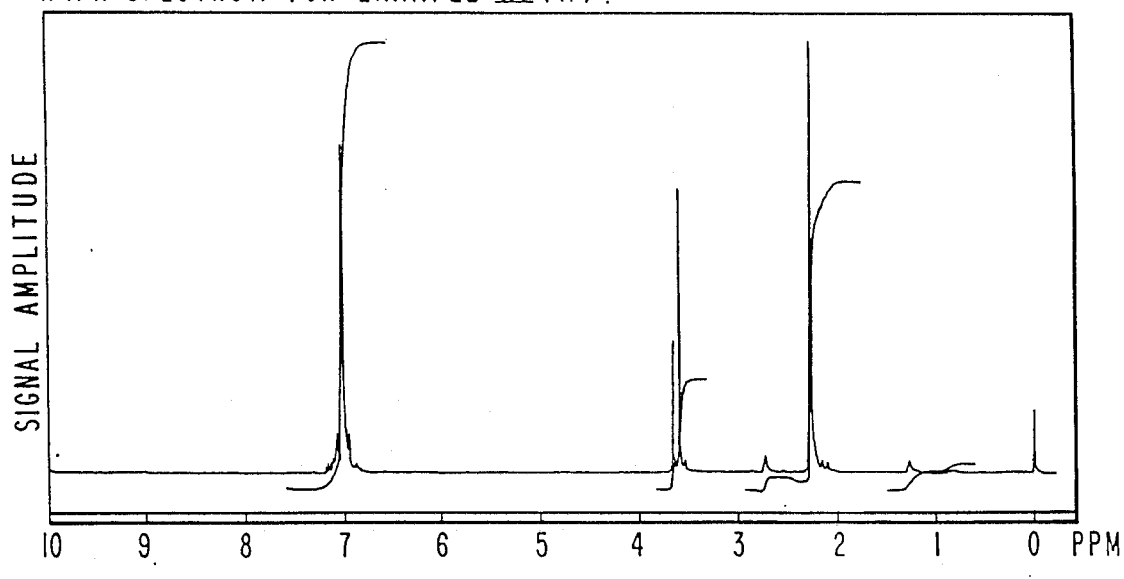

FIG. 32 is the NMR spectrum for the reaction product of Example XI(A) having the structure:

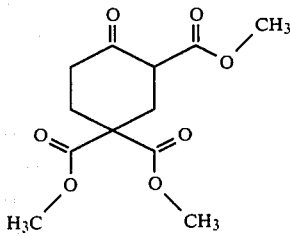

(conditions: Field strength: 100 MHz; Solvent: CFCl$_3$).

Figure 33:
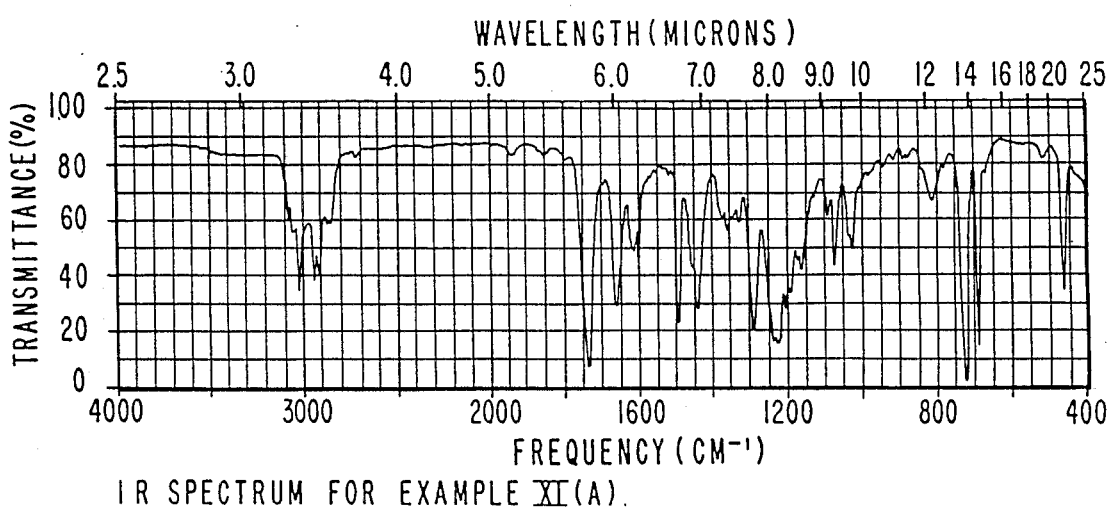

FIG. 33 is the infra-red spectrum for the compound having the structure:

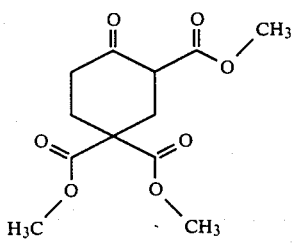

produced according to Example XI(A).

Figure 34:
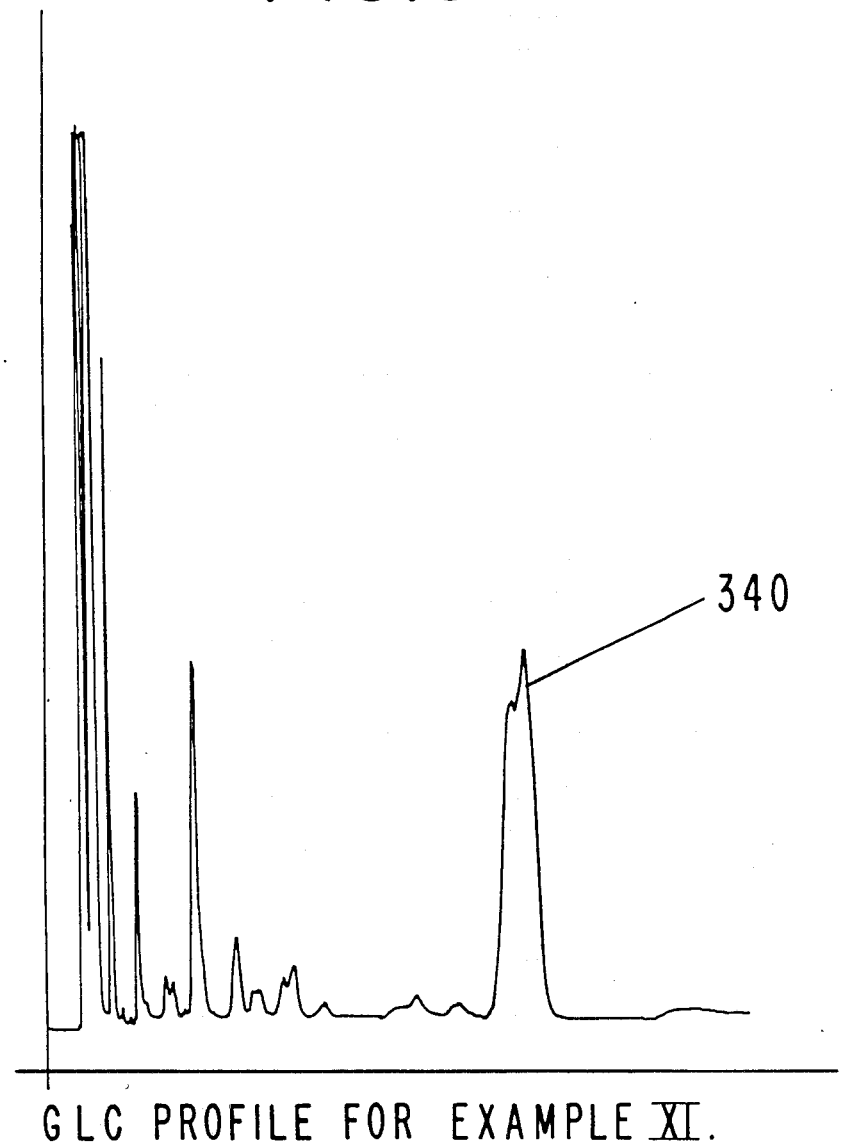

FIG. 34 is the GLC profile for the reaction product of Example XI(B) containing the compound having the structure:

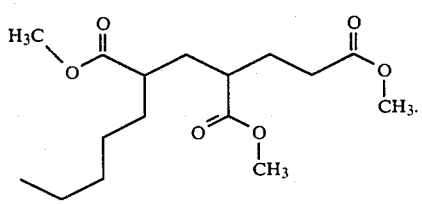

Figure 35:
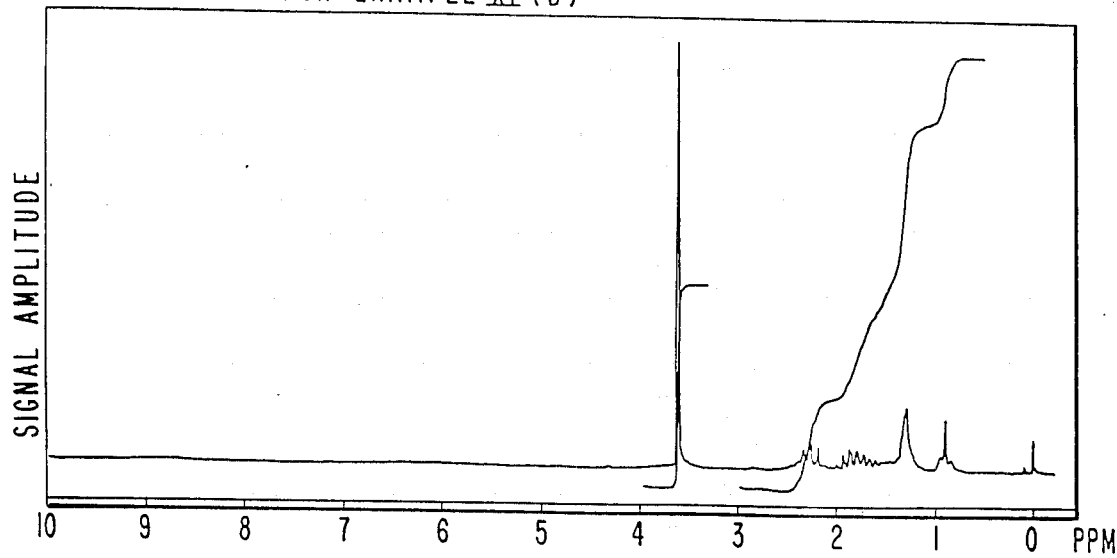

FIG. 35 is the NMR spectrum for the reaction product of Example XI(B) containing the compound having the structure:

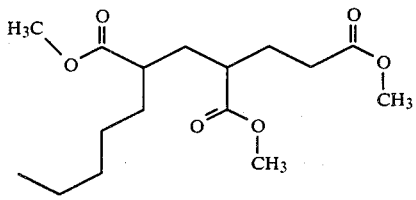

(conditions: Field strength: 100 MHz; Solvent: CFCl₃).

Figure 36:
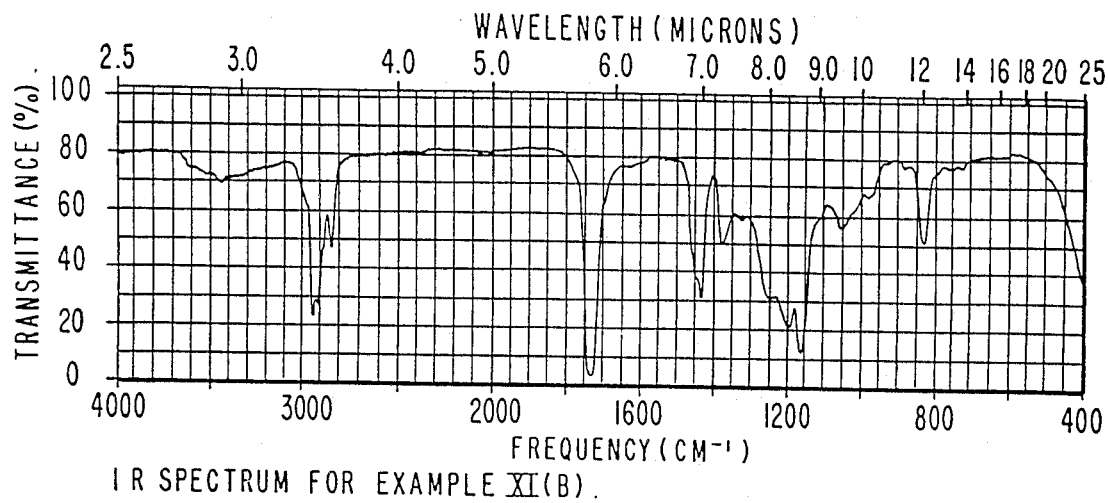

FIG. 36 is the infra-red spectrum for the compound having the structure:

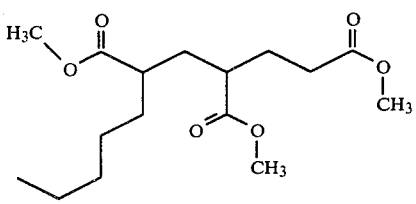

produced according to Example XI(B).

Figures 37, 38:
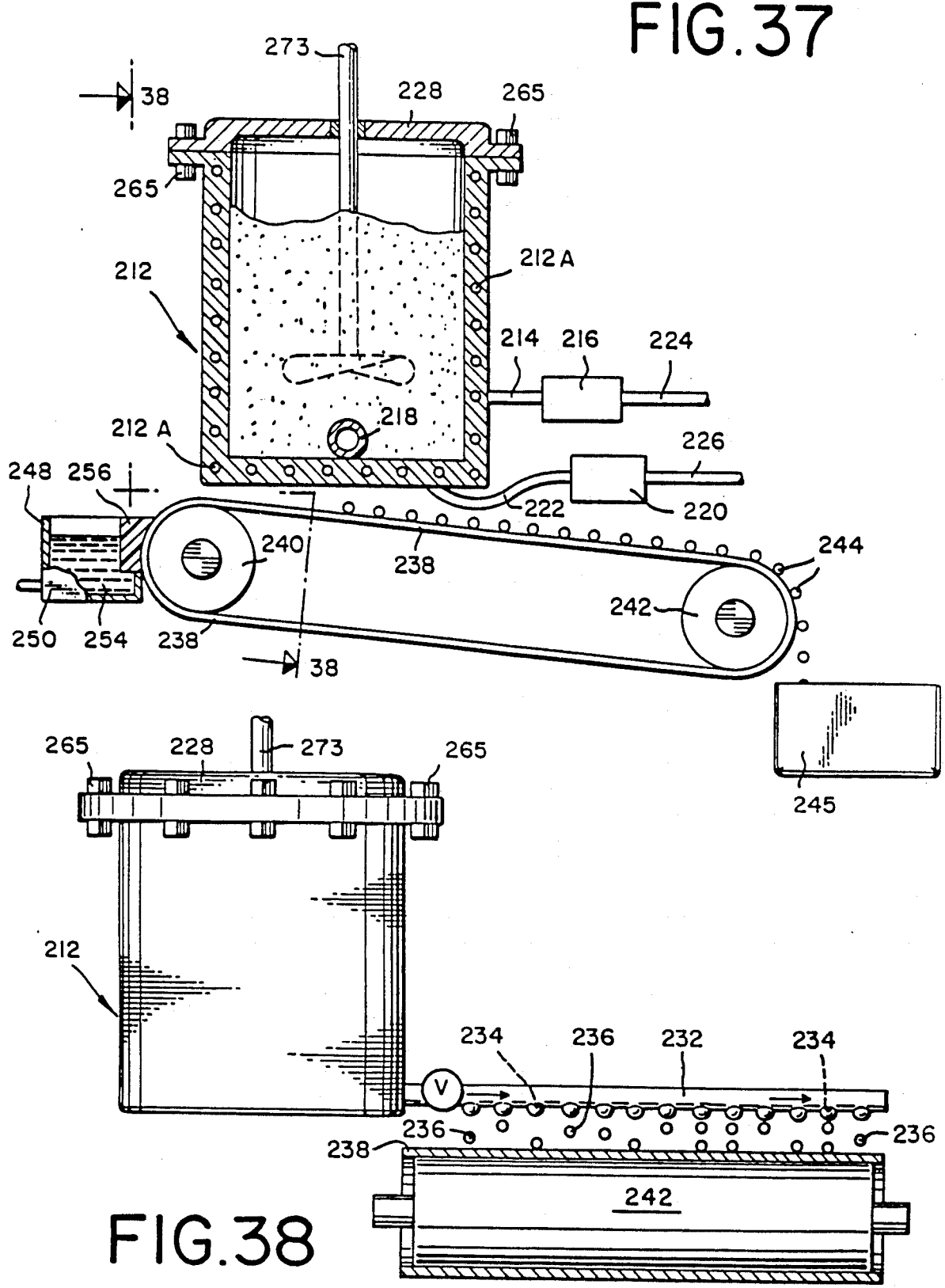

FIG. 37 is a partial side elevation and partial sectional view of an apparatus for forming polymer pellets scented with one of the perfume compositions or perfumery materials of our invention.

FIG. 38 is a section taken on line 38—38 of FIG. 37.

DETAILED DESCRIPTION OF THE DRAWINGS

FIG. 6 is the GLC profile for the reaction product of Example III containing the compound having the structure:

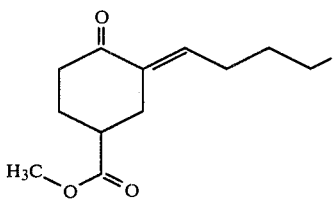

The peak indicated by reference numeral "60" is the peak for the compound having the structure:

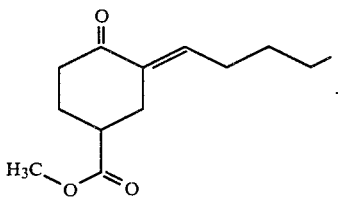

FIG. 7 is the GLC profile for the reaction product of Example III after hydrogenation containing the compound having the structure:

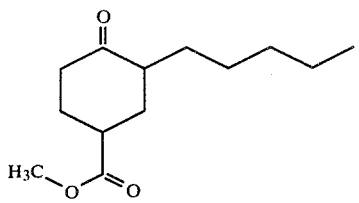

(conditions: SE-30 column programmed at 220° C. isothermal). The peak indicated by reference numeral "70" is the peak for the compound having the structure:

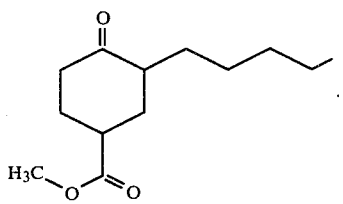

FIG. 8 is the GLC profile for the reaction product of Example IV containing the compound having the structure:

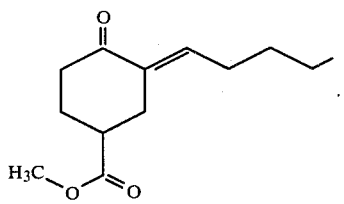

The peak indicated by reference numeral "80" is the peak for the compound having the structure:

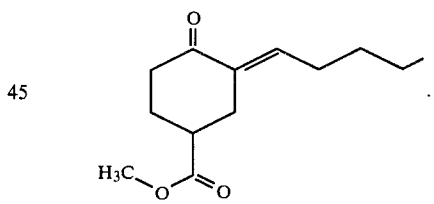

FIG. 9 is the GLC profile for the reaction product of Example IV after the hydrogenation step. The peak indicated by reference numeral "90" is the peak for the compound having the structure:

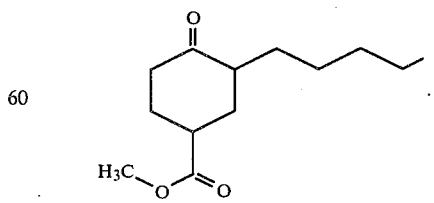

FIG. 12 is the GLC profile for the reaction product of Example V containing the compound having the structure:

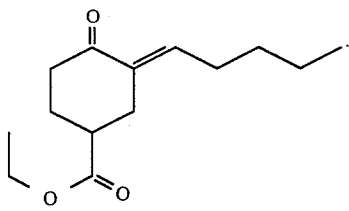

The peak indicated by reference numeral "121" is the peak for the compound having the structure:

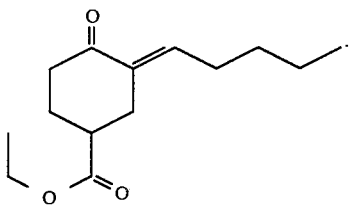

FIG. 13 is the GLC profile for the reaction product of Example V after hydrogenation containing the compound having the structure:

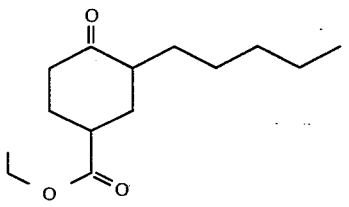

The peak indicated by reference numeral "130" is the peak for the compound having the structure:

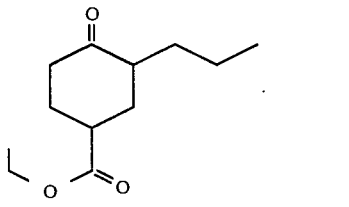

FIG. 18 is the GLC profile for the reaction product of Example VII containing the compound having the structure:

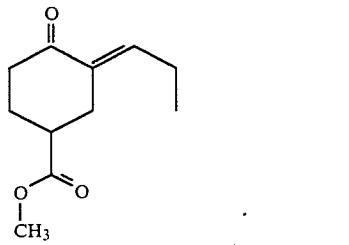

(conditions: 10% SE-30 column programmed at 180° C. isothermal). The peak indicated by reference numeral "180" is the peak for the compound having the structure:

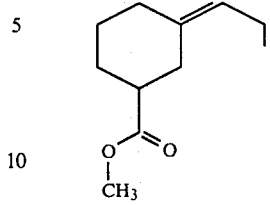

FIG. 19 is the GLC profile for the reaction product of Example VII after hydrogenation containing the compound having the structure:

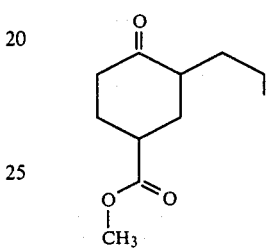

The peak indicated by reference numeral "190" is the peak for the compound having the structure:

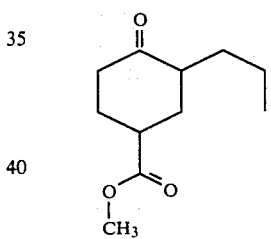

(Conditions: 10% SE-30 column programmed at 220° C. isothermal).

FIG. 22 is the GLC profile for the reaction product of Example VIII containing the compound having the structure:

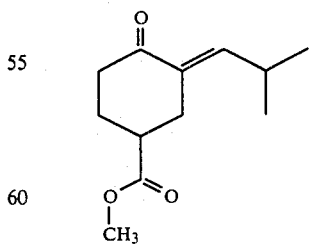

(conditions: 10% SE-30 column programmed at 180° C. isothermal). The peak indicated by reference numberal "220" is the peak for the compound having the structure:

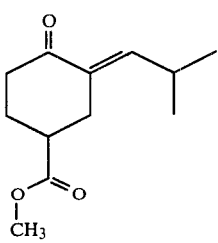

FIG. 23 is the GLC profile for the reaction product of Example VIII after hydrogenation containing the compound having the structure:

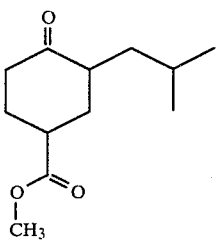

(conditions: 10% SE-30 column programmed at 220° C. isothermal). The peak indicated by reference numeral "230" is the peak for the compound having the structure:

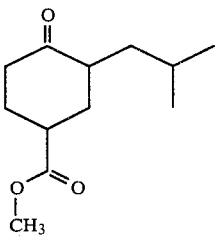

FIG. 26 is the GLC profile for the reaction product of Example IX containing the compound having the structure:

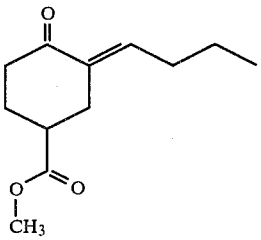

The peak indicated by reference numeral "260" is the peak for the compound having the structure:

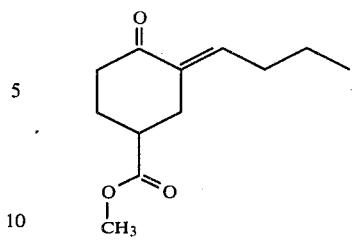

(conditions: 10% SE-30 column programmed at 180° C. isothermal).

FIG. 27 is the GLC profile for the reaction product of Example IX after hydrogenation containing the compound having the structure:

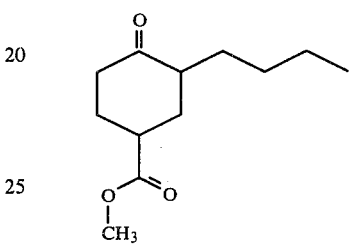

(Conditions: 10 SE-30 column programmed at 220° C. isothermal). The peak indicated by reference numeral "270" is the peak for the compound having the structure:

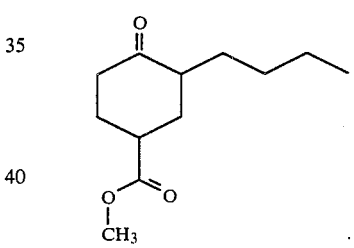

FIG. 34 is the GLC profile for the reaction product of Example XI(B) containing the compound having the structure:

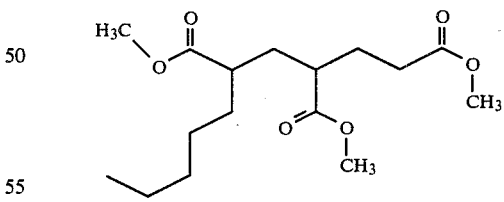

The peak indicated by reference numeral "340" is the peak for the compound having the structure:

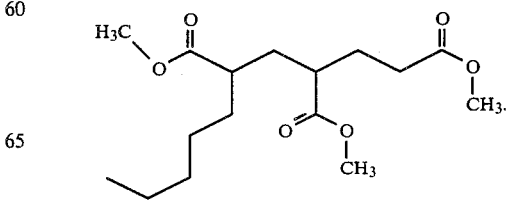

Referring to FIGS. 37 and 38, the apparatus used in producing polymeric fragrances containing the para-carboalkoxy cyclohexanones of our invention comprises a device for forming scented polyolefin (for example) pellets which comprises a vat or container 2101 into which a mixture of polyolefins such as polyethylene or an aromatic substance or scented material containing or consisting of the para-carboalkoxy cyclohexanones of our invention is placed. The container is closed by an air tight lid 228, and clamped to the container by bolts 265. A stirrer 273 traverses the lid or cover 228 in air tight manner and is rotated in a suitable manner. A surrounding cylinder 212 having heating coils which are supplied with electric current through cable 224 from a rheostat or control 216 is operated to maintain the temperature inside the container 2101 such that polyethylene or other thermoplastic polymer in the container will be maintained in the molten or liquid state. It has been found advantageous to employ a colorless, odorless polymer (e.g. polyethylene) with a viscosity ranging between 180 and 220 Saybolt seconds and having a melting point in the range of 200°–280° F. The heater 2201 is operated to maintain the upper portion of the container 2101 within a temperature range of from 250°–350° F. The bottom portion of the container 218 is heated by means of heating coils 222 heated through a control 2201 connected thereto through a connecting wire 226 to maintain the lower portion of the container 218 within a temperature range of from 250°–350° F.

Thus, polymer (e.g. polyolefin) added to the container 2101 is heated from 10–12 hours whereafter a scent or aroma imparting material which contains or consists of at least one of the para-carboalkoxy cyclohexanones of our invention is quickly added to the melt. The material must be compatible with the polyolefin and forms a homogeneous liquid melt therewith. The scented material containing or consisting of one of the para-carboalkoxy cyclohexanones of our invention is of a type for the particular aroma desired and formulated specifically for the scenting purpose for which the polyolefin will be employed. The heat resisting coils and aromatic materials in some instances in solid or powdered form may be employed and added to the polyolefin in the container 2101. Generally about 10–30% by weight of scenting material is added to the polyolefin.

After the scent imparting material containing or consisting of one of the para-carboalkoxy cyclohexanones of our invention is added to the container 2101, the mixture is stirred for a few minutes, for example, 5–15 minutes and maintained within the temperature ranges indicated previously by the heating coils 212 and 218, respectively. The controls 216 and 2201 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g. polyolefin) and aroma imparting mixture (containing or consisting of one of the para-carboalkoxy cyclohexanones of our invention) will continuously drop through the orifices 234 downwardly from the conduit 232. During this time, the temperature of the polymer (e.g. polyolefin) and aroma mixture containing or consisting of one of the para-carboalkoxy cyclohexanones of our invention in the container 2101 is accurately controlled so that a temperature in the range of from about 210°–275° F. will exist in the conduit 232. The regulation of the temperature through the control 216 and the control 2201 is essential in order to insure temperature balance to provide for the continuous dropping or dripping of molten polymer (e.g. polyolefin) and scenting material containing or consisting of one of the para-carboalkoxy cyclohexanones of our invention through the orifices 234 at a rate which will insure the formation of droplets 236 which will fall downwardly onto a moving conveyor belt 238 trained to run between conveyor wheels 2401 and 242 beneath the conduit 232.

When the droplets 236 fall onto the conveyor 238, they form pellets 244 which harden almost instantaneously and fall off the end of the conveyor 238 into a container 259 which is advantageously filled with water or some other suitable cooling liquid in order to insure the rapid cooling of each of the pellets. The pellets 244 are then collected from the container 259 and utilized in a process as illustrated infra.

A feature of this aspect of the process of our invention is in the provision for moistening the conveyor belt 238 to insure rapid formation of the solid polymer (e.g. polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 259 which is continuously fed with water 252 to maintain a level 254 for moistening a sponge element 256 which bears against the exterior surface of the belt 238.

THE INVENTION

The instant invention provides a compound defined according to the generic structure:

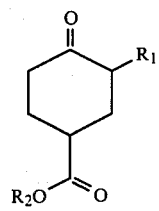

wherein R represents hydrogen or $C_1$–$C_7$ alkyl; and $R_2$ represents methyl or ethyl. The compounds are useful in augmenting or enhancing the aroma and/or taste of consumable materials including foodstuffs, chewing gums, toothpastes, medicinal products, chewing tobaccos, smoking tobaccos, smoking tobacco articles, perfume compositions, colognes and perfumed articles (including but not limited to solid or liquid anionic, cationic, nonionic or zwitterionic detergents, perfumed polymers, fabric softener compositions and fabric softener articles, cosmetic powders, hair preparations and the like).

Briefly, our invention contemplates augmenting or enhancing the aroma or taste of nutty, blueberry, raspberry, citrusy, caramel, maple, hazel-nut, cocoa and coffee flavored foodstuffs. Thus, the compounds defined according to the generic structure:

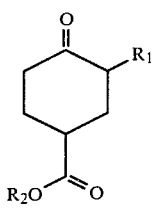

wherein $R_1$ represents hydrogen or $C_1$–$C_7$ alkyl and $R_2$ represents methyl or ethyl augment or enhance nutty, raspberry kernel-like, tarte unripened lime, bitter, lemony, caramel-like, maple sugar-like, maple/hazel-nut, meat, cocoa, coffee and fresh almond aroma and taste nuances in foodstuffs as set forth supra.

Briefly, our invention further contemplates augmenting or enhancing the aroma of perfume compositions, perfumed articles and colognes. Thus, the compound defined according to the genus:

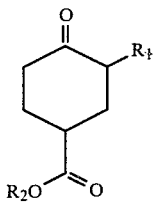

wherein $R_1$ represents hydrogen or $C_1$–$C_7$ alkyl and $R_2$ represents methyl or ethyl augment or enhance fruity, woody, strawberry-like, raspberry, green, fresh floral, jasmine-like, lemony, green, burnt maple, maple/nutty, meat/cocoa/coffee and valerian-like aromas with woody, ionone-like, sweet raspberry-like, licorice-like jasmine-like, citrusy, lemon, and toasted almond undertones.

The compounds of our invention defined according to the generic structure:

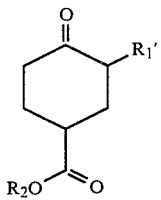

wherein $R_1'$ represents $C_4$–$C_7$ alkyl and $R_2$ represents methyl or ethyl are novel compounds.

The compounds of our invention defined according to the generic structure:

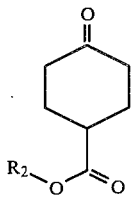

wherein $R_2$ represents methyl or ethyl may be produced by hydrogenation of the compound having the structure:

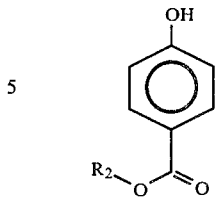

using a palladium catalyst at temperatures in the range of from about 130 up to about 170° C. and pressures in the range of from about 40 psig up to about 100 psig in accordance with the reaction:

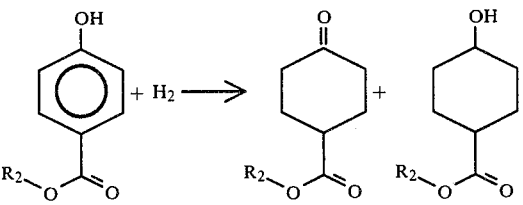

The compound having the structure:

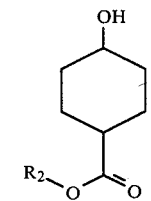

is produced as a byproduct and this genus of compounds also has valuable organoleptic utilities.

The compounds having the structure:

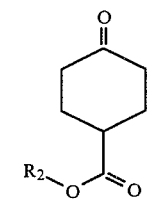

may be used for their organoleptic properties "as is" or they may be further reacted with an aldehyde defined according to the structure:

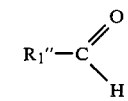

in order to form the compound having the structure:

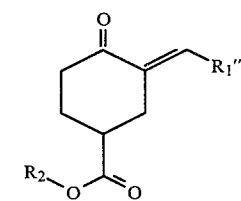

(in the presence of hydrogen chloride gas) and the compounds having the structure:

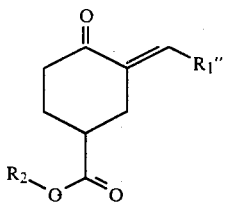

may then be hydrogenated in order to form compounds defined according to the genus having the structure:

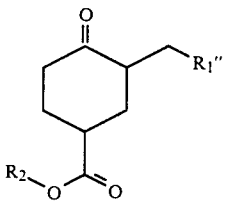

wherein $R_1''$ represents $C_1-C_6$ alkyl and $R_2$ represents methyl or ethyl. This sequence of reactions is as follows:

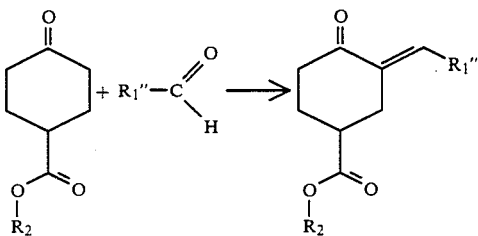

and

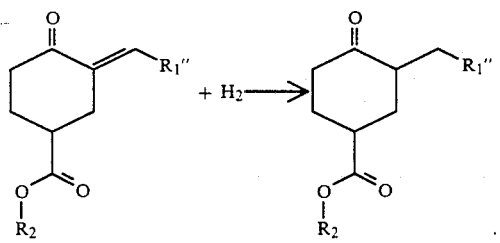

The reaction:

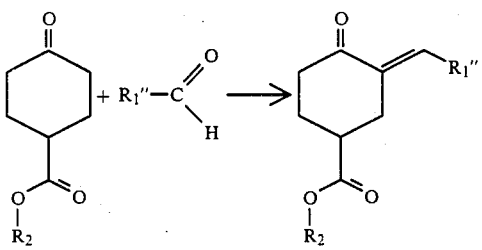

proceeds in the presence of hydrogen chloride gas at a temperature in the range of from about $-10°$ C. up to about $+10°$ C. and in the presence of a solvent inert to the reactants or products such as toluene or xylene. The mole ratio of aldehyde defined according to the structure:

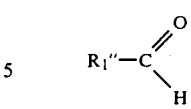

to ketone defined according to the structure:

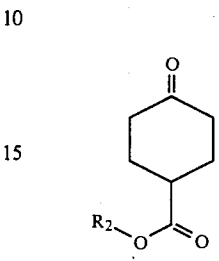

may vary from about 0.5:1.5 up to about 1.5:0.5 with a preferred mole ratio of about 1:1 being most expedient.

The reaction:

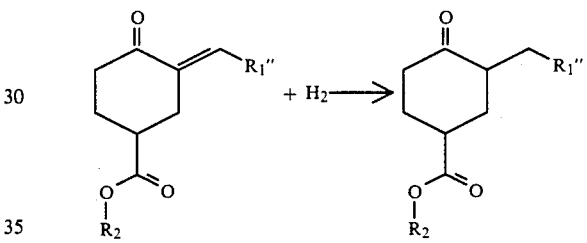

proceeds using a palladium on carbon or palladium on calcium carbonate catalyst, e.g., 10% palladium on carbon at a pressure in the range of 35 psig up to about 150 psig in the presence of an inert solvent such as isopropyl alcohol. At the end of the reaction, the reaction mass is distilled preferably using a fractional distillation column in order to yield the desired products.

The compounds of our invention defined according to the structure:

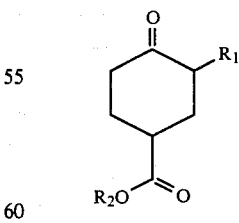

wherein $R_1$ represents $C_1-C_7$ alkyl and $R_2$ represents methyl or ethyl may also be prepared according to the process of Huffman and Sawdaye, Cynth. Comm. 11(12) 979-81 (1981), that is, according to the reaction sequence:

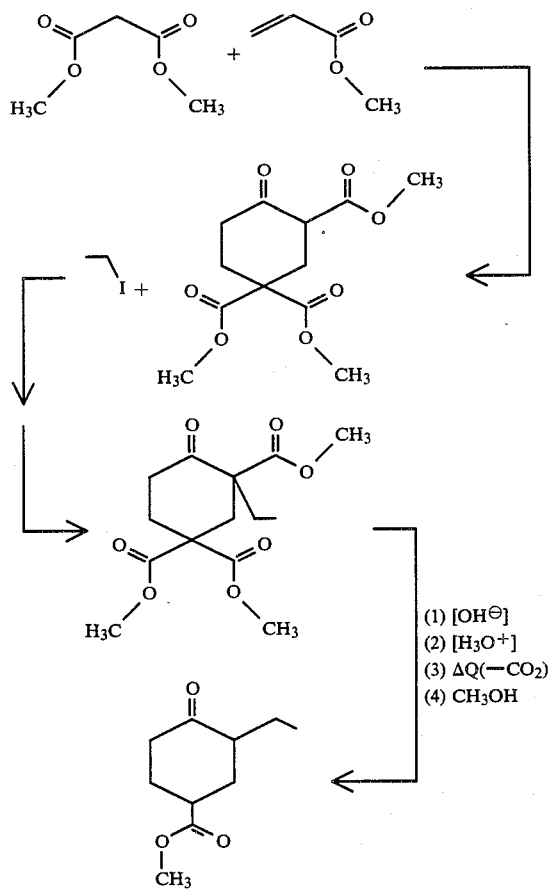

Thus, an alkyl acrylate having the structure:

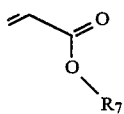

may be reacted with a malonic acid ester having the structure:

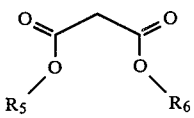

in order to form the cyclic keto triester having the structure:

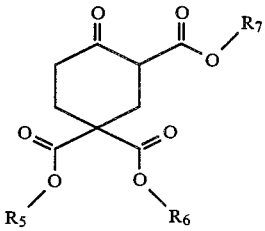

according to the reaction:

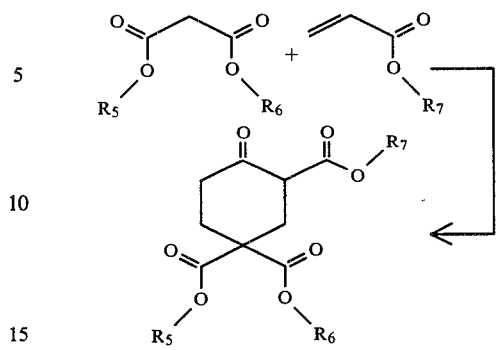

wherein $R_5$, $R_6$ and $R_7$ represent the same or different methyl or ethyl. The reaction is carried out in the presence of base such as sodium hydride or potassium hydride and in the presence of a solvent such as toluene, xylene or dimethylformanide or mixtures of same. The reaction is carried out at reflux temperatures for a period of between about two and about ten hours and at pressures of between one atmosphere and about four atmospheres. At the end of the reaction the reaction product defined according to the structure:

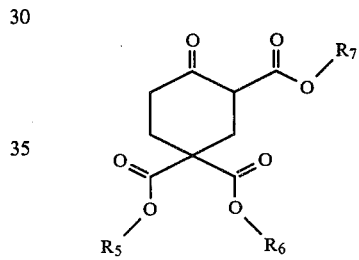

is distilled and further reacted with a $C_1$–$C_7$ alkyl halide defined according to the structure:

wherein X is chloro, bromo or iodo and $R_1$ is $C_1$–$C_7$ alkyl according to the reaction:

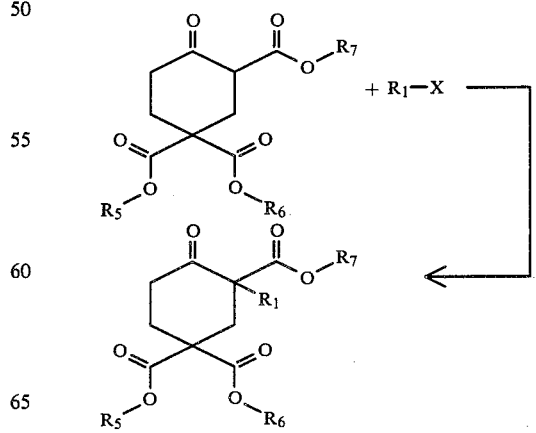

in order to form the compound having the structure:

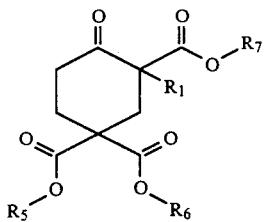

this reaction is carried out in a strong base such as potassium-t-butoxide in a compatible but inert solvent such as t-butanol. The reaction is also carried out at reflux conditions. The mole ratio of the compound having the structure:

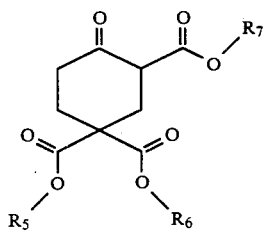

to the compound having the structure:

is about 1:1 with a slight excess of the compound having the structure:

being preferred. At the end of the reaction, the resulting compound having the structure:

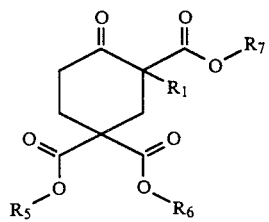

is decyclized and saponified using base followed by acid and the resulting product is decarboxylated to yield the tricarboxylic acid having the structure:

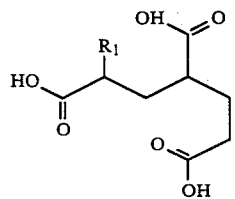

according to the reaction:

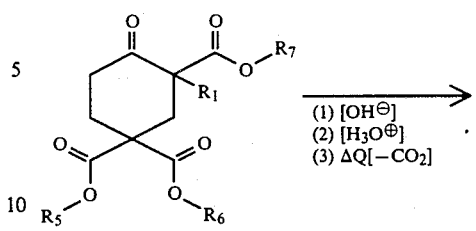

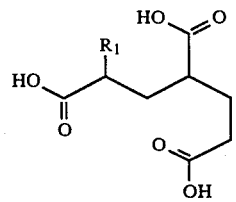

The saponification and decarboxylation are carried out according to standard saponification and decarboxylation conditions. The resulting triester having the structure:

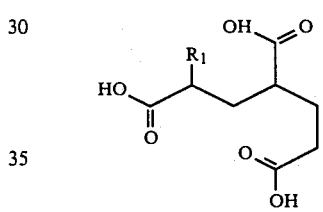

is then esterified with any desired alkanol such as methanol or ethanol having the structure:

according to the standard esterification reaction:

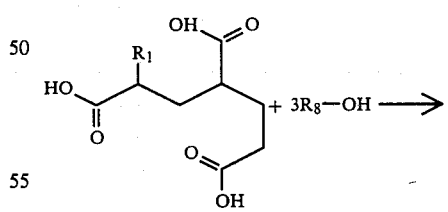

thereby yielding the triester having the structure:

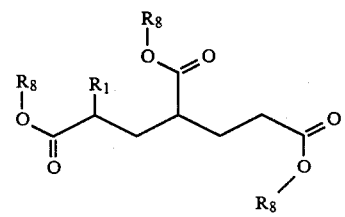

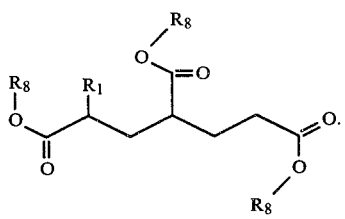

This triester is then cyclized according to the reaction:

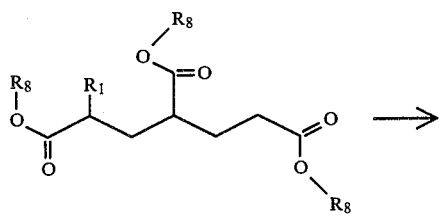

in the presence of base such as potassium-t-butoxide and solvent such as toluene, xylene, dimethylformanide or mixtures of same. This reaction takes place at reflux conditions and is operated in such a way as, during the reaction, the alkanol of reaction is distilled. At the end of the reaction, the reaction mass is decarboxylated according to the reaction:

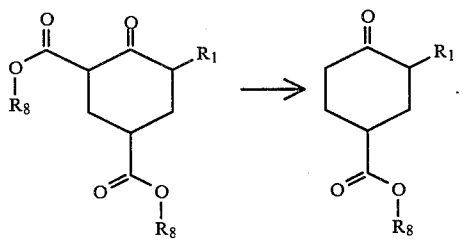

The decarboxylation reaction is carried out at temperatures of between about 200° and about 300° C. at pressures of from about 1 up to about 5 atmospheres. The reaction product having the structure:

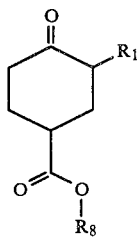

is then distilled using fractional distillation in order to yield organoleptically desirable product. $R_8$ can be methyl or ethyl and $R_1$ is $C_1$-$C_7$ alkyl.

The compound defined according to the structure:

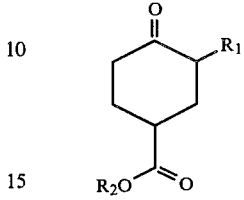

wherein $R_1$ is $C_1$-$C_7$ alkyl and $R_2$ is methyl or ethyl may also be produced by means of first reacting the compound defined according to the structure:

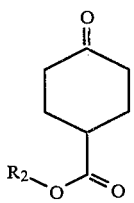

with a lithium dialkyl amide according to the reaction:

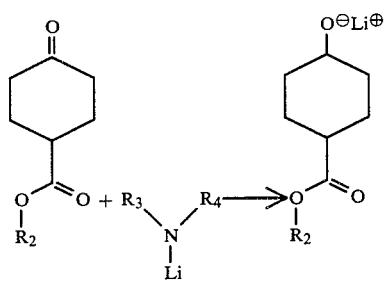

whereby the lithium salt having the structure:

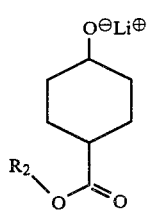

is produced (wherein $R_3$ and $R_4$ are the same or different and each represents $C_1$-$C_4$ alkyl). This reaction is carried out in the presence of an inert solvent such as tetrahydrofuran at temperatures in the range of $-80°$ up to $-20°$ C. The resulting lithium salt having the structure:

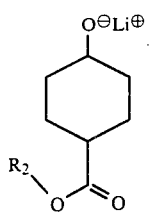

is then reacted with an alkyl halide such as ethyl iodide defined according to the structure:

$R_1-X$ wherein $R_1$ is $C_1-C_7$ alkyl and X is chloro, bormo or iodo according to the reaction:

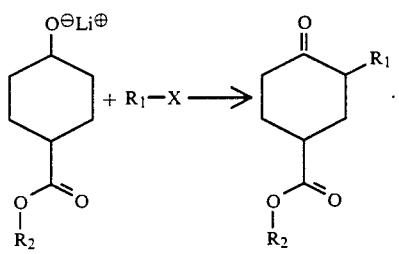

The second reaction:

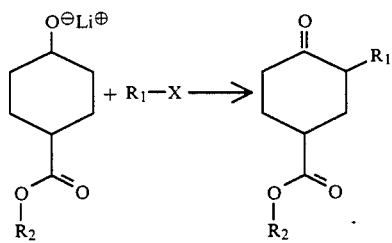

is carried out "in situ" without isolation of the lithium salt having the structure:

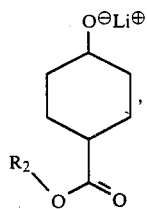

preferably and is carried out under the same range of reaction conditions as the first reaction.

In each of the reactions the mole ratios of reactants are preferably about 1:1. Thus, the mole ratio of compound defined according to the structure:

$R_1-X$ to lithium salt having the structure:

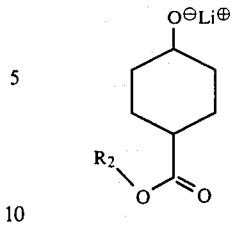

is about 1:1 and the mole ratio of lithium dialkyl amide to the compound defined according to the structure:

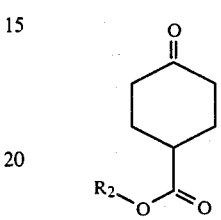

is also about 1:1.

At the end of the reaction, as stated supra, the reaction product is extracted from the reaction mass or the reaction mass is washed, for example, with saturated sodium chloride. The reaction product is then distilled, preferably by means of vacuum distillation using a fractionation column.

Examples of the products of our invention and their organoleptic properties as produced by means of one of the foregoing processes are as follows:

TABLE I

| Structure of Compound | Food Flavor Properties | Perfumery Properties |
|---|---|---|
| Compound having the structure: [structure with H₃CO] produced according to Example I. | A nutty aroma and taste with a blueberry flavor at 20 ppm. | A fruity and woody aroma with woody and ionone-like nuances on dry-out. |
| Compound having the structure: [structure] produced according to Example II. | A raspberry kernel aroma and taste at 1 ppm. | A strawberry-like, raspberry-like, and green aroma with sweet raspberry-like and licorice nuances on dry-out. |
| Compound having the structure: [structure with H₃C] produced according to Example III and IV. | A tart, unripened lime aroma and taste at 4 ppm. | A fresh floral, jasmine-like and lemony aroma with jasmine-like and citrusy (lemon) nuances. |

TABLE I-continued

| Structure of Compound | Food Flavor Properties | Perfumery Properties |
|---|---|---|
| Compound having the structure: 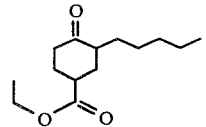 produced according to Example V. | A bitter lemon aroma and taste profile at 8 ppm. | A jasmine-like aroma with citrusy undertones. |
| Compound having the structure: 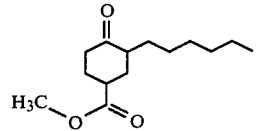 produced according to Example VI. | A dry lime citrusy aroma and taste profile at 3 ppm. | An intense jasmine, green aroma profile. |
| Compound having the structure: 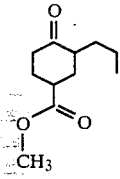 produced according to Example VII. | A caramel-like, maple sugar-like, aroma and taste profile at 2 ppm. | A burnt maple aroma profile. |
| Compound having the structure: 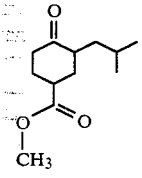 produced according to Example VIII. | A maple/hazelnut aroma and taste profile at 5 ppm. | A maple/nutty aroma. |
| Compound having the structure: 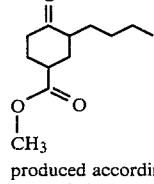 produced according to Example IX. | An intense cocoa aroma and taste profile with coffee nuances at 1 ppm. | A meaty, cocoa and coffee aroma profile. |
| Compound having the structure: 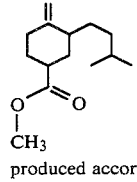 produced according to Example X. | A fresh almond aroma and taste profile at 10 ppm. | A valerian-like, green aroma with a toasted almond undertone. |

When one of the alkyl substituted and unsubstituted para-carboalkoxy cyclohexanones of our invention is used as food flavor adjuvant, the nature of the coingredients included with one of the alkyl substituted and unsubstituted para-carboalkoxy cyclohexanones in formulating the product composition will also serve to alter, modify, augment or enhance their organoleptic characteristics of the ultimate foodstuff treated therewith.

As used herein in regard to flavors, the term "alter", "modify" and "augment" in their various forms mean "supplying or imparting flavor character or note to otherwise bland, relatively tasteless substances or augmenting the existing flavor characteristic where the natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancment" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizes, thickeners, surface active agents, conditioners, other flavorants and flavor intensifiers.

Stabilizer compounds include preservatives, e.g., sodium chloride; antioxidants, e.g, calcium and sodium ascorbate, ascorbic acid, butylated hydroxy-anisole (mixture of 2- and 3-tertiary-butyl 4-hydroxy anisole), butylated hydroxy toluene (2,5-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disacchardies, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonte, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetaoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazines tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with alkyl substituted and unsubstituted para-carboalkoxy cyclohexanones of our invention by not covering or spoiling the organoleptic properties (aroma and/or taste) thereof; (ii) be non-reactive with the alkyl substituted and unsubstituted para-carboalkoxy cyclohexanones of our invention; and (iii) be capable of providing an environment in which the alkyl substituted and unsubstituted para-carboalkoxy cyclohexanones of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of alkyl substituted and unsubstituted para-carboalkoxy cyclohexanones employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of alkyl substituted and unsubstituted para-carboalkoxy cyclohexanones will, of course, substantially vitiate any possibility of obtaining the desired results while excess quantities prove needlessly costly and in extreme cases, may disrupt the flavor aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of alkyl substituted and unsubstituted para-carboalkoxy cyclohexanones ranging from a small but effective amount, e.g., 0.5 ppm up to about 100 ppm based on total composition are suitable. Concentrations in excess of the maximum quantity stated are not normally recommended, since they fail to prove commensurate enhancement of organoleptic properties. In those instances, wherein the alkyl substituted and unsubstituted para-carboalkoxy cyclohexanones is added to the foodstuff as an integral component of a flavoring composition, it is, of course, essential that the total quantity of flavoring composition employed be sufficient to yield an effective concentration of the alkyl substituted and unsubstituted para-carboalkoxy cyclohexanones in the foodstuff product.

Food flavoring compositions prepared in accordance with the present invention preferably contain the alkyl substituted and unsubstituted para-carboalkoxy cyclohexanones in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the alkyl substituted and unsubstituted para-carboalkoxy cyclohexanones with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the alkyl substituted and unsubstituted para-carboalkoxy cyclohexanones in a dry blender until the requisite degree of uniformity is achieved.

It is presently preferred to combine with the alkyl substituted and unsubstituted para-carboalkoxy cyclohexanones of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-updecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,2,6-trimethylcyclohex-1-ene);
β-Damascenone (1-crotonyl-2,2,6-trimethylcyclohexa-1,3-diene);
Beta-cyclohomocitral (2,2,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl)norbornadiene.

The alkyl substituted and unsubstituted para-carboalkoxy cyclohexanones and one or more auxiliary perfume ingredients, including for example, alcohols, aldehydes, ketones other than the alkyl substituted and unsubstituted para-carboalkoxy cyclohexanones of our invention, terpinic hydrocarbons, nitriles, esters other than the alkyl substituted and unsubstituted para-carboalkoxy cyclohexanones of our invention, lactones, natural essential oils and synthetic essential oils, may be admixed so that the combined odors of the individual components produce a pleasant and desired fragrance, particularly and preferably in jasmine and rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, at least one of the alkyl substituted and unsubstituted para-carboalkoxy cyclohexanones of our invention can be used to alter, modify or enhance the aroma characteristics of a perfume composition, for example, by utilizing or moderating the olfactory reaction contributed by another ingredient in the composition.

The amount of one or more of the alkyl substituted and unsubstituted para-carboalkoxy cyclohexanones of our invention which will be effective in perfume compositions as well as in perfumed articles and colognes depends on many factors, including the other ingredients, their amounts and the effects which are desired. It has been found that perfume compositions containing as little as 0.01% of at least one of the alkyl substituted and unsubstituted para-carboalkoxy cyclohexanones of our invention or even less (e.g., 0.005%) can be used to impart, augment or enhance fruity, woody, strawberry, raspberry, green, fresh floral, jasmine-like, lemony, burnt maple, maple/nutty, meat/cocoa/coffee and valerian-like aromas with woody, ionone-like, sweet raspberry-like, licorice-like, jasmine-like, citrusy, lemon and toasted almond undertones to soaps, cosmetics, solid or liquid anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the alkyl substituted and unsubstituted para-carboalkoxy cyclohexanones of our invention are useful [taken alone or together with other ingredients in perfume compositions] as (an) olfactory component(s) in detergents and soaps, space odorants and deodorants, perfumes, colognes, toilet water, bath preparations, such as creams, deodorants, hand lotions and sun screens; powders such as talcs, dusting powders, face powders and the like. When used as (an) olfactory component(s) as little as 1% of the at least one of the alkyl substituted and unsubstituted para-carboalkoxy cyclohexanones of our invention or even less will suffice to impart intense fruity, woody, strawberry-like, raspberry-like, green, fresh floral, jasmine-like, lemony, burnt maple, maple/nutty, meat, cocoa, coffee-like, and valerian-like aromas with woody, ionone-like, sweet raspberry-like, licorice-like, jasmine-like, citrusy, lemony, and toasted almond undertones to rose formulations and jasmine formulations. Generally, no more than 20% of at least one of the alkyl substituted and unsubstituted paracarboalkoxy cyclohexanones of our invention based on the ultimate end product is required in the perfume composition.

Accordingly, in perfume compositions and colognes from about 0.01% up to about 70% of the perfume composition may be at least one of the alkyl substituted and unsubstituted paracarboalkoxy cyclohexanones of our invention. In perfumed articles, the quantity of at least one of the alkyl substituted and unsubstituted para-carboalkoxy cyclohexanones of our invention in the perfumed article may vary from about 0.005% up to about 25% of the perfumed article in the case of perfumed polymers, for example, and up to about 8% in the case of solid or liquid anionic, cationic, nonionic or zwitterionic detergents, for example.

In addition, the perfume composition or fragrance composition of our invention can contain a vehicle, or carrier for at least one of the alkyl substituted and unsubstituted para-carboalkoxy cyclohexanones of our invention. The vehicle can be a liquid such as a non-toxic alcohol, such as ethyl alcohol or a non-toxic glycol, such as propylene glycol or the like. The carrier can also be an absorbent solid, such as a gum (e.g., gum arabic xanthan gum, or guar gum or mixtures of same) or components for encapsulating the composition (such as gelatin or by means of coacervation or such as a ureaformaldehyde prepolymer when such a polymeric wall is formed around a liquid perfume composition center).

Furthermore, one or more of the alkyl substituted and unsubstituted para-carboalkoxy cyclohexanones of our invention are capable of supplying and/or potentiating certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor, as well as methods of making the same which overcome specific problems heretofore encountered in which specific desired floral, musty, hay-tea-like, sweet and fruity aroma and taste nuances thereof, are created or enhanced and may be readily controlled and maintained at the desired uniform level regardless of variations in the tobacco components of the blend.

This invention further provides improved tobacco additives and methods whereby various floral, musty, hay-tea-like, sweet and fruity notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient at least one of the alkyl substituted and unsubstituted para-carboalkoxy cyclohexanones of our invention.

In addition to at least one of the alkyl substituted and unsubstituted para-carboalkoxy cyclohexanones of our invention, other flavoring and aroma additives may be added to the smoking tobacco materials or substitute therefor either separately or in mixture with at least one of the alkyl substituted and unsubstituted para-carboalkoxy cyclohexanones of our invention, other flavoring and aroma additives may be added to the smoking tobacco materials or substitute therefor either separately or in mixture with at least one of the alkyl substituted and unsubtituted para-carboalkoxy cyclohexanones as follows:

(i) Synthetic Materials:
Beta-ethyl-cinnamaldehyde;
Beta-cyclohomocitral;
Eugenol;
Dipentene;
Damascenone;
Damascone;
Maltol;
Ethyl Maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2-6,Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho-[2,1,b]-furan;
4-Hydroxy hexanoic acid, gamma lactone; and
Polyisoprenoid hydrocarbons defined in Example V of U.S. Pat. No. 3,589,372 issued on June 29, 1971.
(ii) Natural Oils;
Celery seed Oil;
Coffee extract;
Bergamot Oil;
Cocoa extract;
Nutmeg Oil;

Origanum Oil.

An aroma and flavoring concentrate containing at least one of the alkyl substituted and unsubstituted para-carboalkoxy cyclohexanones of our invention and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of at least one of the alkyl substituted and unsubstituted para-carboalkoxy cyclohexanones of our invention to smoking tobacco material is between 250 ppm and 1,500 ppm (0.025%–0.15%) of the active ingredients to the smoking tobacco material. We have further found that satisfactory results are obtained if the proportion by weight of the sum total of at least one of the alkyl substituted and unsubstituted para-carboalkoxy cyclohexanones of our invention and less than 50% used to flavoring material is between 2,500 and 15,000 ppm (0.25%–1.5%).

Any convenient method for incorporating at least one of the alkyl substituted and unsubstituted para-carboalkoxy cyclohexanones of our invention in the tobacco product may be employed. Thus, at least one of the alkyl substituted and unsubstituted para-carboalkoxy cyclohexanones of our invention taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material may be dipped into such solution. Under certain circumstances, a solution of at least one of the alkyl substituted and unsubstituted para-carboalkoxy cyclohexanones of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have at least one of the alkyl substituted and unsubstituted para-carboalkoxy cyclohexanones of our invention in excess of the amounts or concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of the compound having the structure:

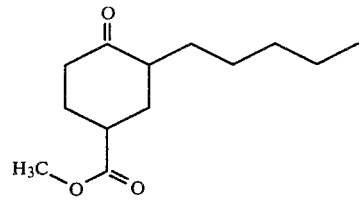

produced according to Example III or IV, infra, in an amount to provide a tobacco composition containing 800 ppm by weight of the compound having the structure:

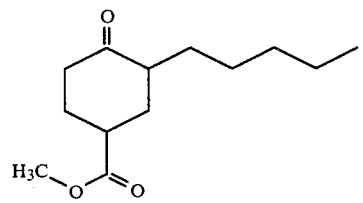

on a dry basis. Thereafter, the alcohol is removed by evaporation and the tobacco is manufactured into cigarettes by the usual techniques. The cigarette when treated as indicated has a desired and pleasing aroma (increased smoke body sensation in the mouth with enhanced tobacco-like notes and pleasant aromatic nuances) which is detectable in the main and side streams when the cigarette is smoked. This aroma is described as having floral, musty, hay-tea-like, sweet and fruity note.

While our invention is particularly useful in the manufacture of smoking tobacco, such as cigarette tobacco, cigar tobacco and pipe tobacco, other tobacco products formed from sheeted tobacco dust or fines may also be used. Likewise, at least one of the alkyl substituted and unsubstituted paracarboalkoxy cyclohexanones of our invention can be incorporated with materials such as filter tip materials, seam paste, packaging materials and the like which are used along with tobacco to form a product adapted for smoking. Furthermore, at least one of the alkyl substituted and unsubstituted paracarboalkoxy cyclohexanones of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following Examples I–XII serve to illustrate the processes for preparing the compounds of our invention and compounds useful for their organoleptic properties. Examples following Examples XII (Examples XIII, et seq) illustrate organoleptic utilities of the alkyl substituted and unsubstituted para-carboalkoxy cyclohexanones of our invention.

All parts and percentages given herein are by weight unless otherwise specified.

EXAMPLE I

PREPARATION OF 4-CARBOMETHOXY CYCLOHEXANONE

Reaction:

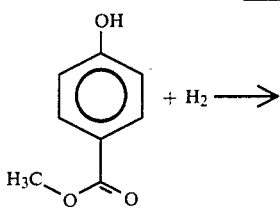

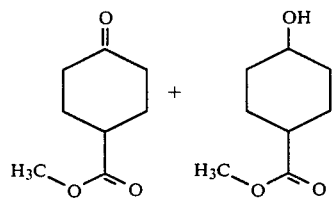

Into a 1-liter magnetically stirred autoclave is placed 488 grams of methyl-p-hydroxy benzoate having the structure:

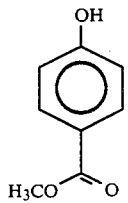

and 2.5 grams of 5% palladium on carbon catalyst. The autoclave is sealed and hydrogen is pumped in while maintaining the contents of the autoclave at 125°–130° C. and 50–70 psig pressure. After eighteen hours a GLC profile indicates that the reaction product contains 66% ketone having the structure:

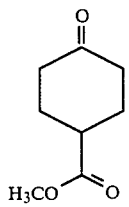

31% alcohol having the structure:

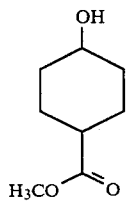

and 2% starting material having the structure:

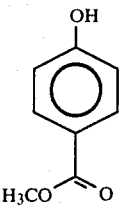

(conditions: 10% 10'×0.25" carbowax column programmed at 225° C. isothermal).

In an additional example the reaction proceeds in a much lesser period of timer increasing the amount of catalyst and running the reaction at a higher temperature.

The reaction mass is then cooled, filtered and distilled through an eight plate vigreux column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 87 | 123 | 3.4/2.8 | 178.9 |
| 2 | 85 | 143 | 2.3 | 72.1 |
| 3 | 87 | 138 | 2.3 | 37.4 |
| 4 | 87 | 141 | 2.3 | 15.0 |
| 5 | 91 | 146 | 2.3 | 16.1 |
| 6 | 92 | 163 | 2.3 | 47.0 |
| 7 | 93 | 176 | 2.3 | 36.1 |
| 8 | 104 | 198 | 2.3 | 11.4 |

Fractions 13–16 are substantially all ketone having the structure:

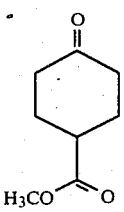

Fractions 25–27 are substantially all alcohol having the structure:

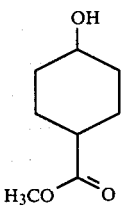

Figure 1:
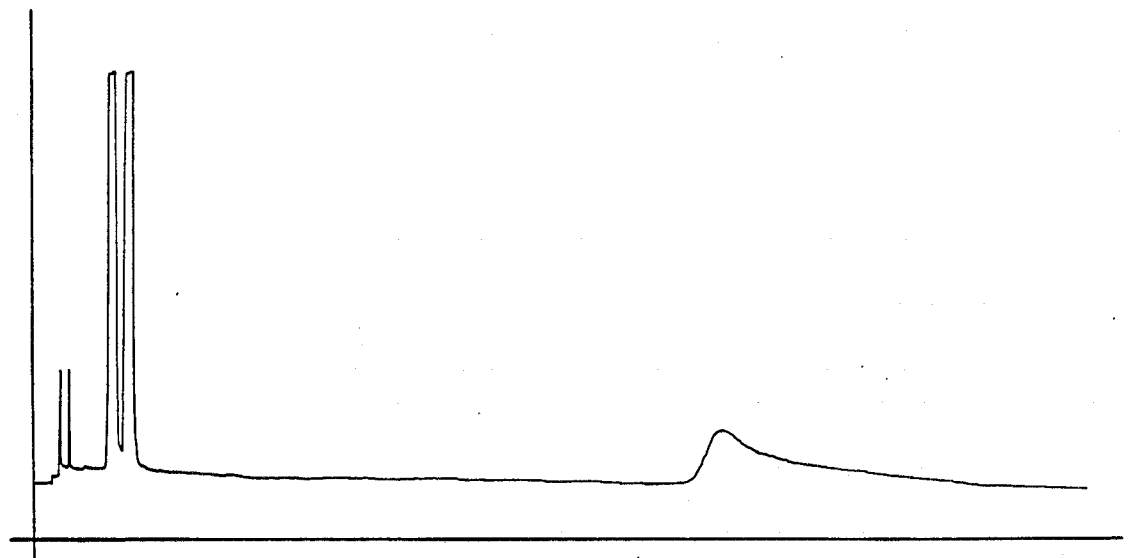
FIG. 1 is the GLC profile for the reaction product of Example I containing the compound having the structure.

FIG. 1 is the GLC profile of the crude reaction product prior to distillation. (Conditions: 10% carbowax 10'×0.25" column programmed at 225° C., isothermal).

FIG. 2 is the infra-red spectrum for Fraction 4 of the foregoing distillation containing the compound having the structure:

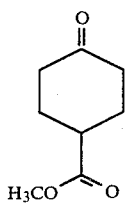

FIG. 3 is the NMR spectrum for Fraction of the foregoing distillation product. (Conditions: Field strength: 100 MHz; Solvent: CFCl₃).

The resulting compounds defined according to the structure:

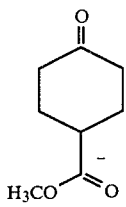

has a fruity and woody perfume aroma profile with woody and ionone-like nuances on dry-out. From a food flavor standpoint, it has a nutty aroma and taste with a blueberry flavor at 20 ppm.

EXAMPLE II

PREPARATION OF 4-CARBOETHOXYCYCLOHEXANONE

Reaction:

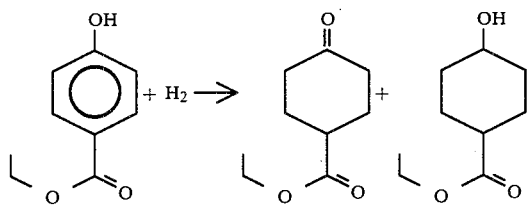

Into a 1-liter magnetically stirred autoclave is placed 489 grams of ethyl-p-hydroxybenzoate having the structure:

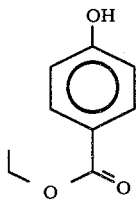

and 5% palladium on carbon catalyst (4 grams). The autoclave is sealed and hydrogenated at 125°–140° C. and 50 psig hydrogen pressure until the uptake of hydrogen is approximately 70% of theory. GLC analysis indicates that the reaction product at this point contains 71% ketone having the structure:

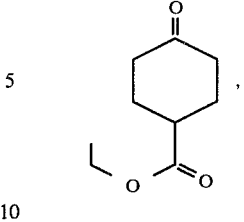

7.6% alcohol having the structure:

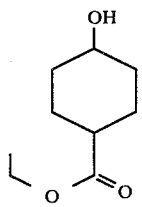

and 20% starting material having the structure:

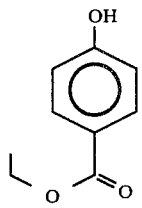

The hydrogenation is carried during a period of ten hours (GLC conditions: 10′×0.125″ 10% carbowax column programmed at 225° C., isothermal).

At the end of the ten hour period, the autoclave is cooled and the reaction product is diluted with isopropyl alcohol and filtered. The isopropyl alcohol is then removed by means of stripping and the remainder of the reaction mass is then distilled through a short past column to separate the resulting ketone and alcohol from the starting material (boiling point: 2.4 mm/Hg at 90°–118° C.)

The ketone and alcohol cannot be separated by distillation. Accordingly, the alcohol having the structure:

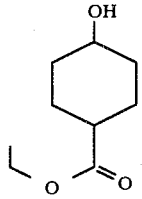

is converted to the corresponding proprionate ester by means of stirring with 75 grams of proprionic anhydride at 100° C. for a period of four hours, washing the residue and distilling the resulting product through an eight plate vigreux column yielding the following fractions:

| Fraction No. | Vapor Temp. (°C.) | Liquid Temp. (°C.) | Vacuum mm/Hg. Pressure | Weight of Fraction (gms) |
| --- | --- | --- | --- | --- |
| 1–2 | 72–78 | 120/126 | 2.4 | 20.9 |
| 3–6 | 82–84 | 124 | 2.5 | 67.3 |
| 7–9 | 84 | 124–130 | 2.5 | 97.6 |

| Fraction No. | Vapor Temp. (°C.) | Liquid Temp. (°C.) | Vacuum mm/Hg. Pressure | Weight of Fraction (gms) |
|---|---|---|---|---|
| 10-11 | 84-105 | 130-153 | 2.5 | 36.7 |
| 12 | 105 | 153 | 2.5 | 12.2 |
| 13-14 | 105-108 | 158-184 | 2.5 | 17.6 |
| 15-16 | 115 | 220 | 2.5 | 10.1 |

Fractions 3-12 of the foregoing distillation are substantially pure ketone having the structure:

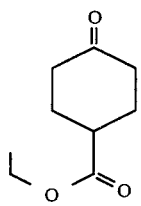

Fractions 13-16 of the foregoing distillation is substantially pure proprionate ester of the alcohol having the structure:

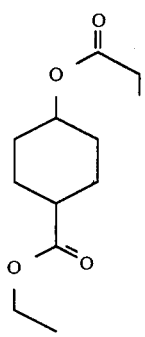

FIG. 4 is the NMR spectrum for Fraction 7 of the foregoing distillation containing the compound having the structure:

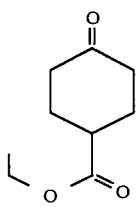

(conditions: Field strength: 100 MHz; Solvent: CFCl₃).

FIG. 5 is the infra-red spectrum for Fraction 7 of the foregoing distillation containing the compound having the structure:

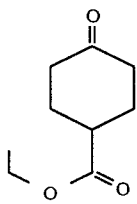

The compound having the structure:

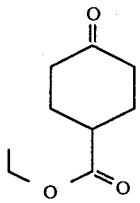

from a perfumery standpoint has a strawberry-like, raspberry-like and green aroma with sweet raspberry-like and licorice nuances on dry-out. From a flavor standpoint it has an excellent raspberry kernel aroma and taste profile at 1 ppm.

EXAMPLE III

PREPARATION OF 4-OXO-3-N-PENTYL-CYCLOHEXANE CARBOXYLIC ACID, METHYL ESTER

Reaction:

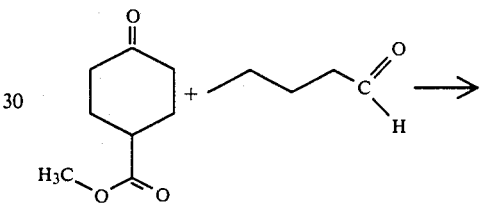

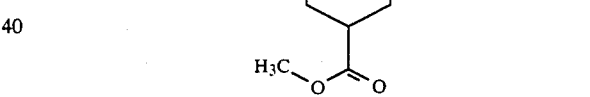

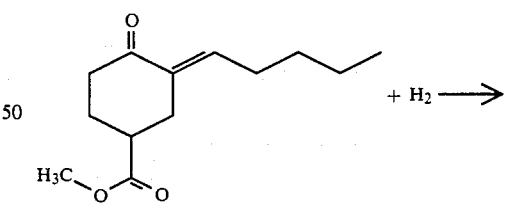

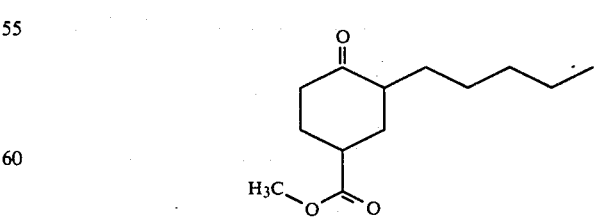

Into a 300 cc reaction vessel equipped with stirrer, thermometer, reflux condenser and inlet hydrogen chloride gas tube is placed a mixture of 40 ml toluene and 15.6 grams of keto ester having the structure:

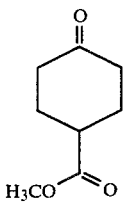

the reaction mass is cooled to 0° C. and is saturated with hydrogen chloride gas. 5 Grams of crystalline sodium sulfate is then added to the reaction mass with stirring. Over a period of one hour while maintaining the reaction mass at 5°–10° C., a mixture of 40 ml toluene and 17.2 grams of valeraldehyde is added. At the end of the one hour period, the reaction mass is permitted to warm up to room temperature. The reaction mass is then stirred for a period of three hours. The reaction mass is then distilled on a one plate column yielding the compound having the structure:

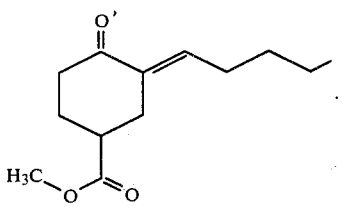

The resulting reaction product having the structure:

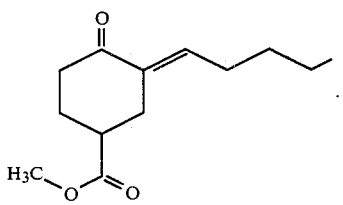

The resulting product has a GLC profile as illustrated in FIG. 6 (conditions: 220° C. SE-30 isothermal). The peak indicated by reference numeral "60" is the peak for the compound having the structure:

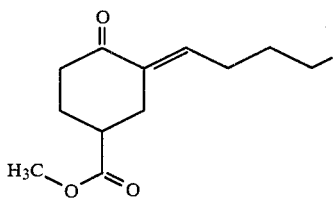

The resulting compound having the structure:

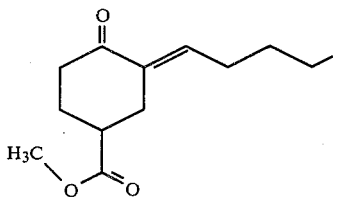

is then admixed with 100 ml isopropyl alcohol and placed in a Parr shaker equipped with hydrogenation apparatus and containing 2 grams of a 10% palladium on carbon catalyst. The reaction mass is then hydrogenated at a temperature of 90°–100° C. and at a pressure of 8.5 atmospheres over a period of five hours. At the end of the five hour period, the reaction vessel is opened and the reaction mass if filtered.

FIG. 7 is the GLC profile of the resulting reaction product prior to distillation (conditions: SE-30, column programmed at 220° C. isothermal). The peak indicated by reference numeral "70" is the peak for the compound having the structure:

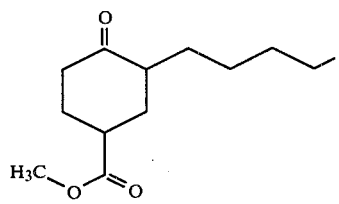

The resulting product is distilled at a vapor temperature of 130° C. at 3 mm/Hg pressure to yield the compound having a jasmine-like, citrusy, lemony aroma with fresh floral lemony undertones.

EXAMPLE IV

PREPARATION OF 4-OXO-3-n-PENTYL-CYCLOHEXANE CARBOXYLIC ACID, METHYL ESTER

Reaction:

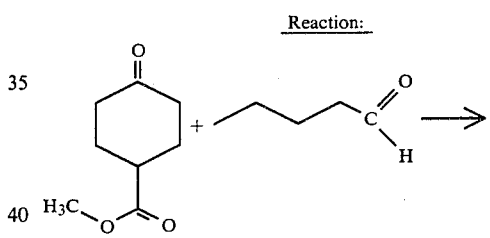

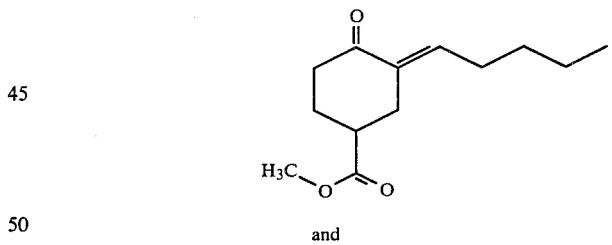

and

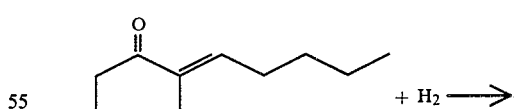

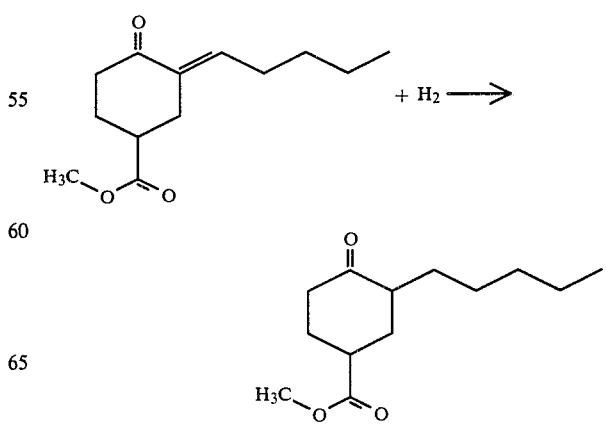

Into a 3-liter reaction vessel equipped with stirrer, thermometer, reflux condenser and hydrogen chloride inlet is placed a mixture of 400 ml toluene and 290 grams of the ketoester having the structure:

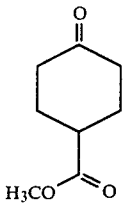

The resulting mixture is cooled to 0° C. and is saturated with hydrogen chloride gas while maintaining the temperature of the reaction mass at 0° C. 57 Grams of sodium sulfate is then added to the reaction mass while permitting the temperature to remain at 5°-10° C. Over a period of two hours, a mixture of 400 ml toluene and 318.2 grams of valeraldehyde is added to the reaction mass. At the end of the two hour period, the reaction mass is permitted to rise to room temperature. The reaction mass is maintained at 30° C. for a period of two hours. At the end of the reaction, the reaction mass is quenched with water and neutralized with sodium carbonate and then evaporated on a one plate distillation column.

The resulting product has the structure:

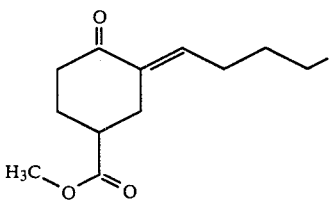

FIG. 8 is the GLC profile for the reaction product having the structure:

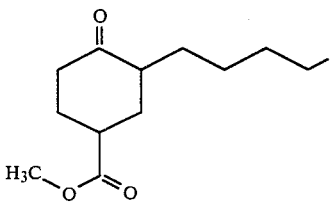

The peak indicated by reference numeral "80" is the peak for the compound having the structure:

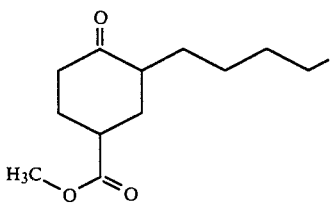

The reaction mass is then placed in a par shaker into which has been previously placed 2 grams of 10% palladium on carbon catalyst and 1.8-liters of anhydrous isopropanol. The parr shaker is sealed and hydrogenated to a pressure of 8.2 atmospheres at 180° C. for a period of six hours. At the end of the six hour period, the parr shaker is opened and the reaction mass is filtered. The resulting filtrate is distilled yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 23/25 | 23/110 | 50/4 | 32.1 |
| 2 | 90 | 140 | 4.0 | 10.1 |
| 3 | 100 | 158 | 4.0 | 34.1 |
| 4 | 110 | 162 | 4.0 | 32.0 |
| 5 | 128 | 175 | 4.0 | 6.2 |
| 6 | 130 | 180 | 4.0 | 10.1 |
| 7 | 130 | 190 | 3.0 | 9.6 |
| 8 | 130 | 180 | 3.0 | 9.8 |
| 9 | 130 | 180 | 3.0 | 13.1 |
| 10 | 130 | 180 | 3.0 | 15.1 |
| 11 | 130 | 185 | 3.0 | 15.2 |
| 12 | 126 | 195 | 3.0 | 13.0 |
| 13 | 120 | 200 | 3.0 | 7.6 |
| 14 | 117 | 215 | 3.0 | 2.6 |

FIG. 8 is the GLC profile for the reaction product prior to hydrogenation containing the compound having the structure:

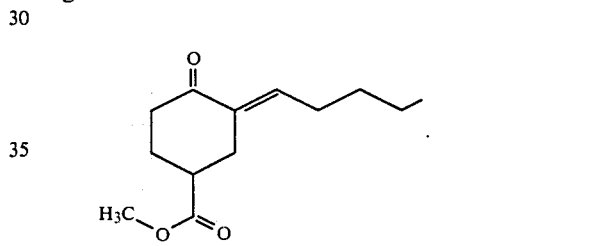

FIG. 9 is the GLC profile for the reaction product subsequent to hydrogenation containing the compound having the structure:

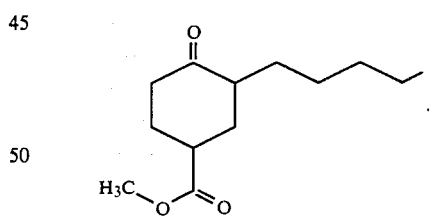

The preak indicated by reference numeral "90" is the peak for the compound having the structure:

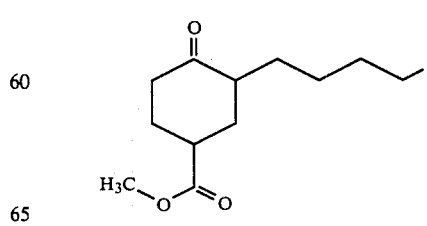

FIG. 10 is the NMR spectrum for the compound having the structure:

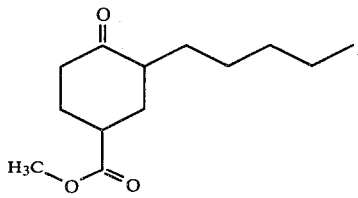

(conditions: Field strength: 100 MHz; Solvent: CFCl₃).

FIG. 11 is the infra-red spectrum for the compound having the structure:

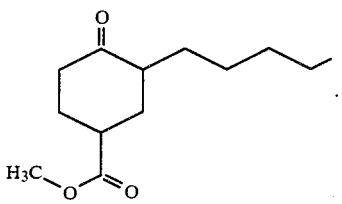

The resulting product has a jasmine, citrus, lemony aroma with fresh floral jasmine, lemony undertones.

EXAMPLE V

PREPARATION OF ETHYL ESTER OF 4-OXO-3-n-PENTYLCYCLOHEXANE CARBOXYLIC ACID

Reaction:

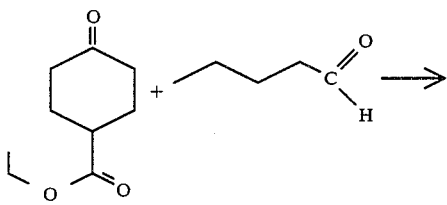

and

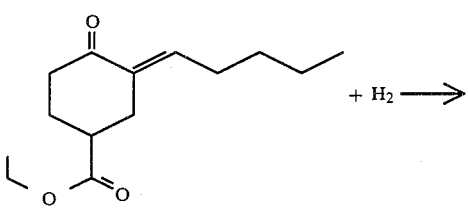

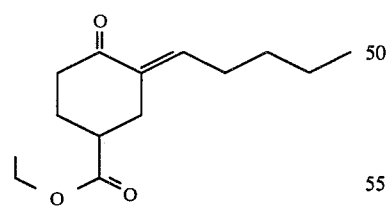

-continued
Reaction:

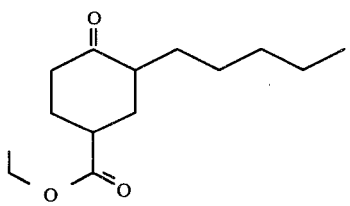

Into a 5-liter reaction vessel equipped with heating mantle, stirrer thermometer, reflux condenser and hydrogen chloride gas inlet tube is placed a mixture of 1-liter of toluene and 531 grams of the compound having the structure:

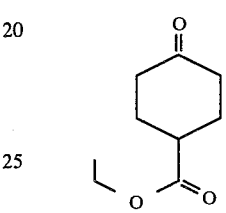

The resulting mixture is cooled to 0° C. and the mixture is then saturated with hydrogen chloride gas while maintaining the temperature at 0° C. 114 Grams of anhydrous sodium sulfate is then added to the reaction mass. Over a period of 1.25 hours, a mixture of 533.2 grams of valeraldehyde and 1-liter of toluene is added to the reaction mass while maintaining the reaction mass of 5°–10° C. At the end of the 1.25 hour addition period, the reaction mass is stirred at a temperature of 10° C. for a period of three hours. At the end of the three hour period, the reaction mass is washed with water and neutralized with sodium bicarbonate. The solvent is then evaporated on a rotovap evaporater yielding the product having the structure:

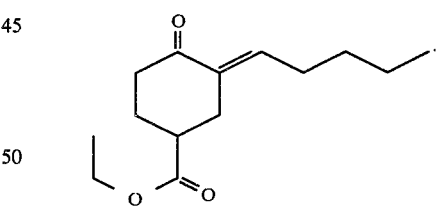

FIG. 12 is the GLC profile for the compound having the structure:

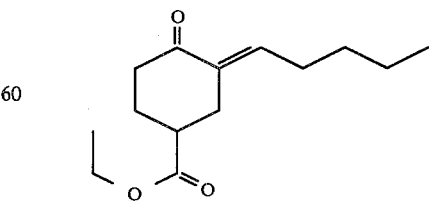

produced as a result of this portion of the example. The peak indicated by reference numeral "121" is the peak for the compound having the structure:

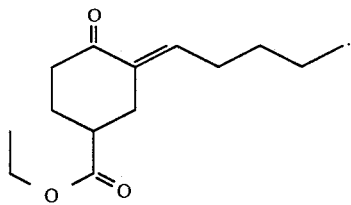

The resulting reaction product is then added to an autoclave containing 5 grams of 10% palladium on carbon and 1-liter of isopropyl alcohol. The autoclave is sealed and hydrogen is added to a pressure of 3 atmospheres at a temperature of 140° C. for a period of nine hours. At the end of the nine hour period, the reaction vessel is opened and the reaction mass is filtered.

FIG. 13 is the GLC profile for the reaction product containing the compound having the structure:

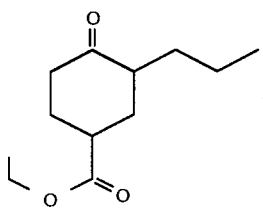

The peak indicated by reference numeral "130" is the peak for the compound having the structure:

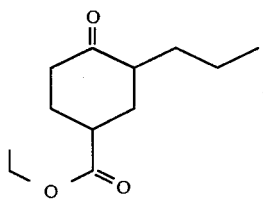

The reaction mass is then fractionally distilled at 4 mm/Hg. pressure and 135° C. to yield the compound having the structure:

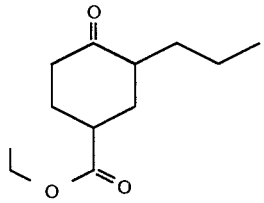

FIG. 14 is the NMR spectrum for the compound having the structure:

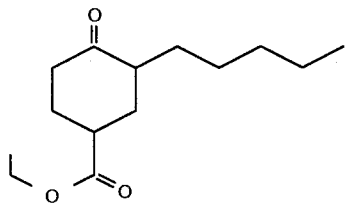

(conditions: Field strength: 100 MHz; Solvent: $CFCl_3$).

FIG. 15 is the infra-red spectrum for the compound having the structure:

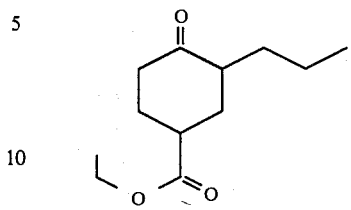

EXAMPLE VI

PREPARATION OF METHYL ESTER OF 3-n-HEXYL-4-OXO-CYCLOHEXANE CARBOXYLIC ACID

Reactions:

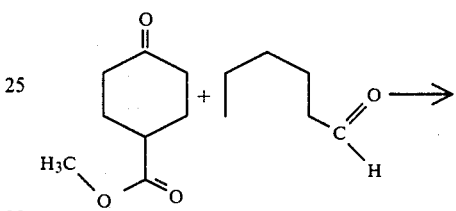

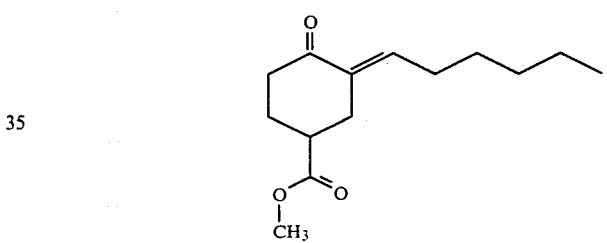

and

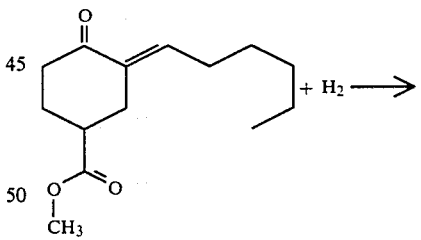

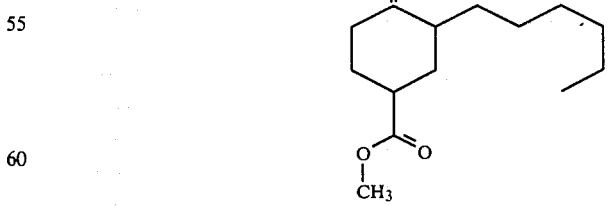

Into a 300 ml reaction flask equipped with stirrer, cooling bath, reflux condenser, stirring thermometer and hydrogen chloride gas inlet tube is placed 50 ml toluene and 15.8 grams of ketoester having the structure:

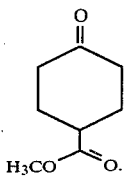

The resulting mixture is cooled to 0° C. and while maintaining the mixture of 0° C. the mixture is saturated with hydrogen chloride gas. 5 Grams of anhydrous sodium sulfate is then added to the reaction mass. Over a period of two hours while maintaining the reaction mass at 5°–10° C. a mixture of 18 grams of n-hexanal and 50 ml toluene is added to the reaction mass. The reaction mass is then stirred at 5° to 10° C. for a period of three hours. At the end of the three hour period, the reaction mass is washed with water and neutralized with sodium carbonate. The reaction mass is then stripped of solvent on a one plate distillation column. The resulting product has the structure:

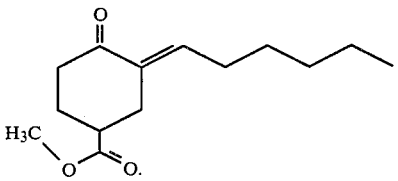

The resulting product is then placed into an autoclave which already contains 100 ml isopropyl alcohol and 0.5 grams of 10% palladium on carbon catalyst. The autoclave is sealed and hydrogenated at a temperature of 140° C., a pressure of 4.5 atmospheres for a period of time of seven hours. At the end of the seven hour period, the autoclave is opened and the reaction mass is filtered and distilled. The reaction product has the structure:

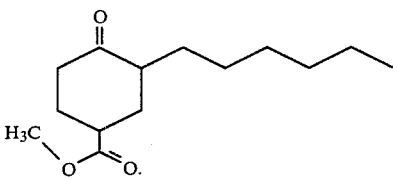

FIG. 16 is the NMR spectrum for the compound having the structure:

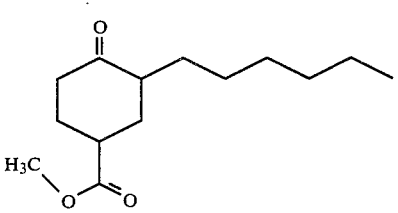

(conditions: Field strength: 100 MHz; Solvent: CFCl₃).

FIG. 17 is the infra-red spectrum for the compound having the structure:

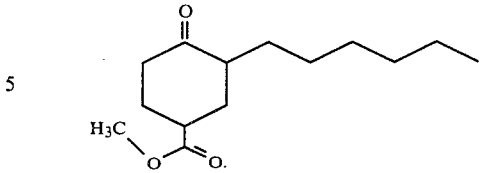

The compound having the structure:

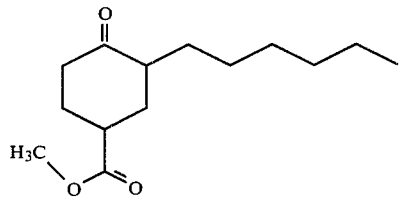

has a valerian oil aroma with long lasting jasmine and green undertones.

EXAMPLE VII

PREPARATION OF METHYL ESTER OF 4-OXO-3-n-PROPYL CYCLOHEXANE CARBOXYLIC ACID

Reactions:

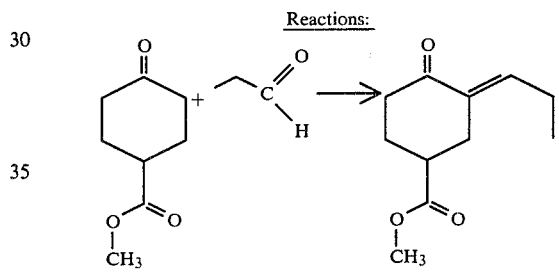

and

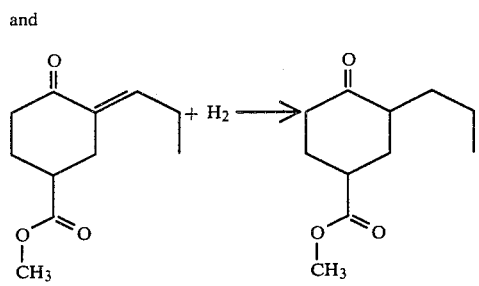

Into a 300 cc reaction flask equipped with stirrer thermometer, reflux condenser cooling bath and hydrogen chloride inlet tube is placed a mixture of 48 ml toluene and 15.8 grams of ketoester having the structure:

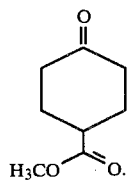

The resulting mixture is cooled to 0° C. and saturated with hydrogen chloride gas while maintaining the temperature at 0° C. The resulting mixture is then admixed with 5 grams of anhydrous sodium sulfate. Over a period of one hour, a mixture of 50 ml toluene and 11 grams of propionaldehyde is added to the reaction mass while maintaining the temperature at 5°–10° C. At the end of the one hour period, the reaction mass is then permitted to rise in temperature to 30° C. The reaction mass is maintained at 30° C. for a period of 2.5 hours. At the end of the 2.5 hour period, the reaction mass contains the compound having the structure:

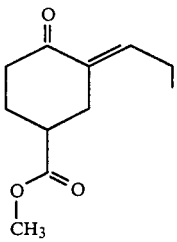

FIG. 18 is the GLC profile for the reaction mass at this point containing the compound having the structure:

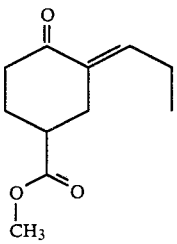

The peak indicated by reference numeral "180" is the peak for the compound having the structure:

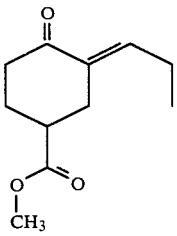

(conditions: 10% SE-30 column programmed at 180° C. isothermal).

The resulting product is then placed in an autoclave which contains 100 ml isopropyl alcohol and 2 grams of 10% palladium on carbon catalyst. The autoclave is sealed and pressurized to 4 atmospheres pressure at 140° C. for a period of seven hours with hydrogen. At the end of the hydrogenation period, the autoclave is cooled and opened and the contents filtered. The resulting product has the structure:

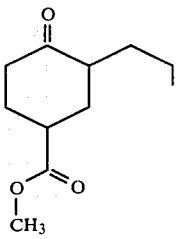

The resulting product has the GLC profile as set forth in FIG. 19 and contains the compound having the structure:

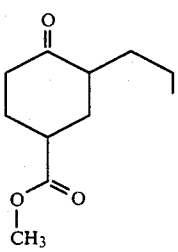

The peak indicated by reference numeral "190" is the peak for the compound having the structure:

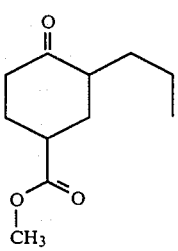

(conditions: 10% SE-30 column programmed at 220° C. isothermal).

FIG. 20 is the NMR spectrum for the compound having the structure:

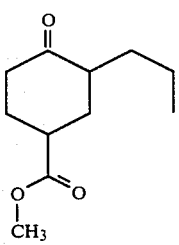

(conditions: Field strength: 100 MHz; Solvent: CFCl$_3$).

FIG. 21 is the infra-red spectrum for the compound having the structure:

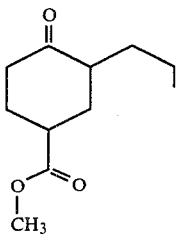

The resulting compound has a burnt maple aroma with pineapple-like undertones.

EXAMPLE VIII

PREPARATION OF METHYL ESTER OF 3-ISOBUTYL-4-OXO-CYCLOHEXANE CARBOXYLIC ACID

Reactions:

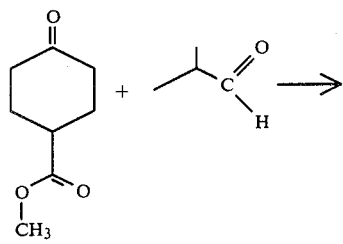 + 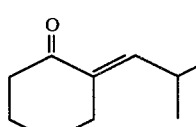 →

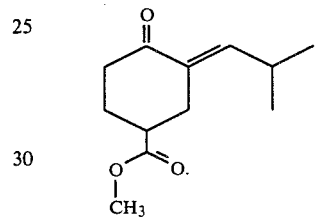

and

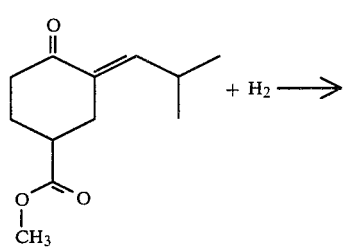 + H$_2$ →

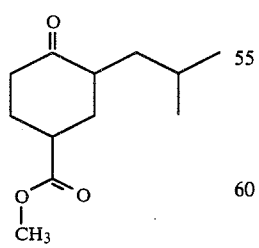

Into a 300 cc reaction vessel equipped with stirrer, thermometer, reflux condenser, cooling coils and hydrogen chloride inlet tube is placed a mixture of 50 ml toluene and 15.8 grams of the ketoester having the structure:

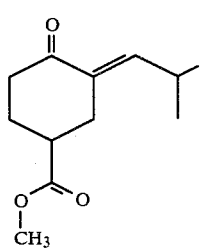

The reaction mass is cooled to 0° C. and while maintaining the reaction mass at 0° C., the reaction mass is saturated with anhydrous hydrogen chloride gas. 5 Grams of sodium sulfate is then added to the reaction mass. To the reaction mass over a period of one hour is added a mixture of 50 ml toluene and 13.0 grams of isobutyraldehyde. The reaction mass is then permitted to rise in temperature from +10° C. up to +30° C. The reaction mass is then stirred at 30° C. for a period of 2.5 hours. At the end of the reaction, the reaction mass is neutralized with sodium carbonate and the solvent is evaporated on a roto vap evaporator. The resulting product has the structure:

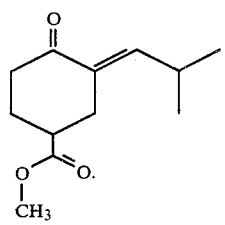

FIG. 22 is the GLC profile of the reaction product containing the compound having the structure:

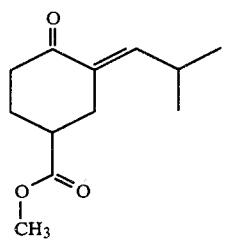

The peak indicated by reference numeral "220" is the peak for the compound having the structure:

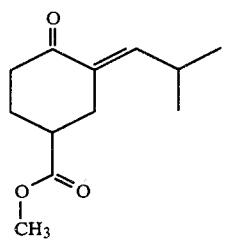

(conditions: 10% SE-30 column programmed at 180°C. isothermal).

The reaction product is then charged to an autoclave containing 100 ml isopropyl alcohol and 2 grams 10% palladium on carbon catalyst. The autoclave is sealed and hydrogenated at a pressure of 4.5 atmospheres and a temperature of 143° C. for a period of six hours. At the end of the six hour period, the autoclave is cooled and opened and the contents are filtered and distilled. The resulting reaction product contains the compound having the structure:

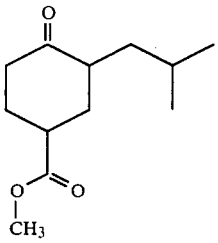

FIG. 23 is the GLC profile for the reaction product containing the compound having the structure:

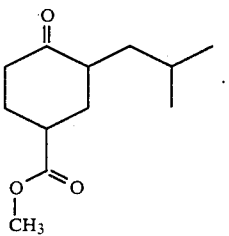

The peak indicated by reference numeral "230" is the peak for the compound having the structure:

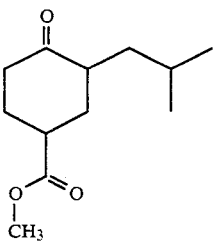

(conditions: 10% SE-30 column programmed at 220° C. isothermal).

FIG. 24 is the NMR spectrum for the compound having the structure:

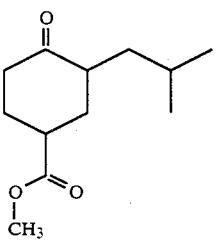

(conditions: Field strength: 100 MHz; Solvent: CFCl₃).

FIG. 25 is the infra-red spectrum for the compound having the structure:

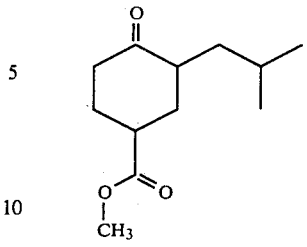

The resulting product has a maple, nutty aroma.

EXAMPLE IX

PREPARATION OF METHYL ESTER OF 3-n-BUTYL-4-OXO-CYCLOHEXANE CARBOXYIC ACID

Reactions:

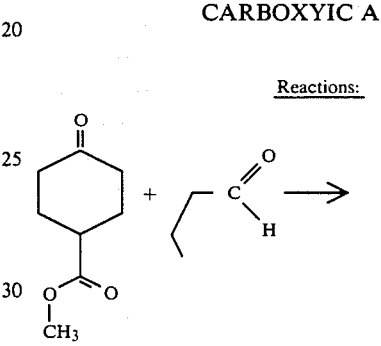

and

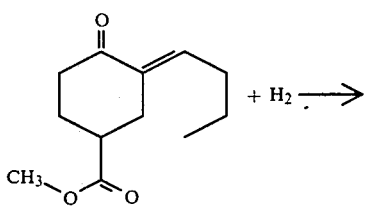

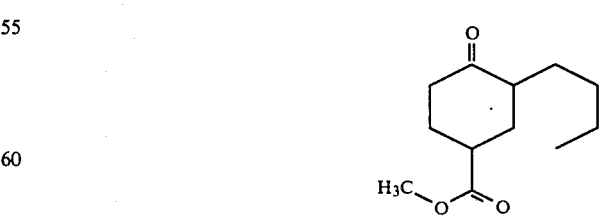

Into a 300 cc reaction vessel equipped with stirrer thermometer, reflux condenser and cooling coils is placed a mixture of 15.2 grams of the ketoester having the structure:

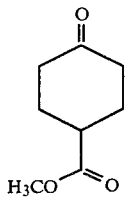

and 50 ml toluene. The resulting mixture is cooled to 0° C. and is then saturated with anhydrous hydrogen chloride gas while maintaining the temperature at 0° C. At the end of the addition of the hydrogen chloride gas, B 5 grams of anhydrous sodium sulfate is added to the reaction mass. While maintaining the reaction temperature at 5°-10° C. over a period of 0.5 hours, a mixture of 50 ml of toluene and 18.0 grams of n-butanal is added with stirring. The reaction mass is then permitted to rise in temperature to 30° C. over a period of 0.5 hours. The reaction mass is then maintained with stirring at 30° C. for a period of 3.0 hours. At the end of the 3.0 hour period, the reaction mass is neutralized with sodium carbonate and the solvent is stripped from the reaction mass using a rotovap. The resulting product has the structure:

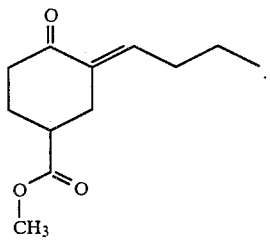

FIG. 26 is the GLC profile for the reaction mass containing the compound having the structure:

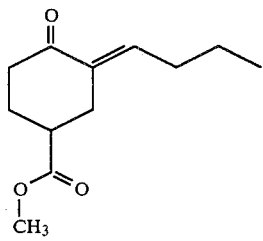

The peak indicated by reference numeral "260" is the peak for the compound having the structure:

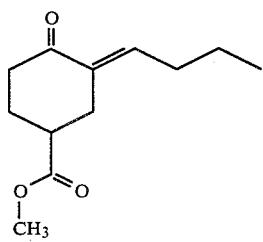

(conditions: 10% SE-30 column programmed at 180° C. isothermal).

The resulting product is then charged to an autoclave containing 100 ml isopropyl alcohol and 2 grams 10% cooked palladium on carbon catalyst. The autoclave is sealed and the reaction mass is pressurized to 5 atmospheres pressure at 150° C. with hydrogen and maintained at that pressure and temperature for a period of 5.5 hours. At the end of the 5.5 hour period, the reaction mass is then cooled and the autoclave is opened and filtered. The resulting filtrate is distilled yielding the product having the structure:

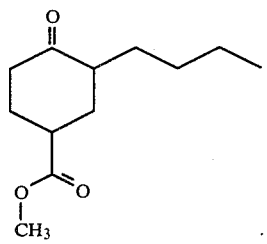

The peak indicated by reference numeral "270" is the peak for the compound having the structure:

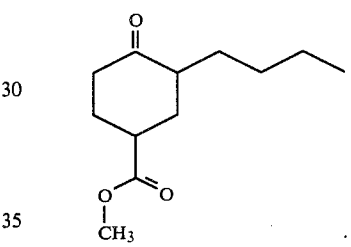

FIG. 28 is the NMR spectrum for the compound having the structure:

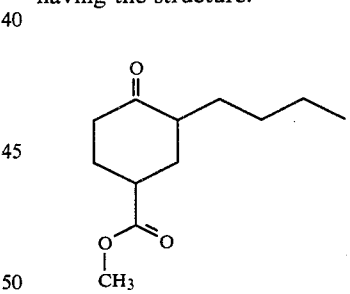

(conditions: Field strength: 100 MHz; Solvent: CFCl$_3$).

FIG. 29 is the infra-red spectrum for the compound having the structure:

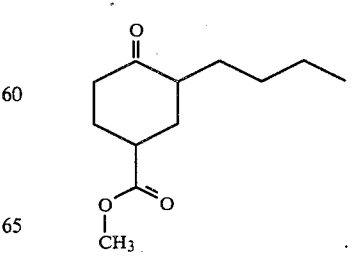

The resulting product having the structure:

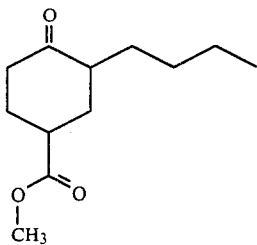

has a meaty, cocoa and coffee aroma profile.

EXAMPLE X

PREPARATION OF METHYL ESTER OF 3-ISOPENTYL-4-OXO-CYCLOHEXANE CARBOXYLIC ACID

Reactions:

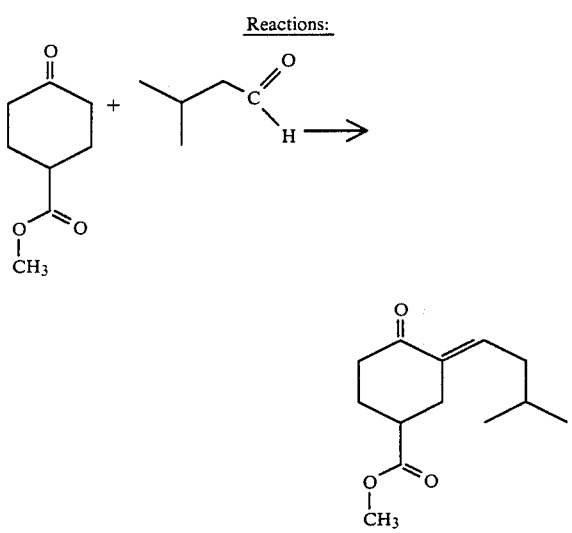

and

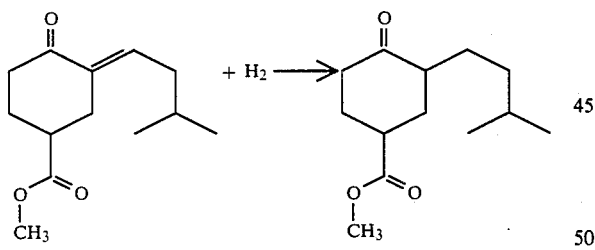

Into a 300 ml reaction flask equipped with stirrer, thermometer, cooling coil, and hydrogen chloride inlet tube is placed a mixture 50 ml toluene and 15.8 grams of ketoester having the structure:

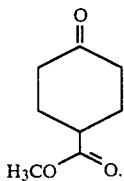

The resulting mixture is cooled to −10° C. While maintaining the reaction mass at −10° C. the reaction mass is saturated with anhydrous hydrogen chloride gas. The reaction mass is maintained at −10° up to −5° C. and 5 grams of anhydrous sodium sulfate is added. To the reaction mass, over a period of one hour, while maintaining the reaction mass at −10° up to −5° C., a mixture of 50 ml toluene and 18 grams of isovaleraldehyde is added to the reaction mass. At the end of the feeding of the mixture of isovaleraldehyde and toluene, the reaction mass temperature is allowed to rise to 30° C. The reaction mass is maintained at 30° C. with stirring for a period of 2.7 hours. At the end of the 2.7 hour period, the reaction mass is washed and neutralized with sodium carbonate and the solvent is evaporated on a rotovap evaporator. The resulting reaction mass contains the compound having the structure:

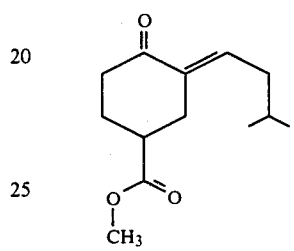

The resulting reaction mass is then charged to an autoclave containing 100 ml anhydrous isopropyl alcohol and 2 grams of 10% palladium on carbon catalyst. The autoclave is sealed and pressurized with hydrogen to a pressure of 5 atmospheres while maintaining the temperature at 170° C. for a period of six hours. At the end of the six hour period the autoclave is cooled and opened. The contents are filtered and distilled yielding the compound having the structure:

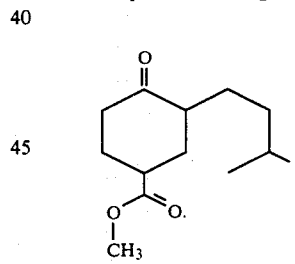

FIG. 30 is the NMR spectrum for the compound having the structure:

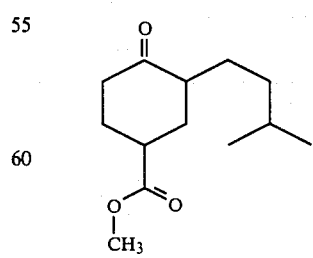

(conditions: Field strength: 100 MHz; Solvent: CFCl$_3$).

FIG. 31 is the infra-red spectrum for the compound having the structure:

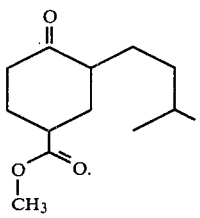

The resulting product has a valerian oil green aroma with pleasant almond undertones.

EXAMPLE XI(A)

PREPARATION OF TRIMETHYL ESTER OF 1-OXO-2,4,4-CYCLOHEXANE TRICARBOXYLIC ACID

Reaction:

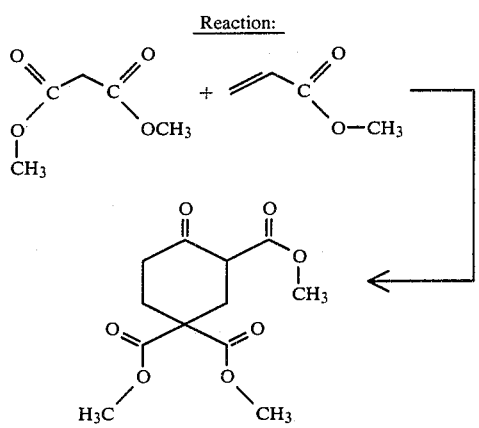

Into a 5-liter reaction vessel is placed 2,400 ml toluene and 184.8 grams of sodium hydride. The resulting mixture is heated to 40° C. and over a period of 1.25 hours, dimethyl malonate is added (528 grams). Over a period of ten minutes, 800 ml dimethylformamide is added to the reaction mass. Over a period one hour, 705 grams of methyl acrylate is added to the reaction mass. The reaction mass is then heated to reflux and refluxed for a period of four hours. At the end of the four hour period, the reaction mass is cooled down and quenched into 5-liters of water. The reaction mass is then distilled on a one plate short path column yielding 698.8 grams of product. The fractions yielded as a result of this distillation are as follows:

| Fraction No. | Vapor Temp. (°C.) | Liquid Temp. (°C.) | Vacuum mm/Hg. Pressure (gms) |
|---|---|---|---|
| 1 | /46 | /55 | 1.00 |
| 2 | 47 | 55 | 1.00 |
| 3 | 170 | 180 | 3.00 |
| 4 | 175 | 220 | 3.00 |

FIG. 32 is the NMR spectrum for the compound having the structure:

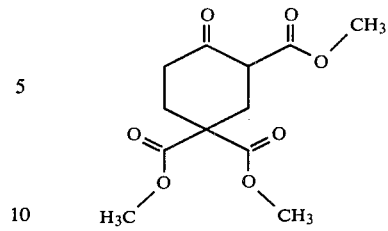

(Conditions: Field strength: 100 MHz; Solvent: $CFCl_3$).

FIG. 33 is the infra-red spectrum for the compound having the structure:

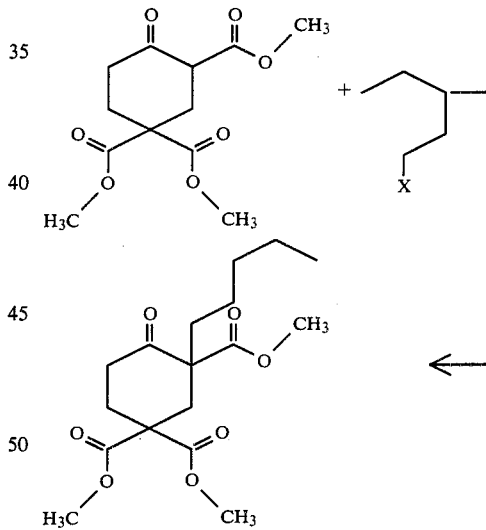

EXAMPLE XI(B)

PREPARATION OF TRIMETHYL ESTER OF 1,3,5-n-DECANETRICARBOXYLIC ACID

Reactions:

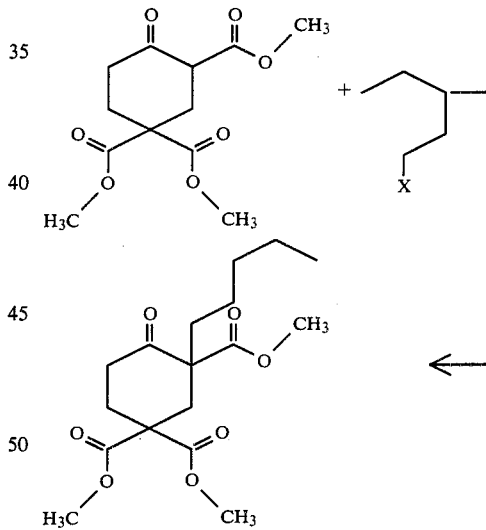

(wherein X represents bromo); and

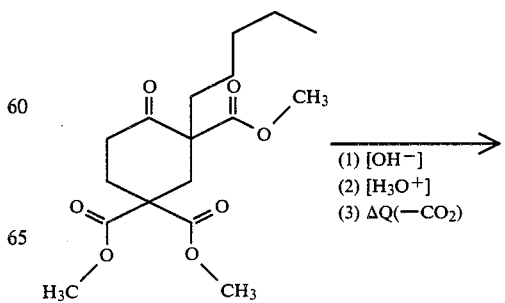

(1) [OH$^-$]
(2) [H$_3$O$^+$]
(3) ΔQ(—CO$_2$)

-continued

Reactions:

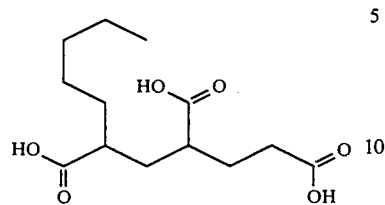

and

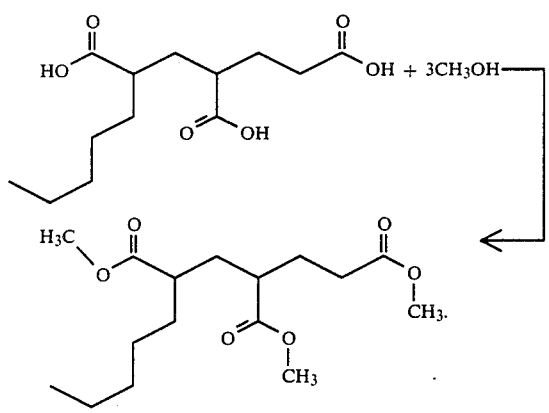

2,4,4-Tricarbomethoxy cyclohexanone (271 grams) produced according to Example XI(A) is added to a solution of 123 grams of potassium-t-butoxide in t-butanol.

The resulting solution is heated to reflux whereupon 1-bromo pentane is added over a period of one hour. The reaction mass is then stirred at reflux for a period of four hours.

400 Grams of 25% sodium hydroxide solution is then added while refluxing the reaction mass. The resulting reaction mass is stirred at reflux for a period of two hours. The reaction mass is then cooled whereupon 500 ml of water is added. Concentrated hydrochloride acid (800 ml) is then added over a one hour period while maintaining the reaction mass at 25°-40° C. accompanied by vigorous gas evolution. 200 Ml toluene is then added to the reaction mass and the organic solution is separated from the inorganic solution. The solvents are removed from the organic solution on a rotary evaporator to afford 310 grams of viscous oil. This oil is dissolved in 400 ml methanol and treated with a stream of anhydrous hydrogen chloride while refluxing at 82° C.

The reaction mass is then heated for six hours. Methanol is distilled away from the crude reaction mass until a pot temperature of 100° C. is reached. The crude reaction mass is then cooled, triturated at 200 ml of toluene and washed twice with water. Distillation affords 128 grams of methyl-4,6-dicarbomethoxyundecylenate (boiling point 185° C. at 1 mm/Hg. pressure) having the following structure:

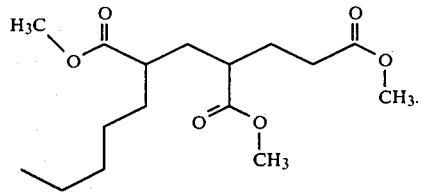

FIG. 34 is the GLC profile of the reaction product containing the compound having the structure:

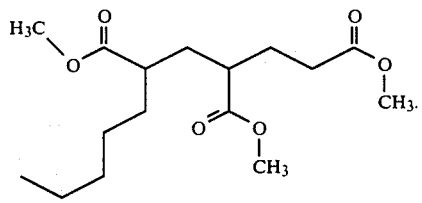

The peak indicated by reference numeral "340" is the peak for the compound having the structure:

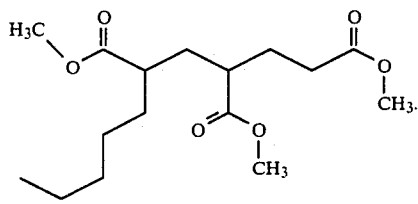

FIG. 35 is the NMR spectrum for the compound having the structure:

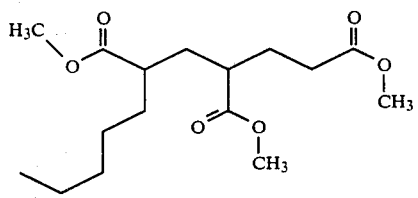

(conditions: Field strength: 100 MHz; Solvent: CFCl$_3$).

FIG. 36 is the infra-red spectrum for the compound having the structure:

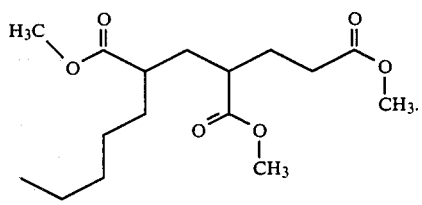

EXAMPLE XI(C)

PREPARATION OF METHYL ESTER OF 4-OXO-3-n-PENTYL CYCLOHEXANE CARBOXYLIC ACID

Reactions:

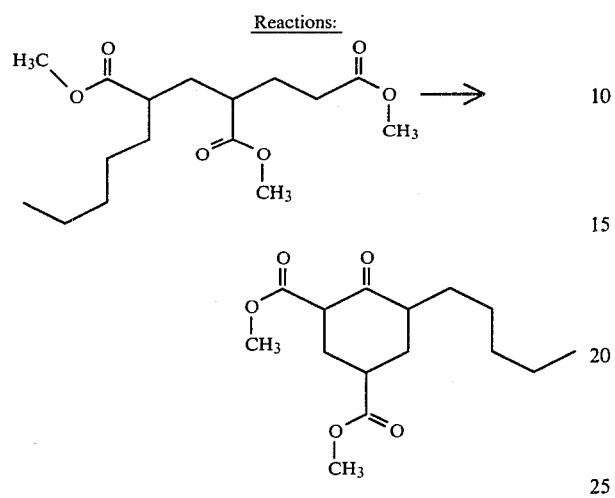

and

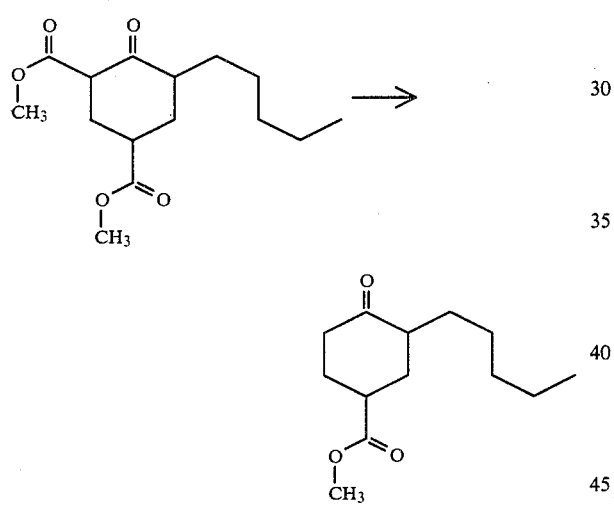

Methyl-4,6-dicarbomethoxyundecylenate (128 grams) having the structure:

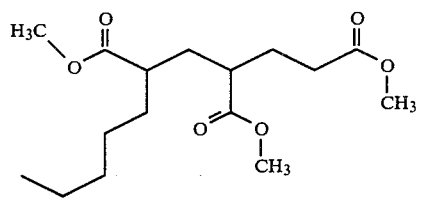

prepared according to Example XI(B) is added to a solution of 62 grams of potassium t-butoxide in 200 ml toluene and 300 ml dimethylformamide.

The resulting slurry is heated to 140° C. while distilling off the methanol. The reaction mass is then aged at 148° C. for a period of two hours. The reaction mass is then cooled to 60° C. and poured into 1-liter of water containing 80 ml of acetic acid. The organic layer is separated from the inorganic layer. The resulting inorganic (aqueous) layer is extracted with 100 ml toluene. The combined toluene extract and organic layer is then heated to 220° C. while distilling away solvent. At 220° C., 18 ml of water are added dropwise over a period of one hour. Methanol, water and carbon dioxide are evolved. The organic mass is then distilled at 3 mm/Hg. pressure to afford 62 grams of 2-n-pentyl-4-carbomethoxy cyclohexanone having the structure:

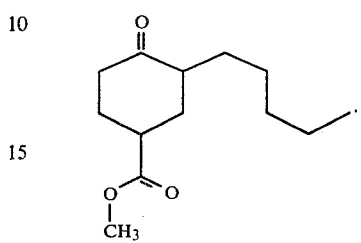

EXAMPLE XII

PREPARATION OF METHYL ESTER OF 4-OXO-3-n-PENTYLCYCLOHEXANE CARBOXYLIC ACID

Reactions:

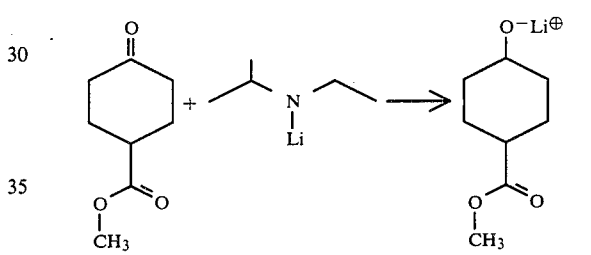

and

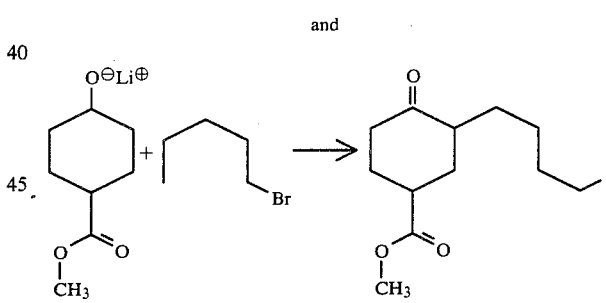

To a stirred solution of 500 ml of lithium diisopropylamine in tetrahydrofuran are added dropwise 156 grams of 4-carbomethoxy cyclohexanone at −28° C. having the structure:

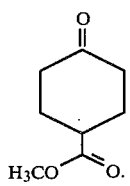

The resulting solution is stirred for 0.5 hours at −28° C. whereupon 1-bromopentane is added with stirring and cooling. Just prior to the addition of the 1-bromopentane the resulting product has the structure:

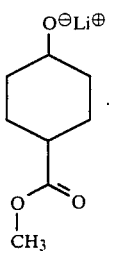

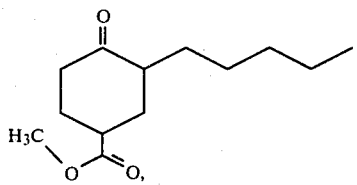

distilling at 130° C. at 3.1 mm/Hg. pressure.

EXAMPLE XIII

The alkyl substituted and unsubstituted para-carboalkoxy cyclohexanones of our invention produced according to Examples I–XII inclusive have very long lasting fruity, woody, strawberry, raspberry-like, green, fresh floral, jasmine-like, lemony, burnt maple, maple/nutty, cocoa-like, coffee-like and valerian oil-like aromas with woody ionone-like, sweet raspberry-like, licorice, jasmine-like and citrusy undertones which may be utilized to a great extent in inexpensive functional products. The following pine fragrance demonstrates the use of these materials in perfume compositions.

The resulting reaction mass is allowed to come to room temperature and is quenched into 3-liters of water. The resulting mixture is extracted three times with diethyl ether (500 ml portions). The combined ether extracts are extracted with 500 ml of 10% sodium chloride solution. The resulting organic mass is distilled to yield 100 grams of product having the structure:

| INGREDIENTS | PARTS BY WEIGHT | | | | | | | | | | |
|---|---|---|---|---|---|---|---|---|---|---|---|
| | XIIIa | XIIIb | XIIIc | XIIId | XIIIe | XIIIf | XIIIg | XIIIh | XIIIi | XIIIj | XIIIk |
| Isobornyl acetate | 100 | 100 | 100 | 100 | 100 | 100 | 100 | 100 | 100 | 100 | 100 |
| Camphor | 10 | 10 | 10 | 10 | 10 | 10 | 10 | 10 | 10 | 10 | 10 |
| Terpineol | 25 | 25 | 25 | 25 | 25 | 25 | 25 | 25 | 25 | 25 | 25 |
| Fir Balsam Absolute (50% in Diethyl Phthalate) | 20 | 20 | 20 | 20 | 20 | 20 | 20 | 20 | 20 | 20 | 20 |
| Coumarin | 4 | 4 | 4 | 4 | 4 | 4 | 4 | 4 | 4 | 4 | 4 |
| Linalool | 30 | 30 | 30 | 30 | 30 | 30 | 30 | 30 | 30 | 30 | 30 |
| Anethol | 2 | 2 | 2 | 2 | 2 | 2 | 2 | 2 | 2 | 2 | 2 |
| Fenchyl Alcohol | 10 | 10 | 10 | 10 | 10 | 10 | 10 | 10 | 10 | 10 | 10 |
| Lemon Terpenes Washed | 50 | 50 | 50 | 50 | 50 | 50 | 50 | 50 | 50 | 50 | 50 |
| Borneol | 5 | 5 | 5 | 5 | 5 | 5 | 5 | 5 | 5 | 5 | 5 |
| Galbanum Oil | 5 | 5 | 5 | 5 | 5 | 5 | 5 | 5 | 5 | 5 | 5 |
| Turpentine Russian | 150 | 150 | 150 | 150 | 150 | 150 | 150 | 150 | 150 | 150 | 150 |
| Pinus Pumilionus | 50 | 50 | 50 | 50 | 50 | 50 | 50 | 50 | 50 | 50 | 50 |
| Eucalyptol | 50 | 50 | 50 | 50 | 50 | 50 | 50 | 50 | 50 | 50 | 50 |
| 2,2,6-trimethyl-1-cyclohexene-1-carboxaldehyde | 5 | 5 | 5 | 5 | 5 | 5 | 5 | 5 | 5 | 5 | 5 |
| Maltol 1% in Diethyl Phthalate | 5 | 5 | 5 | 5 | 5 | 5 | 5 | 5 | 5 | 5 | 5 |
| Product produced according to Example I having the structure: | 12 | 0 | 0 | 0 | 0 | 0 | 0 | 0 | 0 | 0 | 0 |

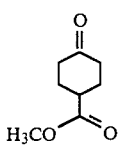

| | | | | | | | | | | | |
|---|---|---|---|---|---|---|---|---|---|---|---|
| Product produced according to Example II having the structure: | 0 | 12 | 0 | 0 | 0 | 0 | 0 | 0 | 0 | 0 | 0 |

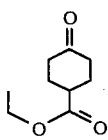

| | | | | | | | | | | | |
|---|---|---|---|---|---|---|---|---|---|---|---|
| Product produced according to one of Examples III, IV, XI(C) or XII having the structure: | 0 | 0 | 12 | 0 | 0 | 0 | 0 | 0 | 0 | 0 | 0 |

-continued

| INGREDIENTS | PARTS BY WEIGHT | | | | | | | | | | |
|---|---|---|---|---|---|---|---|---|---|---|---|
| | XIIIa | XIIIb | XIIIc | XIIId | XIIIe | XIIIf | XIIIg | XIIIh | XIIIi | XIIIj | XIIIk |

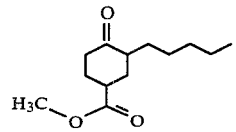

Compound having the structure:

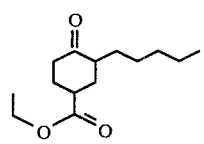

produced according to Example V.

| | 0 | 0 | 0 | 12 | 0 | 0 | 0 | 0 | ·0 | 0 | 0 |

Compound having the structure:

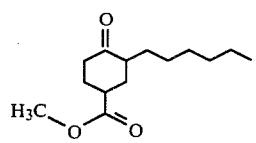

produced according to Example VI.

| | 0 | 0 | 0 | 0 | 12 | 0 | 0 | 0 | 0 | 0 | 0 |

Compound having the structure:

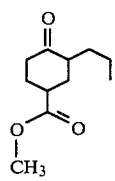

produced according to Example VII

| | 0 | 0 | 0 | 0 | 0 | 12 | 0 | 0 | 0 | 0 | 0 |

Compound having the structure:

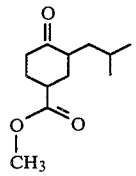

produced according to Example VIII.

| | 0 | 0 | 0 | 0 | 0 | 0 | 12 | 0 | 0 | 0 | 0 |

Compound having the structure:

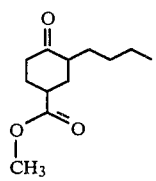

produced according to Example IX.

| | 0 | 0 | 0 | 0 | 0 | 0 | 0 | 12 | 0 | 0 | 0 |

Compound having the structure:

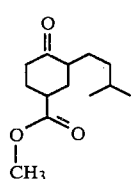

| | 0 | 0 | 0 | 0 | 0 | 0 | 0 | 0 | 12 | 0 | 0 |

-continued

| INGREDIENTS | PARTS BY WEIGHT | | | | | | | | | | |
| --- | --- | --- | --- | --- | --- | --- | --- | --- | --- | --- | --- |
| | XIIIa | XIIIb | XIIIc | XIIId | XIIIe | XIIIf | XIIIg | XIIIh | XIIIi | XIIIj | XIIIk |
| produced according to Example X. | | | | | | | | | | | |
| 50:50 Mixture of compounds having the structures: | 0 | 0 | 0 | 0 | 0 | 0 | 0 | 0 | 0 | 12 | 0 |

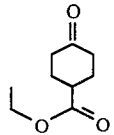

and

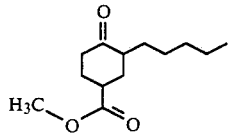

| 50:50 Mixture of compounds having the structures: | 0 | 0 | 0 | 0 | 0 | 0 | 0 | 0 | 0 | 0 | 12 |

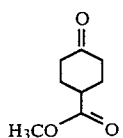

and

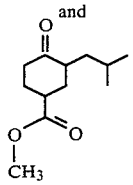

The following pine aromas are each modified by the various alkyl substituted and unsubstituted para-carboalkoxy cyclohexanones or mixtures of same added to the basic pine aroma. Thus, the following examples can be described as having the following aromas:

| Example No. | Description |
| --- | --- |
| XIIIa | Piney with fruity, woody and ionone-like nuances with a strong woody ionone-like undertone. |
| XIIIb | Piney with strawberry-like, raspberry-like, and green topnotes and sweet raspberry-like and licorice undertones. |
| XIIIc | Piney with fresh floral, jasmine-like and lemony topnotes and jasmine-like and citrusy (lemon) undertones. |
| XIIId | Piney with jasmine topnotes and citrusy undertones. |
| XIIIe | Piney with jasmine and green topnotes. |
| XIIIf | Piney with burnt maple topnotes. |
| XIIIg | Piney with maple/nutty topnotes. |
| XIIIh | Piney with cocoa-like and coffee-like topnotes. |
| XIIIi | Piney with valerian-like and green topnotes and toasted almond undertones. |
| XIIIj | Piney with jasmine-like topnotes. |
| XIIIk | Piney with valerian-like and green topnotes. |

EXAMPLE XIV
A COSMETIC POWDER PREPARATION

A cosmetic powder is prepared by mixing in a ball mill 100 grams of talcum powder with 0.25 grams of one of the substances set forth in Table I below containing at least one of the alkyl substituted and unsubstituted para-carboalkoxy cyclohexanones of our invention. Each of the cosmetic powders has an excellent aroma as described in Table I below.

TABLE I

| Perfumery Substance | Aroma Nuance |
| --- | --- |
| Compound having the structure: 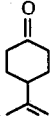 produced according to Example I. | A fruity and woody aroma with woody and ionone-like nuances. |
| Compound having the structure: 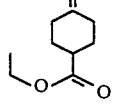 | A strawberry, raspberry and green aroma with sweet raspberry-like and licorice nuances on dry-out. |

TABLE I-continued

| Perfumery Substance | Aroma Nuance |
|---|---|
| produced according to Example II. | |
| Compound having the structure: 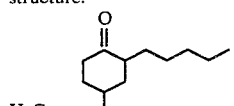 produced according to one of Examples III, IV, XI(C) or XII. | A fresh floral, jasmine-like and lemony aroma with jasmine-like, citrusy and lemony nuances. |
| Compound having the structure: 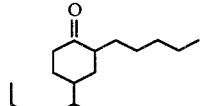 produced according to Example V. | A jasmine-like aroma with citrusy undertones. |
| Compound having the structure: 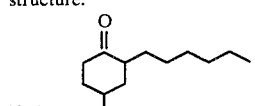 produced according to Example VI. | A jasmine, green aroma. |
| Compound having the structure: 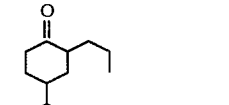 produced according to Example VII. | A burnt maple aroma. |
| Compound having the structure: 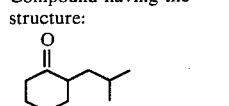 produced according to Example VIII. | A maple/nutty aroma. |
| Compound having the structure: 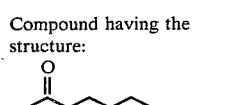 produced according to Example IX. | A cocoa and coffee aroma profile with pyrazine-like undertones. |
| Compound having the structure: 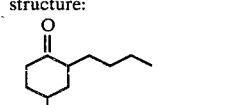 | A valerian oil-like, green aroma with toasted almond |

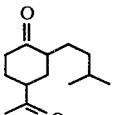

| Perfumery Substance | Aroma Nuance |
|---|---|
| produced according to Example X. | undertones. |
| Perfume composition of Example XIIIa. | Piney with fruity, woody and ionone-like nuances with a strong woody ionone-like undertone. |
| Perfume composition of Example XIIIb. | Piney with strawberry-like, raspberry-like, and green topnotes and sweet raspberry-like and licorice undertones. |
| Perfume composition of Example XIIIc. | Piney with fresh floral, jasmine-like and lemony topnotes and jasmine-like and citrusy (lemon) undertones. |
| Perfume composition of Example XIIId. | Piney with jasmine topnotes and citrusy undertones. |
| Perfume composition of Example XIIIe. | Piney with jasmine and green topnotes. |
| Perfume composition of Example XIIIf. | Piney with burnt maple topnotes. |
| Perfume composition of Example XIIIg. | Piney with maple/nutty topnotes. |
| Perfume composition of Example XIIIh. | Piney with cocoa-like and coffee-like topnotes. |
| Perfume composition of Example XIIIi. | Piney with valerian-like and green topnotes and toasted almond undertones. |
| Perfume composition of Example XIIIj. | Piney with jasmine-like topnotes. |
| Perfume composition of Example XIIIk. | Piney with valerian-like and green topnotes. |

EXAMPLE XV

PERFUMED LIQUID DETERGENT

Concentrated liquid detergents (Lysine salt of n-dodecylbenzene sulfonic acid as more specifically described in U.S. Pat. No. 3,948,818 issued on April 6, 1976 the specification for which is incorporated herein) with aromas as set forth in Table I of Example XIV, supra are prepared containing 0.10%, 0.15, 0.20%, 0.25%, 0.30% and 0.35% of each of the substances of Table I of Example XIV. They are prepared by adding and homogeneously admixing the appropriate quantity of one of the substances of Table I of Example XIV in the liquid detergent. The detergents all possess excellent aromas as set forth in Table I of Example XIV.

EXAMPLE XVI

PREPARATION OF A COLOGNE AND HANDKERCHIEF PERFUME

The substances set forth in Table I of Example XIV are incorporated separately into colognes at concentrations of 2.0%, 2.5%, 3.0%, 3.5%, 4.0%, 4.5% and 5.0% in 75%, 80%, 85%, and 90% aqueous food grade ethanol solutions; and into handkerchief perfumes at concentrations of 15%, 20%, 25% and 30%, in 80%, 85%, 90% and 95% aqueous food grade ethanol solutions. Distinctive aromas as set forth in Table I of Example XIV, supra are imparted to the colognes and to the handkerchief perfume compositions at all levels indicated.

EXAMPLE XVII

PREPARATION OF SOAP COMPOSITION

One hundred grams of soap chips (IVORY ®, produced by the Procter & Gamble Company, of Cincinnati, Ohio) are admixed with 1 grams of each of the substances of Table I of Example XIV, supra. until homogeneous compositions are obtained. The homogeneous compositions are each separated then heated under 3 atmospheres pressure at 180° C. for a period of 3 hours and the resulting liquid samples are placed in soap molds. The resulting soap cake, on cooling, manifest excellent long-lasting aromas as set forth in Table I of Example XIV, supra.

EXAMPLE XVIII

PREPARATION OF SOLID DETERGENT COMPOSITIONS

Detergents are prepared from the following ingredients according to Example I of Canadian Letters Pat. No. 1,007,948 the specification for which is incorporated by reference herein:

| Ingredients | Parts by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table I of Example XIV. Each of the detergent samples has an excellent aroma as set forth in Table I of Example XIV.

EXAMPLE XIX

DRYER-ADDED FABRIC SOFTENER ARTICLE

Utilizing the procedure of Example I at column 15 of U.S. Pat. No. 3,632,396, the specification for which is incorporated by reference herein, a non-woven cloth substrate useful as a dryer-added fabric softening article of manufacture is prepared wherein the substrate, the substrate coating and the outer coating and the perfuming material are as follows:
1. A water "dissolvable" paper ("Dissolvo Paper")
2. Adogen 448 (m.p. about 140° F. ) as the substrate coating; and
3. An outer coating having the following formulation (m.p. about 150° F.):
   57% $C_{20-22}$ HAPS
   22% isopropyl alcohol
   20% antistatic agent
   1% of one of the substances of Table I of Example XIV, supra.

Fabric softening compositions containing one of the substances of Table I of Example XIV consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1:1 by weight of the substrate.

Pleasant aromas as set forth in Table I of Example XIV are imparted to the head space in the dryer on operation thereof using the said drier-added fabric softening non-woven fabric.

EXAMPLE XX

RASPBERRY FLAVOR FORMULATION

The following basic raspberry flavor formulation is produced:

| Ingredients | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| | 1000.0 |

The compound having the structure:

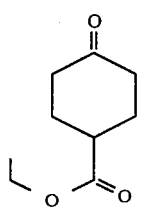

is added to half of the above formulation at the rate of 0.2%. The formulation with the compound having the structure:

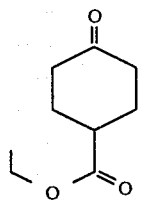

prepared according to Example II is compared with the formulation without that compound at the rate of 0.01% (100 ppm) in water and evaluated by a bench panel consisting of five members, none of whom is associated with the inventors on the instant application and each of whom is independent of the assignee of the instant application.

The flavor containing the compound having the structure:

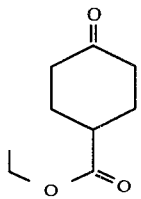

is found to have a substantially more pleasant and better raspberry aroma. It is the unanimous opinion of the bench panel that the chemical having the structure:

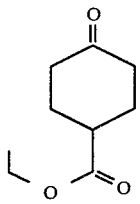

rounds out the flavor and contributes to a very natural fresh aroma and taste found in fresh raspberries whereby a raspberry kernel character is imparted in both aroma and taste. Accordingly, the flavor with the addition of the compound having the structure:

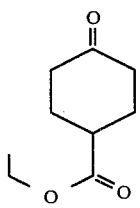

is considered substantially better than the flavor without the compound having the structure:

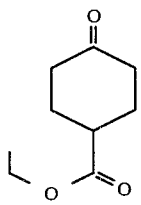

EXAMPLE XXI

FLAVOR COMPOSITION

The following basic walnut flavor formulation is prepared as follows:

| Ingredients | Parts by Weight |
|---|---|
| Ethyl-2-methyl butyrate | 10.0 |
| Vanillin | 40.0 |
| Butyl valerate | 40.0 |
| 2,3-Diethyl pyrazine | 5.0 |
| Methyl cyclopentenolone | 80.0 |
| Benzaldehyde | 60.0 |
| Valerian oil Indian | 0.5 |
| (1% in 95% aqueous ethanol alcohol) | |
| Propylene glycol | 764.5 |

The resulting flavor is split into four portions. To each of the first three portions, separately, the following materials are added:

(i) The compound having the structure:

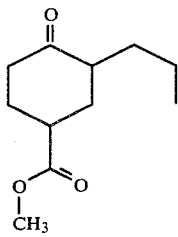

produced according to Example VII;

(ii) The compound having the structure:

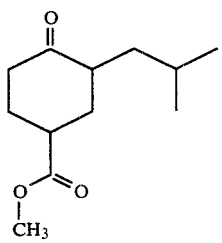

prepared according to Example VIII; and (iii) The compound having the structure:

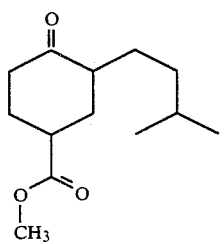

prepared according to Example X.

To the fourth portion nothing is added.

The compounds of Examples VII, VIII and X are added at the rates of 1.5% each.

The formulations with the alkyl substituted and unsubstituted para-carboalkoxy cyclohexanones of our invention as set forth, supra are compared to the formulation which does not have such a alkyl substituted and unsubstituted para-carboalkoxy cyclohexanones. The formulation containing the alkyl substituted and unsubstituted para-carboalkoxy cyclohexanones are evaluated by an independent bench panel of flavor panelist who are not associated with the inventors or with the assignee of the instant application as follows:

(i) A woody, balsamic, fresh walnut kernel and walnut skin-like taste with excellent caramel-like, maple sugar-like nuances;

(ii) A roasted walnut-like aroma and taste with maple/hazel-nut nuances; and (iii) A natural walnut aroma and taste with fresh almond aroma and taste nuances.

The flavors that have added to them the above-named alkyl substituted and unsubstituted para-carboalkoxy cyclohexanones of our invention are unanimously preferred by the group of flavor panelist over the flavor not containing said alkyl substituted and unsubstituted para-carboalkoxy cyclohexanones.

EXAMPLE XXII

BEVERAGE

The addition of one of the alkyl substituted and unsubstituted para-carboalkoxy cyclohexanones of our invention set forth below prepared according to the examples as set forth below, at the rate of 7 ppm to a commercial cola beverage gives the beverage a fuller long-lasting natural like taste having the following flavor nuances:

|  |  | Aroma and Taste |
|---|---|---|
| (i) | The compound having the structure: 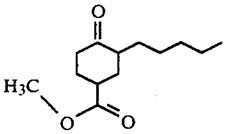 prepared according to one of Examples III, IV, XI(C) or XII. | A cola beverage aroma and taste with tart unripened lime aroma and taste nuances. |
| (ii) | The compound having the structure: 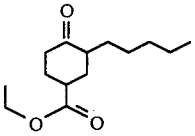 prepared according to Example V. | A fresh natural cola aroma and taste with aesthetically pleasing bitter lemony aroma and taste nuances. |
| (iii) | The compound having the structure: 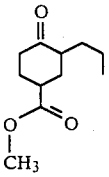 prepared according to Example VII. | A sweetened cola beverage taste with maple sugar-like nuances. |
| (iv) | The compound having the structure: 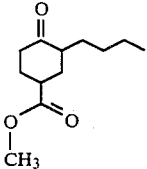 prepared according to Example IX. | An interesting cola beverage aroma and taste with cocoa and coffee-like nuances. |

In all cases a bench panel having five members not associated with the inventorship entity of the instant application or the assignee of the instant application unanimously is of the opinion that the cola beverages with the above-mentioned alkyl substituted and unsubstituted paracarboalkoxy cyclohexanones of our invention are preferred over the cola beverages without those alkyl substituted and unsubstituted para-carboalkoxy cyclohexanones of our invention.

EXAMPLE XXIII

FLAVORED PEANUT BUTTER

To a standard peanut butter mix (PLANTERS®) is admixed at the rate of 4 ppm one of the following materials:

(i) The compound having the structure:

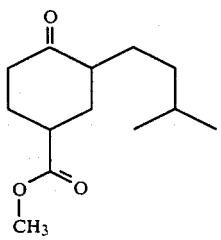

produced according to Example X;

(ii) The compound having the structure:

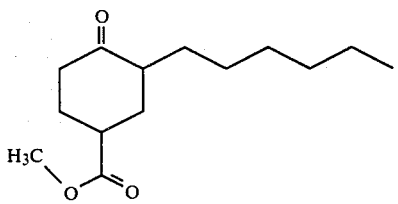

prepared according to Example VI;

(iii) The compound having the structure:

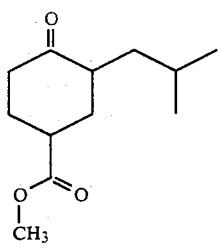

produced according to Example VIII.

To a fourth sample nothing is added.

The compound having the structure:

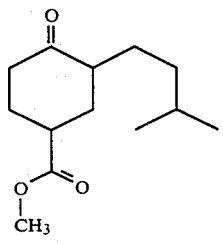

prepared according to Example X imparts to this peanut butter a fresh almond aroma and taste at the level of 10 ppm in addition to the pleasant peanut-like nuances.

The compound having the structure:

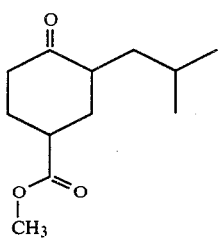

prepared according to Example VIII added at the rate of 5 ppm imparts to this peanut butter a pleasant maple/hazel nut aroma and taste profile at 5 ppm causing it to be more aesthetically pleasing.

The compound having the structure:

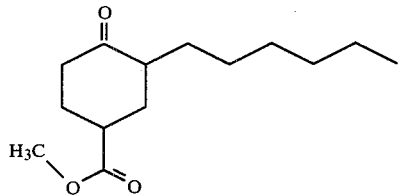

prepared according to Example VI imparts a fresh peanut aroma and taste profile ("newly picked peanuts") to this peanut butter.

A bench panel of five members not associated with the inventorship entity of the instant application and not associated with the assignee of the instant application, unanimously prefers the peanut butter containing the alkyl substituted and unsubstituted para-carboalkoxy cyclohexanones of our invention as set forth, supra to the peanut butters not containing the alkyl substituted and unsubstituted para-carboalkoxy cyclohexanones of our invention.

What is claimed is:

1. A substituted cyclohexanone carboxylic acid ester defined according to the structure:

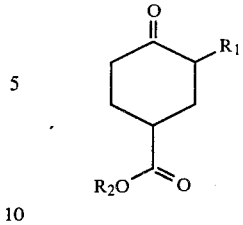

wherein $R_1$ represents $C_5$ or $C_6$ alkyl and $R_2$ represents methyl or ethyl.

2. The compound of claim 1 having the structure:

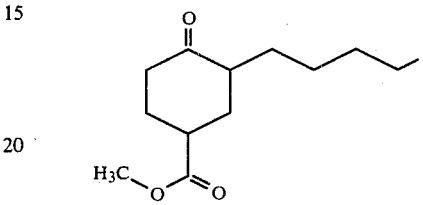

3. The compound of claim 1 having the structure:

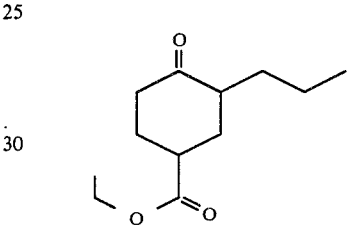

4. The compound of claim 1 having the structure:

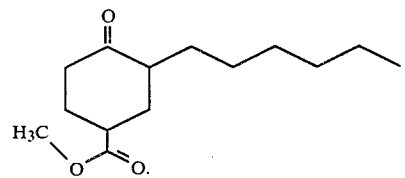

5. The compound of claim 1 having the structure:

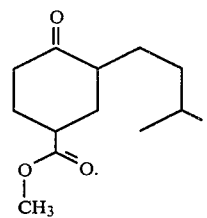

* * * * *